United States Patent [19]

Guthrie et al.

[11] Patent Number: 4,927,838
[45] Date of Patent: May 22, 1990

[54] PYRIDINE COMPOUNDS WHICH ARE USEFUL IN TREATING A DISEASE STATE CHARACTERIZED BY AN EXCESS OF PLATELET ACTIVATING FACTORS

[75] Inventors: Robert W. Guthrie, Saddle Brook; Richard W. Kierstead, North Caldwell; John G. Mullin, Hawthorne; Jefferson W. Tilley, North Caldwell, all of N.J.

[73] Assignee: Hoffman-La Roche Inc., Nutley, N.J.

[21] Appl. No.: 215,464

[22] Filed: Jul. 5, 1988

Related U.S. Application Data

[63] Continuation-in-part of Ser. No. 179,616, Apr. 11, 1988, abandoned, which is a continuation-in-part of Ser. No. 72,199, Jul. 10, 1987, abandoned.

[51] Int. Cl.⁵ .................. A61K 31/44; C07D 409/12
[52] U.S. Cl. .................. 514/337; 514/346; 514/351; 514/352; 514/357; 546/255; 546/274; 546/269; 546/291; 546/300; 546/301; 546/302; 546/303; 546/304; 546/305; 546/309; 546/329; 546/331; 546/332; 546/334
[58] Field of Search ............... 546/291, 300, 301, 302, 546/304, 305, 309, 329, 331, 334, 255, 274, 269; 514/346, 351, 352, 357, 337, 332

[56] References Cited

U.S. PATENT DOCUMENTS 3,072,049   1/1963   Semb et al. .......................... 546/329

*Primary Examiner*—Richard A. Schwartz
*Assistant Examiner*—Zinna Worthington-Davis
*Attorney, Agent, or Firm*—George M. Gould; Bernard S. Leon; William G. Isgro

[57] ABSTRACT

The invention relates to compounds of the formula

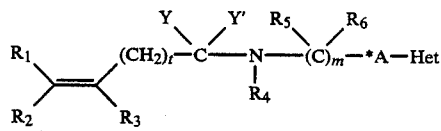

wherein Y and Y' are hydrogen or taken together are O or S, *A is paraphenylene or *——(CH$_2$)$_n$—(X-)$_s$—(CH$_2$)$_r$——, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, R$_1$ and R$_2$, independently, are lower alkyl, lower alkenyl or aryl, or one of R$_1$ or R$_2$ is hydrogen and the other is

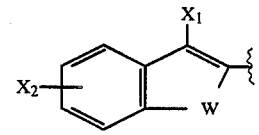

wherein W is

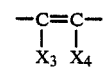

—CH$_2$—CH$_2$—, —CH$_2$—, O, S, or

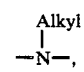

and
X$_1$ is lower alkyl, phenyl unsubstituted or mono-, di- or trisubstituted by lower alkoxy, lower alkyl or halogen, and X$_2$, X$_3$ and X$_4$, independently, are hydrogen, lower alkyl, lower alkoxy or halogen, R$_3$ is hydrogen, lower alkyl or aryl, R$_4$ is hydrogen, lower alkyl, aryl, aryl-lower alkyl or acyl, R$_5$ is hydrogen or lower alkyl,
R$_6$ is hydrogen, lower alkyl, cycloalkyl, Het-lower alkyl or aryl, Het is a monocyclic 6-membered heteroaromatic radical containing one or two nitrogen atoms, which radical may be substituted by lower alkyl, halogen or aryl, and the asterisk denotes the point of attachment,
and when R$_5$ and R$_6$ are different, their enantiomers and racemic mixtures thereof, when R$_1$ and R$_2$ are different, their geometric isomers, and pharmaceutically acceptable acid addition salts thereof.

40 Claims, No Drawings

PYRIDINE COMPOUNDS WHICH ARE USEFUL IN TREATING A DISEASE STATE CHARACTERIZED BY AN EXCESS OF PLATELET ACTIVATING FACTORS

CROSS REFERENCE TO RELATED APPLICATIONS

This application is a continuation-in-part of U.S. application Ser. No. 179,616, filed Apr. 11, 1988, now abandoned, which is a continuation-in-part of U.S. patent application Ser. No. 072,199, filed Jul. 10, 1987, now abandoned.

BRIEF SUMMARY OF THE INVENTION

The invention relates to compounds of the formula

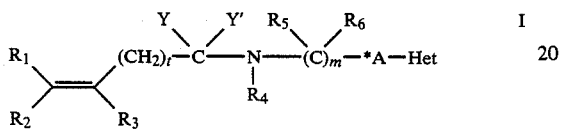

wherein Y and Y' are hydrogen or taken together are O or S, *A is paraphenylene or *——$(CH_2)_n$——$(X)_s$—$(CH_2)_r$——, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, $R_1$ and $R_2$, independently, are lower alkyl, lower alkenyl or aryl, or one of $R_1$ or $R_2$ is hydrogen and the other is

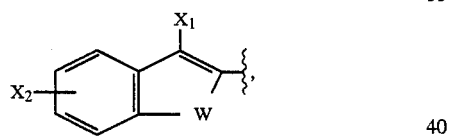

wherein W is

—$CH_2$—$CH_2$—, —$CH_2$, O, S or

and $X_1$ is lower alkyl, phenyl unsubstituted or mono-, di-or trisubstituted by lower alkoxy, lower alkyl or halogen, and $X_2$, $X_3$ and $X_4$, independently, are hydrogen, lower alkyl, lower alkoxy or halogen, $R_3$ is hydrogen, lower alkyl or aryl, $R_4$ is hydrogen, lower alkyl, aryl, aryl-lower alkyl or acyl, $R_5$ is hydrogen or lower alkyl, $R_6$ is hydrogen, lower alkyl, cycloalkyl, Het-lower alkyl or aryl, Het is a 6-membered heteroaromatic radical containing one or two nitrogen atoms, which radical may be substituted by lower alkyl, halogen or aryl, and the asterisk denotes the point of attachment,
and when $R_5$ and $R_6$ are different, their enantiomers and racemic mixtures thereof, when $R_1$ and $R_2$ are different, their geometric isomers, and pharmaceutically acceptable acid addition salts thereof.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

DETAILED DESCRIPTION OF THE INVENTION

The invention relates to compounds of the formula

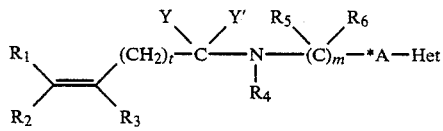

wherein Y and Y' are hydrogen or taken together are O or S, *A is paraphenylene or *——$(CH_2)_n$——$(X)_s$—$(CH_2)_r$——, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, $R_1$ and $R_2$, independently, are lower alkyl, lower alkenyl, or, aryl, or one of $R_1$ or $R_2$ is hydrogen and the other is

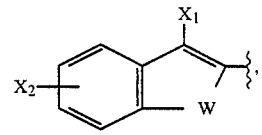

wherein W is

—$CH_2$—$CH_2$—, —$CH_2$, O, S or

and $X_1$ is lower alkyl, phenyl unsubstituted or mono-, di-or trisubstituted by lower alkoxy, lower alkyl or halogen, and $X_2$, $X_3$ and $X_4$, independently, are hydrogen, lower alkyl, lower alkoxy or halogen, $R_3$ is hydrogen, lower alkyl or aryl, $R_4$ is hydrogen, lower alkyl, aryl or acyl, $R_5$ is hydrogen or lower alkyl, $R_6$ is hydrogen, lower alkyl, cycloalkyl, Het-lower alkyl or aryl, Het is a 6-membered heteroaromatic radical containing one or two nitrogen atoms which radical may be substituted by lower alkyl, halogen or aryl, and the asterisk denotes the point of attachment,
and when $R_5$ and $R_6$ are different, their enantiomers and racemic mixtures thereof, when $R_1$ and $R_2$ are different, their geometric isomers, and pharmaceutically acceptable acid addition salts thereof.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "cycloalkyl" denotes a cyclic alkyl group of 3 to 6 carbon atoms, for example, cyclopropyl, cyclohexyl, and the like. The term "lower alkoxy" denotes an alkyl ether group in which the alkyl group is as described above, for example, methoxy, ethoxy, propoxy, pentoxy and the like. The term "lower alkenyl" denotes a straight or branched chain unsaturated hydrocarbon containing 3 to 7 carbon atoms, for example, propenyl, butenyl and the like.

The term "halogen" denotes all the halogens, i.e., bromine, chlorine, fluorine, and iodine. The term "aryl" preferably denotes naphthalenyl, phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen.

The term "acyl" denotes an "alkanoyl" group derived from an aliphatic carboxylic acid of 1 to 7 carbon atoms, for example, formyl, acetyl, propionyl, and the like; an aryl-lower alkanoyl group and an "aroyl" group derived from an aromatic carboxylic acid, such as benzoyl and the like.

The term "Het" denotes a monocyclic 6-membered heteroaromatic radical containing one or two nitrogen atoms, which radical may be substituted by lower alkyl, halogen or phenyl, for example, pyridinyl, 2-methyl-3-pyridinyl, pyrimidinyl and the like.

As already indicated the compounds of formula I, when $R_5$, $R_6$ and Het-A*- are different can exist as enantiomers or racemic mixtures.

The invention encompasses all the isomers and mixtures thereof.

A preferred group of compounds of formula I are those wherein $R_1$ and $R_2$ are lower alkyl or aryl, or, when $R_1$ is hydrogen, $R_2$ is

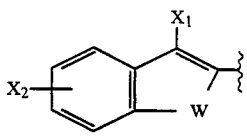

wherein $X_1$, $X_2$ and W are as previously described, $R_3$ is hydrogen or lower alkyl, $R_4$ and $R_6$ are hydrogen, $R_5$ is hydrogen, lower alkyl or cycloalkyl, *A is *—$(CH_2)_n$—$(X)_s$—$(CH_2)_r$ wherein $n+r=2$ to 6, s is 0, Het is a monocyclic 6 membered heteroaromatic ring containing one or two nitrogen atoms, Y or Y' are hydrogen or taken together are oxygen or sulfur, m is 1, t=0 to 4.

A more preferred group of compounds of formula I are those wherein $R_1$ is hydrogen, $R_2$ is

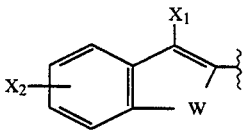

wherein $X_1$, $X_2$ and W are as previously described, $R_3$ is hydrogen or lower alkyl, *A is *—$(CH_2)_n$—$(X)_s$—$(CH_2)_r$ wherein $n+r=3$, s is 0, Het is pyridinyl or pyrimidinyl unsubstituted or substituted by lower alkyl, $R_4$ and $R_6$ are hydrogen, $R_5$ is hydrogen, lower alkyl or cyclopropyl, m is 1, t is 0, and Y and Y' are hydrogen or taken together are oxygen.

Another more preferred group of compounds of formula I are those wherein $R_1$ is lower alkyl or aryl, $R_2$ is aryl, $R_3$ is hydrogen or lower alkyl, *A is *—$(CH_2)_n$—$(X)_s$—$(CH_2)_r$ wherein $n+r=3$, s is 0, Het is pyridinyl or pyrimidinyl unsubstituted or substituted by lower alkyl, $R_4$ and $R_6$ are hydrogen, $R_5$ is hydrogen, lower alkyl or cyclopropyl, m is 1, t is 0 or 2, and Y and Y' are hydrogen or taken together are oxygen.

A most preferred group of compounds of formula I are those wherein $R_1$ is hydrogen, $R_2$ is

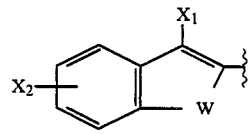

wherein W is

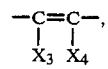

—$CH_2$—, O, S or

$X_1$ is butyl, pentyl, hexyl, phenyl or phenyl mono-, di- or trisubstituted by halogen or lower alkoxy, $X_2$, $X_3$ and $X_4$, independently, are hydrogen, lower alkoxy or halogen, $R_3$, $R_4$ and $R_6$ are hydrogen, $R_5$ is hydrogen, lower alkyl or cycloalkyl, m is 1, t is 0, Y and Y' taken together are oxygen, and Het is 3-pyridinyl or 2-methylpyridinyl.

Another most preferred group of compounds of formula I are those where $R_1$ is butyl, pentyl or hexyl or phenyl with up to 3-substituents selected from halogen, or lower alkoxy, $R_2$ is phenyl with up to 3-substituents selected from halogen or lower alkoxy, $R_3$, $R_4$ and $R_6$ are hydrogen, $R_5$ is hydrogen, lower alkyl or cyclopropyl, m is 1, t is 2, Y and Y' are hydrogen or taken together is oxygen and Het is 3-pyridinyl or 2-methyl-3-pyridinyl.

Preferred compounds of the invention are:

5,5-diphenyl-N-[4-(3-pyridinyl)butyl]-4-pentenamide;
5,5-bis(4-methoxyphenyl)-N-[4-(3-pyridinyl)butyl]-4-pentenamide;
5,5-bis(4-fluorophenyl)-N-[4-(3-pyridinyl)butyl]-4-pentenamide;
N-(5,5-diphenyl-4-pentenyl)-3-pyridinebutanamine;
[R-(E)]-3-(1-butyl-6-methoxy-2-naphthalenyl)-N-[1-methyl-4-(3-pyridinyl)butyl]-2-propenamide;
[R-(E)]-3-[6-methoxy-1-(4-methoxyphenyl)-2-naphthalenyl]-N-[1-methyl-4-(3-pyridinyl)butyl]-2-propenamide;
[R-(E)]-3-(1-butyl-4-methoxy-2-naphthalenyl)-N-[1-methyl-4-(3-pyridinyl)butyl]-2-propenamide;
(E)-3-(1-butyl-4-methoxy-2-naphthalenyl)-N-[6-(3-pyrimidinyl)hexyl]-2-propenamide;
[R-(E)]-3-(6-methoxy-3-pentylinden-2-yl)-N-[1-methyl-4-(3-pyridinyl)butyl]-2-propenamide;

[R-(E)]-3-(6-methoxy-3-pentylbenzo[b]thien-2-yl)-N-[1-methyl-4-(3-pyridinyl)butyl]-2-propenamide;
[R-(E)]-3-(6-methoxy-3-pentylbenzofuran-2-yl)-N-[1-methyl-4-(3-pyridinyl)butyl]-2-propenamide; and
[R-(E)]-3-(6-methoxy-1-methyl-3-pentylindol-2-yl)-N-[1-ethyl-4-(3-pyridinyl)butyl]-2-propenamide.

Exemplary compounds of formula I of the invention are:
N-(4,4-diphenyl-3-butenyl)-3-pyridinebutanamine;
N-[4,4-bis(4-methoxyphenyl)-3-butenyl]-3-pyridinebutanamine;
N-[5,5-bis(4-methoxyphenyl)-4-pentenyl]-3-pyridinebutanamine;
N-[5,5-bis(4-fluorophenyl)-4-pentenyl]-3-pyridinebutanamine;
N-[5,5-bis(3-methoxyphenyl)-4-pentenyl]-3-pyridinebutanamine;
N-(5,5-bis(4-methoxyphenyl)-4-pentenyl]-5-pyrimidinebutanamine;
N-[5,5-bis(3-methoxyphenyl)-4-pentenyl]-5-pyrimidinebutanamine;
N-[5,5-bis(3-fluorophenyl)-4-pentenyl]-5-pyrimidinebutanamine;
N-[5,5-bis(3-nitrophenyl)-4-pentenyl]-5-pyrimidinebutanamine;
N-[5,5-bis(4-nitrophenyl)-4-pentenyl]-5-pyrimidinebutanamine;
N-[5,5-bis(3-chlorophenyl)-4-pentenyl]-3-pyridinebutanamine;
N-[5,5-bis(4-bromophenyl)-4-pentenyl]-3-pyridinebutanamine;
N-(5,5-diphenyl-4-pentenyl)-5-pyrimidinebutanamine;
N-(5,5-diphenyl-4-pentenyl)-5-pyrimidinehexanamine;
N-(5,5-diphenyl-4-pentenyl)-5-pyrimidinepropanamine;
N-(5,5-diphenyl)-4-pentenyl]-5-pyrimidinepentanamine;
N-(5,5-diphenyl)-4-pentenyl]-N-methyl-5-pyrimidinebutanamine;
N-[5,5-bis(4-methoxyphenyl)-4-pentenyl]-N-methyl-3-pyridinebutanamine;
(E)-N-(5-phenyl-4-octenyl)-5-pyrimidinebutanamine;
(Z)-N-(5-phenyl-4-nonenyl)-5-pyrimidinebutanamine;
(E)-N-[5-(4-methoxyphenyl)-4-pentenyl]-3-pyridinebutanamine;
(E)-N-[5-(4-methoxyphenyl)-4-hexenyl]-3-pyridinebutanamine;
(E)-N-[5-(4-methoxyphenyl)-4-octenyl]-3-pyridinebutanamine;
(Z)-N-[5-(4-methoxyphenyl)-4-octenyl]-3-pyridinebutanamine;
(E)-N-(5-ethyl-4-nonenyl)-3-pyridinebutanamine;
(E)-N-(5-methyl-4-octenyl)-3-pyridinebutanamine;
N-(5-butyl-4-nonenyl)-3-pyridinebutanamine;
N-(5-butyl-4-nonenyl)-N-methyl-3-pyridinebutanamine;
N-[5,5-bis(4-methoxyphenyl)-4-pentenyl]-N-[4-(3-pyridinyl)butyl]formamide;
N-[5,5-bis(3-methoxyphenyl)-4-pentenyl]-N-[4-(3-pyridinyl)butyl]formamide;
N-[5,5-bis(4-methoxyphenyl)-4-pentenyl]-N-[4-(3-pyrimidinyl)butyl]formamide;
N-[5,5-bis(4-fluorophenyl)-4-pentenyl]-N-[4-(3-pyridinyl)butyl]formamide;
(E)-N-[5-(4-methoxyphenyl)-4-octenyl]-N-[4-(3-pyridinyl)butyl]formamide;
N-[6,6-bis(4-methoxyphenyl)-5-hexenyl]-N-[4-(3-pyridinyl)butyl]formamide;
N-[4,4-bis(4-methoxyphenyl)-3-butenyl]-N-[4-(3-pyridinyl)butyl]formamide;
(Z)-N-[5-(4-methoxyphenyl)-4-octenyl]-N-[4-(3-pyridinyl)butyl]formamide;
N-[5,5-bis(4-methoxyphenyl)-4-pentenyl]-N-[4-(3-pyridinyl)butyl]acetamide;
N-[5,5-bis(4-methoxyphenyl)-4-pentenyl]-N-[4-(3-pyridinyl)butyl]benzamide;
N-[5,5-bis(4-methoxyphenyl)-4-pentenyl]-N-[4-(3-pyridinyl)butyl]-4-fluorobenzamide;
N-[5,5-bis(4-methoxyphenyl)-4-pentenyl]-N-[4-(3-pyridinyl)butyl]-3-methoxybenzamide;
N-[5,5-bis(4-bromophenyl)-4-pentenyl]-N-[4-(3-pyridinyl)butyl]benzamide;
N-(5-butyl-4-nonenyl)-N-[4-(3-pyridinyl)butyl]benzamide;
N-(5-butyl-4-nonenyl)-N-[4-(3-pyridinyl)butyl]acetamide;
N-(5-butyl-4-nonenyl)-N-[4-(3-pyridinyl)butyl]formamide;
5,5-diphenyl-N-[4-(3-pyrimidinyl)butyl]-4-pentenamide;
5,5-diphenyl-N-[5-(3-pyrimidinyl)pentyl]-4-pentenamide;
5,5-diphenyl-N-[4-(3-pyrimidinyl)propyl]-4-pentenamide;
(R)-5,5-diphenyl-N-[1-methyl-4-(3-pyridinyl)butyl]-4-pentenamide;
(R)-5,5-bis(4-methoxyphenyl)-N-[1-methyl-4-(3-pyridinyl)butyl]-4-pentenamide;
(rac)-5,5-bis(4-methoxyphenyl)-N-[1-methyl-3-(3-pyridinyl)propyl]-4-pentenamide;
(R)-5,5-bis(4-methoxyphenyl)-N-[1-ethyl-4-(3-pyridinyl)butyl]-4-pentenamide;
(R)-5,5-bis(3-methoxyphenyl)-N-[1-methyl-4-(3-pyridinyl)butyl]-4-pentenamide;
5,5-bis(4-methoxyphenyl)-N-[1,1-dimethyl-4-(3-pyridinyl)butyl]-4-pentenamide;
(R)-5,5-bis(4-methoxyphenyl)-N-[1-propyl-4-(3-pyridinyl)butyl]-4-pentenamide;
(rac)-6,6-bis(4-methoxyphenyl)-N-[1-methyl-4-(3-pyridinyl)butyl]-4-hexenamide;
(R)-5,5-bis(4-methoxyphenyl)-N-[1-propyl-4-(3-pyridinyl)butyl]-4-pentenamide;
(R)(E)-5-(4-methoxyphenyl)-5-phenyl-N-[1-methyl-4-(3-pyridinyl)butyl]-4-pentenamide;
(E)-5-(4-methoxyphenyl)-5-phenyl-N-[4-(3-pyridinyl)butyl]-4-pentenamide;
(R)(E)-5-(4-methoxyphenyl)-5-methyl-N-[1-methyl-4-(3-pyridinyl)butyl]-4-pentenamide;
(R)(Z)-5-(4-methoxyphenyl)-5-methyl-N-[1-methyl-4-(3-pyridinyl)butyl]-4-pentenamide;
(rac)(E)-5-(2-methoxyphenyl)-5-methyl-N-[1-methyl-4-(3-pyridinyl)butyl]-4-pentenamide;
(R)-5,5-bis(3-chlorophenyl)-N-[1-methyl-4-(3-pyridinyl)butyl]-4-pentenamide;
5,5-bis(4-methylphenyl)-N-[4-(3-pyridinyl)butyl]-4-pentenamide;
(R)-5,5-bis(3,4-dimethoxyphenyl)-N-[1-methyl-4-(3-pyridinyl)butyl]-4-pentenamide;
(R)-5,5-bis(3,4-dichlorophenyl)-N-[1-methyl-4-(3-pyridinyl)butyl]-4-pentenamide;
(R)(E)-5-(3-methoxyphenyl)-5-(4-fluorophenyl)-N-[1-methyl-4-(3-pyridinyl)butyl]-4-pentenamide;
(R)-5,5-bis(3-methylphenyl)-N-[1-methyl-4-(3-pyridinyl)butyl]-4-pentenamide;
(R)-5,5-bis(3-methoxyphenyl)-N-[1-methyl-4-(3-pyridinyl)butyl]-5-hexenamide;
(R)-5,5-bis(3-methoxyphenyl)-N-[1-methyl-4-(3-pyridinyl)butyl]-3-butenamide;

(R)-5,5-bis(4-methoxyphenyl)-N-[1-methyl-4-(2-methyl-3-pyridinyl)butyl]-4-pentenamide;
(R)-5,5-bis(3-methoxyphenyl)-N-[1-methyl-4-(6-methyl-3-pyridinyl)butyl]-4-pentenamide;
(rac)-5,5-bis(3-methoxyphenyl)-N-[1-methyl-4-(2-ethyl-3-pyridinyl)butyl]-4-pentenamide;
[R-(E)]-3-(6-methoxy-1-propyl-2-naphthalenyl)-N-[1-methyl-4-(3-pyridinyl)butyl]-2-propenamide;
[R-(E)]-3-(6-methoxy-1-pentyl-2-naphthalenyl)-N-[1-methyl-4-(3-pyridinyl)butyl]-2-propenamide;
(E)-3-(1-butyl-6-methoxy-2-naphthalenyl)-N-[4-(3-pyridinyl)butyl]-2-propenamide;
(E)-3-(1-butyl-6-methoxy-2-naphthalenyl)-N-[4-(3-pyrimidinyl)-butyl]-2-propenamide;
[R-(E)]-3-(1-butyl-6-methoxy-2-naphthalenyl)-N-[1-ethyl-4-(3-pyridinyl)butyl]-2-propenamide;
[R-(E)]-3-(3,4-dihydro-6-methoxy-1-propyl-2-naphthalenyl)-N-[1-methyl-4-(3-pyridinyl)butyl]-2-propenamide;
[R-(E)]-3-(3,4-dihydro-6-methoxy-1-pentyl-2-naphthalenyl)-N-[1-methyl-4-(3-pyridinyl)butyl]-2-propenamide;
(E)-3-(1-butyl-3,4-dihydro-6-methoxy-2-naphthalenyl)-N-[4-(3-pyridinyl)butyl]-2-propenamide;
(E)-3-(1-butyl-3,4-dihydro-6-methoxy-2-naphthalenyl)-N-[4-(3-pyrimidinyl)butyl]-2-propenamide;
[R-(E)]-3-(1-butyl-3,4-dihydro-6-methoxy-2-naphthalenyl)-N-[1-ethyl-4-(3-pyridinyl)butyl]-2-propenamide;
[R-(E)]-3-[3,4-dihydro-6-methoxy-1-(4-methylphenyl)-2-napht halenyl]-N-[1-methyl-4-(3-pyridinyl)butyl]-2-propenamide;
[R-(E)]-3-[3,4-dihydro-6-methoxy-1-(3-methoxyphenyl)-2-naphthalenyl]-N-[1-methyl-4-(3-pyridinyl)butyl]-2-propenamide;
[R-(E)]-3-[3,4-dihydro-6-methoxy-1-(4-methoxyphenyl)-2-naphthalenyl]-N-[1-methyl-4-(3-pyridinyl)butyl]-2-propenamide;
[R-(E)]-3-[1-(4-chlorophenyl)-3,4-dihydro-6-methoxy)-2-naphthalenyl]-N-[1-methyl-4-(3-pyridinyl)butyl]-2-propenamide;
(E)-3-[6-methoxy-1-(4-methoxyphenyl)-2-naphthalenyl]-N-[4-(3-pyridinyl)butyl]-2-propenamide;
[R-(E)]-3-[6-methoxy-1-(4-methylphenyl)-2-naphthalenyl]-N-[1-methyl-4-(3-pyridinyl)butyl]-2-propenamide;
[R-(E)]-3-[6-methoxy-1-(3-methoxyphenyl)-2-naphthalenyl]-N-[1-methyl-4-(3-pyridinyl)butyl]-2-propenamide;
[R-(E)]-3-[6-methyl-1-(4-methoxyphenyl)-2-naphthalenyl]-N-[1-methyl-4-(3-pyridinyl)butyl]-2-propenamide;
[R-(E)]-3-[1-(4-chlorophenyl)-6-methoxy)-2-naphthalenyl]-N-[1-methyl-4-(3-pyridinyl)butyl]-2-propenamide;
[R-(E)]-3-(1-butyl-5-methoxy-2-naphthalenyl)-N-[1-methyl-4-(3-pyridinyl)butyl]-2-propenamide;
[R-(E)]-3-(5-methoxy-1-pentyl-2-naphthalenyl)-N-[1-methyl-4-(3-pyridinyl)butyl]-2-propenamide;
(E)-3-(1-butyl-5-methoxy-2-naphthalenyl)-N-[4-(3-pyridinyl)butyl]-2-propenamide;
(E)-3-(1-butyl-5-methoxy-2-naphthalenyl)-N-[4-(3-pyrimidinyl)-butyl]-2-propenamide;
[R-(E)]-3-(1-butyl-5-methoxy-2-naphthalenyl)-N-[1-ethyl-4-(3-pyridinyl)butyl]-2-propenamide;
[R-(E)]-3-(1-butyl-7-methoxy-2-naphthalenyl)-N-[1-methyl-4-(3-pyridinyl)butyl]-2-propenamide;
[R-(E)]-3-(7-methoxy-1-pentyl-2-naphthalenyl)-N-[1-methyl-4-(3-pyridinyl)butyl]-2-propenamide;
(E)-3-(1-butyl-7-methyl-2-naphthalenyl)-N-[4-(3-pyridinyl)butyl]-2-propenamide;
(E)-3-(1-butyl-7-methoxy-2-naphthalenyl)-N-[4-(3-pyrimidinyl)-butyl]-2-propenamide;
[R-(E)]-3-(1-butyl-7-methoxy-2-naphthalenyl)-N-[1-ethyl-4-(3-pyridinyl)butyl]-2-propenamide;
[(S)-(E)]-3-(1-butyl-4,7-dimethoxy-2-naphthalenyl)-N-[1-methyl-4-(3-pyridinyl)butyl]-2-propenamide;
[R-(E)]-3-(4,7-dimethoxy-1-pentyl-2-naphthalenyl)-N-[1-methyl-4-(3-pyridinyl)butyl]-2-propenamide;
(E)-3-(1-butyl-4,7-dimethoxy-2-naphthalenyl)-N-[4-(3-pyridinyl)butyl]-2-propenamide;
(E)-3-(1-butyl-4,7-dimethoxy-2-naphthalenyl)-N-[4-(3-pyrimidinyl)butyl]-2-propenamide;
[R-(E)]-3-(1-butyl-4,7-dimethoxy-2-naphthalenyl)-N-[1-ethyl-4-(3-pyridinyl)butyl]-2-propenamide;
[R-(E)]-3-(1-butyl-4-methyl-2-naphthalenyl)-N-[1-methyl-4-(3-pyridinyl)butyl]-2-propenamide;
(E)-3-(1-butyl-4-methoxy-2-naphthalenyl)-N-[6-(3-pyrimidinyl)-hexyl]-2-propenamide;
[R-(E)]-3-(4-methoxy-1-pentyl-2-naphthalenyl)-N-[1-methyl-4-(3-pyridinyl)butyl]-2-propenamide;
(E)-3-(1-butyl-4-methoxy-2-naphthalenyl)-N-[4-(3-pyridinyl)butyl]-2-propenamide;
(E)-3-(1-butyl-4-methoxy-2-naphthalenyl)-N-[4-(3-pyrimidinyl)-butyl]-2-propenamide;
[R-(E)]-3-(1-butyl-4-methoxy-2-naphthalenyl)-N-[1-ethyl-4-(3-pyridinyl)butyl]-2-propenamide;
(E)-3-[7-methyl-1-(3-methoxyphenyl)-2-naphthalenyl]-N-[4-(3-pyridinyl)butyl]-2-propenamide;
[R-(E)]-3-(6-methoxy-3-pentylinden-2-yl)-N-[1-methyl-4-(3-pyridinyl)butyl]-2-propenamide;
(E)-3-(6-methoxy-3-pentylinden-2-yl)-N-[4-(3-pyridinyl)butyl]-2-propenamide;
(E)-3-(6-methoxy-3-pentylinden-2-yl)-N-[4-(3-pyrimidinyl)butyl]-2-propenamide;
[R-(E)]-3-(6-methoxy-3-propylinden-2-yl)-N-[1-methyl-4-(3-pyridinyl)butyl]-2-propenamide;
[R-(E)]-3-(6-chloro-3-pentylinden-2-yl)-N-[1-methyl-4-(3-pyridinyl)butyl]-2-propenamide;
[R-(E)]-3-(6-methyl-3-methylinden-2-yl)-N-[1-methyl-4-(3-pyridinyl)butyl]-2-propenamide;
[R-(E)]-3-(6-methoxy-3-pentylbenzo[b]thien-2-yl)-N-[1-ethyl-4-(3-pyridinyl)butyl]-2-propenamide;
[R-(E)]-3-(6-methyl-3-pentylbenzo[b]thien-2-yl)-N-[1-methyl-4-(3-pyridinyl)butyl]-2-propenamide;
[R-(E)]-3-(6-methoxy-3-propylbenzo[b]thien-2-yl)-N-[1-methyl-4-(3-pyridinyl)butyl]-2-propenamide;
[R-(E)]-3-(3-butyl-6-methoxybenzo[b]thien-2-yl)-N-[1-methyl-4-(3-pyridinyl)butyl]-2-propenamide;
(E)-3-(6-methoxy-3-pentylbenzo[b]thien-2-yl)-N-[4-(3-pyridinyl)butyl]-2-propenamide;
(E)-3-(6-methoxy-3-pentylbenzo[b]thien-2-yl)-N-[4-(3-pyrimidinyl)butyl]-2-propenamide;
(E)-3-(6-methoxy-3-pentylbenzofuran-2-yl)-N-[4-(3-pyridinyl)-butyl]-2-propenamide;
(E)-3-(6-methoxy-3-pentylbenzofuran-2-yl)-N-[6-(3-pyridinyl)hexyl]-2-propenamide;
(E)-3-(6-methyl-3-pentylbenzofuran-2-yl)-N-[4-(3-pyridinyl)butyl]-2-propenamide;
[R-(E)]-3-(6-chloro-3-pentylbenzofuran-2-yl)-N-[1-methyl-4-(3-pyridinyl)butyl]-2-propenamide;
[R-(E)]-3-(6-methoxy-3-propylbenzofuran-2-yl)-N-[1-methyl-4-(3-pyridinyl)butyl]-2-propenamide;
[R-(E)]-3-(6-butyl-6-methoxybenzofuran-2-yl)-N-[1-methyl-4-(3-pyridinyl)butyl]-2-propenamide;

[R-(E)]-3-(6-methoxy-1-methyl-3-pentylindol-2-yl)-N-[1-methyl-4-(3-pyridinyl)butyl]-2-propenamide;

[R-(E)]-3-(6-chloro-1-methyl-3-pentylindol-2-yl)-N-[1-ethyl-4-(3-pyridinyl)butyl]-2-propenamide;

[R-(E)]-3-(1,6-dimethyl-3-pentylindol-2-yl)-N-[1-ethyl-4-(3-pyridinyl)butyl]-2-propenamide;

(E)-3-(6-methoxy-1-methyl-3-pentylindol-2-yl)-N-[4-(3-pyridinyl)butyl]-2-propenamide;

(E)-3-(6-methoxy-1-methyl-3-pentylindol-2-yl)-N-[4-(3-pyrimidinyl)butyl]-2-propenamide;

(E)-3-(6-methoxy-1-methyl-3-pentylindol-2-yl)-N-[6-(3-pyridinyl)hexyl]-2-propenamide; and

[R-(E)]-N-[1-ethyl-4-(3-pyridinyl)butyl]-3-(6-methoxy-1-methyl-3-propylindol-2-yl)-2-propenamide.

The compounds of formula I can be prepared as hereinafter described in Reaction Schemes I-XIII.

by evaporation of the reaction solvent and then, as in step (c), is treated with an amine of structure V, which are known compounds or can be prepared according to known procedures and which include the (R)- and (S)-enantiomers and racemic mixtures thereof, in the presence of a tertiary amine, preferably triethylamine, in an inert solvent such as dichloromethane or toluene at a temperature of from −80° C. to room temperature. The resulting corresponding compound of formula Ia can be isolated utilizing conventional methods such as crystallization or chromatography or the like.

In step (b), an alkenoic acid of formula II, which are known compounds or can be prepared according to known procedures and which include the (E)- and (Z)-isomers and mixtures thereof, is treated with an alkyl chloroformate in the presence of a tertiary amine, pref-

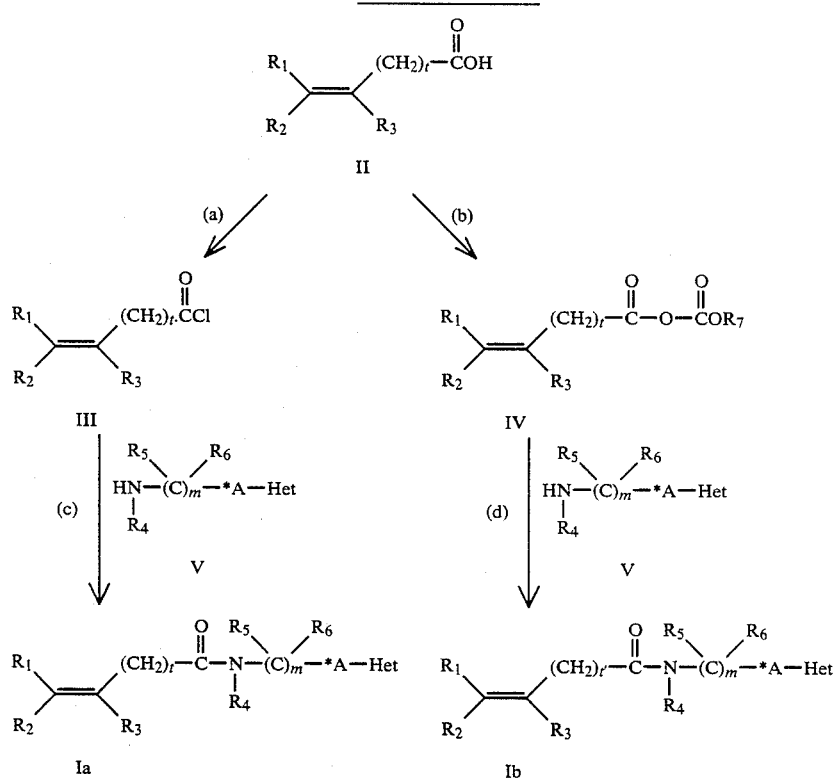

Reaction Scheme I wherein $R_1$, $R_2$, $R_3$, $R_4$, $R_5$, $R_6$, *A, Het, m and t are as previously described and $R_7$ is lower alkyl, arylalkyl or aryl, and t' is 0 or 2-10.

In Reaction Scheme I, step (a), an alkenoic acid of formula II, which are known compounds or can be prepared according to known procedures and which include the (E)- and (Z)-isomers and mixtures thereof, is treated with an acyl halide forming reagent, preferably oxalyl chloride or thionyl chloride, in an inert solvent, preferably dichloromethane or toluene at a temperature of from −80° C. to room temperature. The resulting corresponding compound of formula III can be isolated erably triethylamine, in an inert solvent, preferably diethyl ether or tetrahydrofuran at a temperature of from −20° C. to 10° C. The resulting mixed anhydride of formula IV is treated in situ as in step (d) with an amine of formula V, which are known compounds or can be prepared according to known procedures and which include the (R)- and (S)-enantiomers and racemic mixtures thereof, at a temperature of from −20° C. to room temperature. The resulting corresponding compound of formula Ib can be isolated utilizing conventional methods such as crystallization and chromatography or the like.

Reaction Scheme II

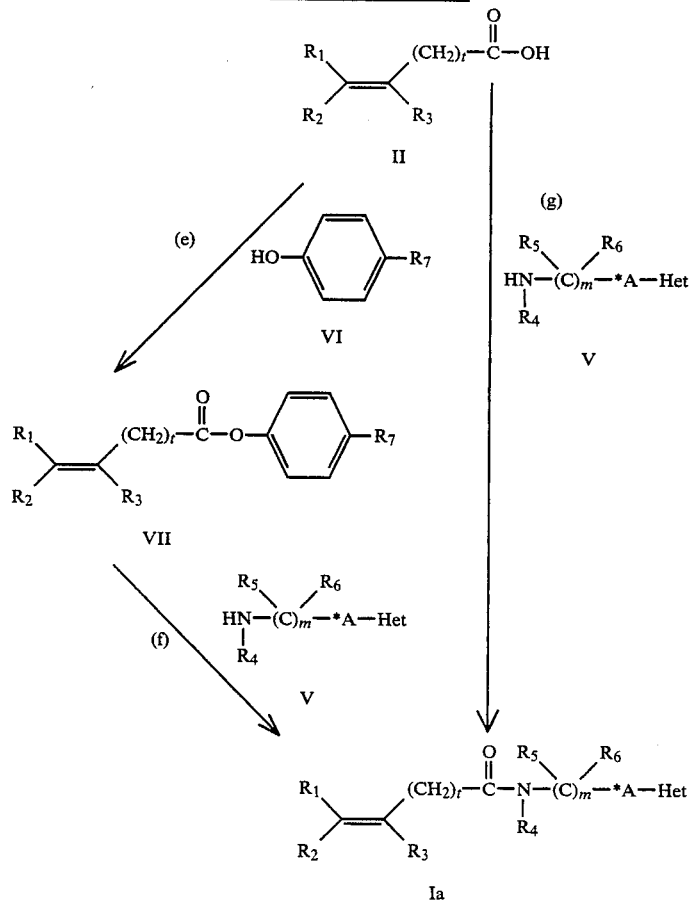

wherein $R_1$, $R_2$, $R_3$, $R_4$, $R_5$, $R_6$, *A, Het, m and t are as previously described and $R_7$ is hydrogen, halogen, lower alkoxy, lower alkyl, trihaloalkyl or nitro.

In Reaction Scheme II, step (e), a carboxylic acid of formula II, which are known compounds or can be prepared according to known procedures and which include as appropriate all geometric isomers and mixtures thereof, is reacted with a phenol of formula VI, which are known compounds or can be prepared according to known procedures and in the presence of a condensing agent, preferably dicyclohexylcarbodiimide, in an inert solvent such as dichloromethane, diethyl ether and dimethylformamide at a temperature of from −80° C. to room temperature. The resulting corresponding compound of formula VII can be isolated utilizing conventional methods, for example, crystallization, chromatography or the like.

In step (f), an "activated" ester of formula VII is reacted with an amine of formula V, which are known compounds or can be prepared according to known procedures and which include the (R) and (S) enantiomers and racemic mixtures thereof, in an inert solvent, preferably tetrahydrofuran and diethyl ether, at a temperature of from −80° C. to 100° C. The reaction is advantageously carried out wherein $R_7$ is nitro. The resulting corresponding compound of formula Ia can be isolated utilizing conventional methods, for example, crystallization, chromatography or the like.

In Reaction Scheme II, step (g), a carboxylic acid of formula II, which are known compounds or can be prepared according to known procedures and which include as appropriate all geometric isomers and mixtures thereof, is reacted with an amine of formula V, which are known compounds or can be prepared according to known procedures and which include the (R) and (S) enantiomers and racemic mixtures thereof, in the presence of a suitable coupling agent, for example, dicyclohexylcarbodiimide, optionally in the presence of a promotor, for example, 1-hydroxybenzotriazole in a polar aprotic solvent, for example, dimethylformamide or pyridine at a temperature of from −10° C. to 80° C. The resulting corresponding compound of formula Ia can be isolated utilizing conventional methods, for example, crystallization, chromatography or the like.

Reaction Scheme III

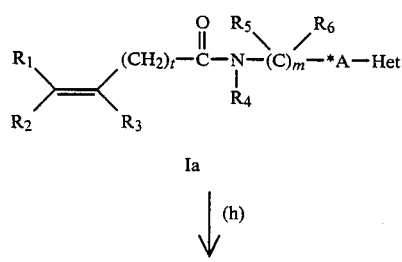

-continued
Reaction Scheme III

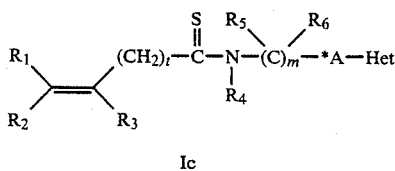

Ic wherein $R_1$, $R_2$, $R_3$, $R_4$, $R_5$, $R_6$, *A, Het, m and t are as previously described.

In Reaction Scheme III, step (h), an alkenamide of structure Ia, which include, where $R_5$ and $R_6$ are different, the enantiomers and racemic mixtures thereof, and where $R_1$ and $R_2$ are different, the (E)- and (Z)-isomers, is reacted with phosphorous pentasulfide in an inert solvent, for example, tetrahydrofuran or pyridine, at a temperature of from room temperature to reflux temperature. The resulting corresponding compound of formula Ic can be isolated by conventional means, such as chromatography, crystallization or the like.

isomers thereof, is reacted with a reducing agent, preferably sodium bis(2-methoxyethoxy)aluminium hydride in an inert solvent, for example toluene, at a temperature of from room temperature to 100° C. The resulting amine Ie can be isolated by conventional methods, for example, chromatography, crystallization or the like.

In Reaction Scheme IV, step (j), the amine of formula Ie which include, as appropriate, all geometric and enantiomeric or racemic forms thereof, is reacted with an acylating agent, for example, an acyl halide, in an inert solvent, for example, toluene, in the presence of a proton acceptor, for example, triethylamine, at a temperature of from −50° C. to room temperature, or when $R_8$ is hydrogen, with formic acid in an inert solvent, preferably toluene at reflux temperature, to give the corresponding amide of formula If. A compound of formula If can be isolated by conventional methods, such as chromatography, crystallization or the like.

An amide of formula If, may then be converted to the corresponding compound of formula Ig, by repetition of the reaction conditions heretofore described in step (i), above. An amine of formula Ig, may be isolated by

Reaction Scheme IV

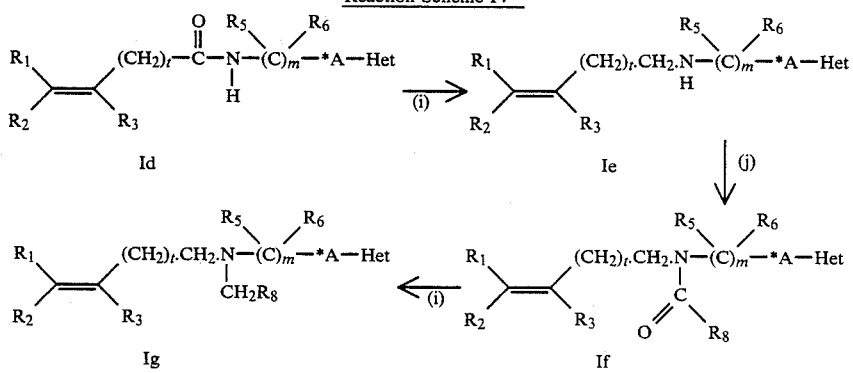

wherein $R_1$, $R_2$, $R_3$, $R_4$, $R_5$, $R_6$, *A, Het, m and t are as previously described and $R_8$ is hydrogen, lower alkyl, arylalkyl or aryl.

In Reaction Scheme IV, step (i), an alkenamide of formula Id which, when $R_5$ is different from $R_6$, include the enantiomers and racemic mixtures thereof, and/or when $R_1$ is different from $R_2$, include the (E)- and (Z)- conventional methods, such as crystallization, chromatography or the like.

Reaction Scheme V

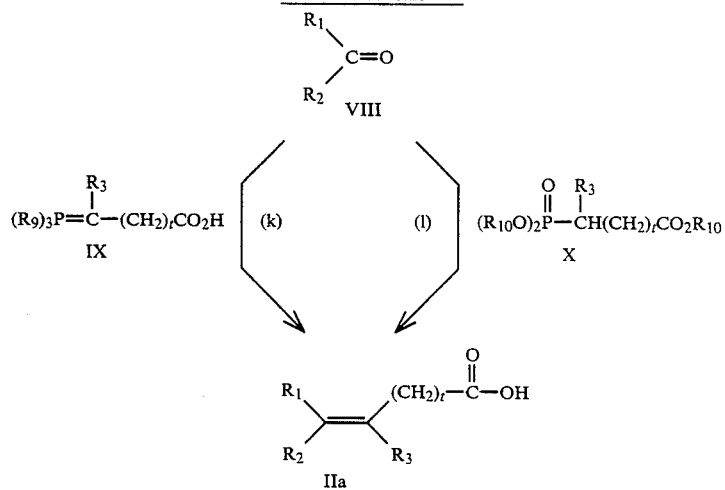

wherein $R_1$, $R_2$, $R_3$ and t are as previously described and $R_9$ and $R_{10}$ are, independently, lower alkyl, cycloalkyl or aryl.

In Reaction Scheme V, step (l), a phosphonoacetate triester of formula X, which are known compounds or can be prepared according to known procedures, is converted to its corresponding carbanion utilizing a strong base, preferably sodium hydride or sodium amide, in an inert solvent, preferably dimethylsulfoxide, dimethylformamide or tetrahydrofuran at temperatures of from 0° to 80° C., and then is reacted in situ with a carbonyl derivative of formula VIII. The resulting corresponding compound of formula II, which many be a mixture of isomers, can be separated, if necessary utilizing conventional methods such as crystallization, chromatography or the like.

In Reaction Scheme V, step (k), a carbonyl derivative of formula VIII, which are known compounds or can be prepared according to known procedures, is reacted with a (carboxyalkylidene)triarylphosphorane in an appropriate solvent, for example dimethylformamide or dimethylsulfoxide, at a temperature of from −20° C. to 80° C. The resulting corresponding compound of formula IIa, which may be a mixture of geometric isomers, can be separated, if necessary, by conventional methods such as crystallization, chromatography or the like.

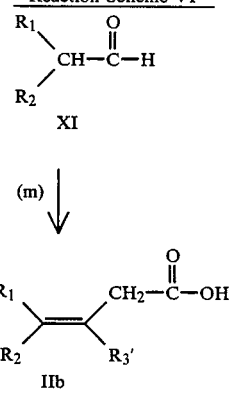

wherein $R_1$ and $R_2$ are as previously described and $R_3'$ is hydrogen.

In Reaction Scheme VI, step (m), a carboxaldehyde of formula XI, which are known compounds or can be prepared according to known procedures, is reacted with malonic acid in an aprotic polar basic solvent, for example, pyridine, optionally in the presence of a catalytic amount of a secondary amine, for example, pyrrolidine or morpholine, at a temperature of from 50° C. to 110° C. The resulting corresponding compound of formula IIb, which may be a mixture of isomers, can be separated by conventional methods, such as chromatography, crystallization and the like.

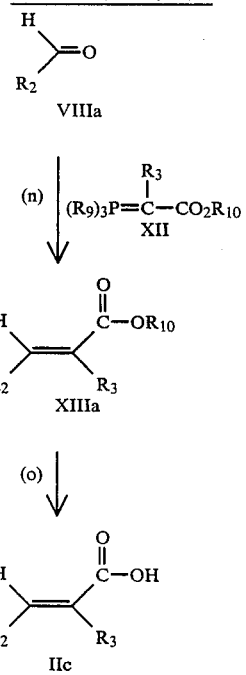

wherein $R_2$, $R_3$, $R_9$ and $R_{10}$ are as previously described.

In Reaction Scheme VII, step (n), a carboxaldehyde of formula VIIIa, which are known compounds or can be prepared according to known procedures, and is reacted with a (carboxalkoxyalkylidene)triarylphosphonate of formula XII, which are known compounds or can be prepared according to known procedures, in an appropriate solvent at a temperature of from −20° C. to 50° C. Use of an aprotic solvent, preferably dichloromethane, carbon tetrachloride or dimethylformamide leads to an isomer ratio of >10:1 in favor of the (E)-isomer around the newly formed double bond. When a protic solvent is used as the reaction solvent, preferably methanol or ethanol, a higher proportion of the (Z)-isomer is formed. The resulting corresponding compound of formula XIIIa may be separated, if necessary, into the (E) and (Z)-isomers utilizing conventional methods, for example, crystallization, chromatography or the like.

In step (o), the resulting carboxylic acid ester of formula XIIIa is reacted with an excess of alkali metal hydroxide in an solvent mixture, preferably methanol-water or ethanol-water, at a temperature of from room temperature to 85° C. The resulting corresponding compound of formula IIc can be isolated utilizing conventional methods, for example, crystallization, chromatography or the like.

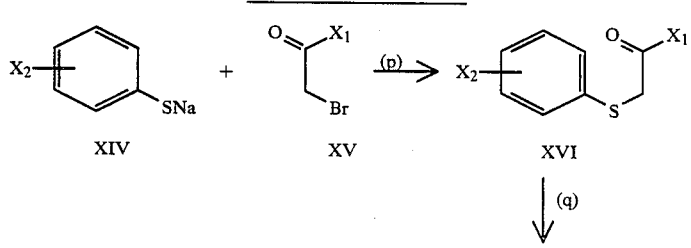

Reaction Scheme VIII

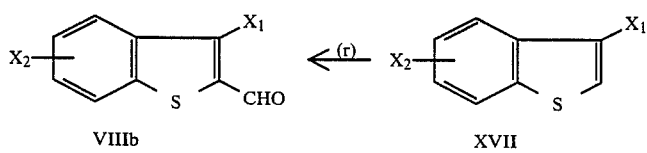

wherein $X_1$ and $X_2$ are as previously described. In Reaction Scheme VIII, step (p), a thiophenolate of formula XIV, which are known compounds or can be prepared according to known procedures, is reacted with an bromomethyl ketone of formula XV, which are known compounds or can be prepared according to known procedures, in an appropriate solvent, for example, water, at a temperature of from $-20°$ C. to $50°$ C. The resulting corresponding compound of formula XVI may be isolated utilizing conventional methods, for example, crystallization, chromatography or the like.

In step (q), a resulting compound of formula XVI is treated with a strong mineral acid, preferably sulfuric acid, at a temperature of from $-40°$ C. to room temperature. The resulting corresponding compound of formula XVII can be isolated utilizing conventional methods, for example, crystallization, chromatography or the like.

In step (r), a resulting benzo[b]thiophene of formula XVII is reacted with the Vilsmeier reagent prepared in the usual manner from phosphorus oxychloride and dimethylformamide, in dimethylformamide as solvent at a temperature of from $-20°$ C. to $50°$ C. The resulting intermediate imine is converted to the carboxaldehyde of formula VIIIb by treatment of the reaction mixture with an excess of a solution of an alkali metal hydroxide, for example, sodium hydroxide at a temperature of from $50°$ C. to $120°$ C. The resulting corresponding compound of formula VIIIb may be isolated utilizing conventional methods, for example, crystallization, chromatography or the like.

Reaction Scheme IX

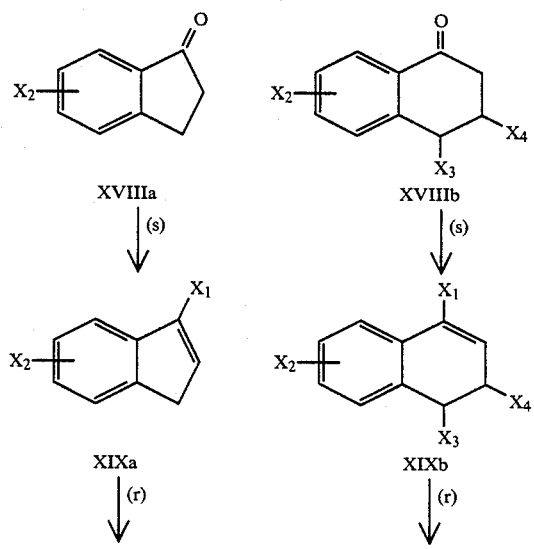

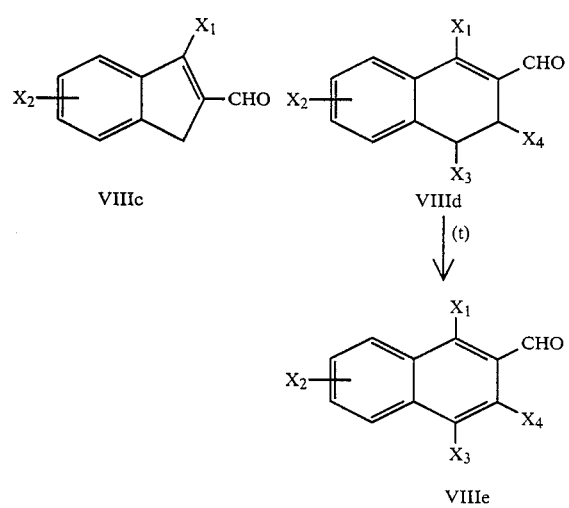

wherein $X_1$, $X_2$, $X_3$ and $X_4$ are as previously described.

In Reaction Scheme IX, step (s), a carbonyl compound of formula XVIIIa or XVIIIb, which are known compounds or can be prepared according to known methods, is reacted with the appropriate alkyl or aryl magnesium halide or alkyl lithium or aryl lithium in an inert solvent such as diethyl ether or tetrahydrofuran at a temperature of from $-80°$ C. to $65°$ C. The resulting corresponding compound of formula XIXa or XIXb can be isolated utilizing conventional methods, for example, crystallization, chromatography or the like.

Reaction Scheme IX, step (r), is the same as step (r) in Reaction Scheme VIII to give the carboxaldehyde of formula VIIIc or VIIId, which can be isolated utilizing conventional methods, for example, crystallization, chromatography or the like.

In step (t), a dihydronaphthalene of formula VIIId is reacted with a dehydrogenating agent, for example, tetrachloro-1,4-benzoquinone or 2,3-dichloro-4,5-dicyano-1,4-benzoquinone, in an appropriate solvent, for example, benzene, toluene or t-butanol, at a temperature of from room temperature to $100°$ C. The resulting corresponding compound of formula VIIIe can be isolated utilizing conventional methods, for example, crystallization, chromatography or the like.

Reaction Scheme X

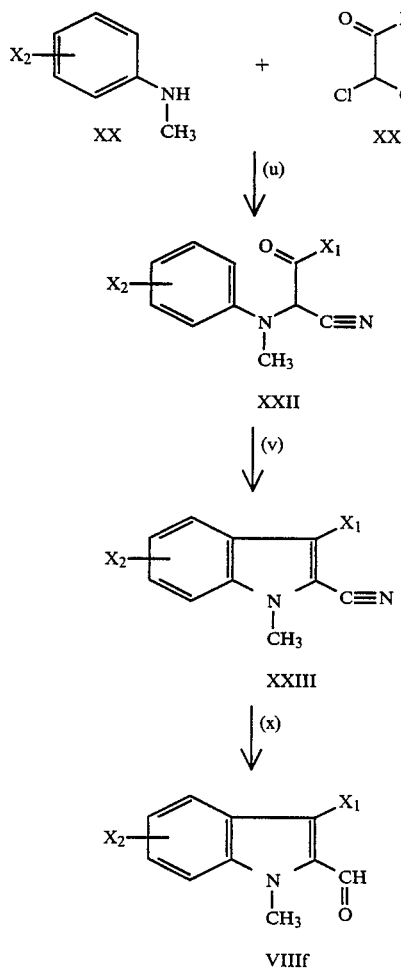

Reaction Scheme XI

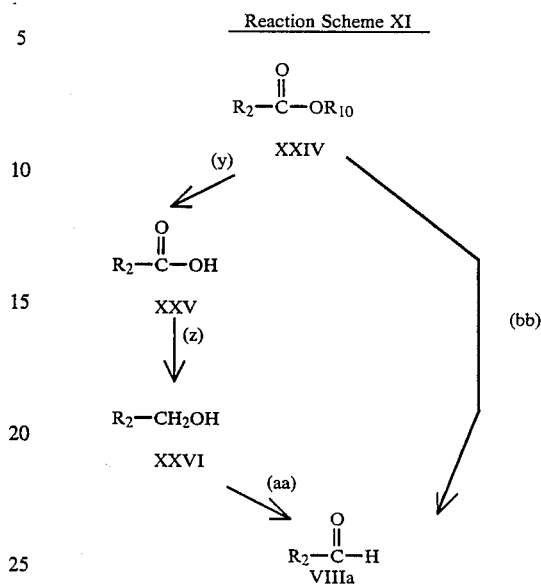

wherein $X_1$ and $X_2$ are as previously described.

In Reaction Scheme X, step (u), an alpha-chloro-betaketonitrile of formula XXI, which are known compounds or can be prepared according to known procedures, is reacted with an N-methylanaline of formula XX, which are known compounds or can be prepared according to known procedures, in an suitable solvent, preferably methanol or ethanol, at a temperature of from 50° C. to the reflux temperature of the solvent. The resulting corresponding compound of formula XXII can be isolated utilizing conventional methods, for example, crystallization, chromatography or the like.

In step (v), a compound of formula XXII is treated with a strong acid, preferably trifluoroacetic acid, at a temperature of from 0° C. to 40° C. to furnish the corresponding compound of formula XXIII which can be isolated utilizing conventional methods, for example, crystallization, chromatography or the like.

In step (x), a nitrile of formula XXIII is reacted with a reducing agent, preferably diisobutylaluminum hydride in an inert solvent, for example, benzene or toluene, at a temperature of from −40° C. to room temperature. The intermediate imine is treated with a dilute solution of a mineral acid, preferably sulfuric acid, and the resulting corresponding carboxaldehydes of formula VIIIf can be isolated utilizing conventional methods, for example, crystallization, chromatography or the like.

wherein $R_2$ and $R_{10}$ are as previously described.

In Reaction Scheme XI, step (y), a carboxylic acid ester of formula XXIV, which are known compounds or can be prepared according to known procedures, is reacted with an excess of alkali metal hydroxide in an solvent mixture, preferably methanol-water or ethanol-water, at a temperature of from room temperature to 85° C. The resulting corresponding carboxylic acid of formula XXV can be isolated utilizing conventional methods, for example, crystallization, chromatography or the like.

In step (z), a carboxylic acid of formula XXV is treated with a reducing agent, for example, borane in tetrahydrofuran, at a temperature of from −10° C. to room temperature. The resulting alcohol of formula XXVI can be isolated utilizing conventional methods, for example, crystallization, chromatography or the like.

In step (aa), an alcohol of formula XXVI is oxidized to a carboxaldehyde of formula VIIIa. A preferred method for this transformation is that described by K. Omura and D. Swern in Tetrahedron 1978, 34, (1651), which involves the reaction of the alcohol with a slight excess of the reagent prepared, as described, from oxalyl chloride and dimethylsulfoxide, in an inert solvent, preferably dichloromethane at a temperature of from −50° C. to −80° C. After the reaction is complete, the mixture is treated with excess triethylamine while the reaction temperature is maintained at from −50° C. to −80° C. Then, after 30 minutes, the reaction is allowed to equilibrate to room temperature. The resulting corresponding carboxaldehyde of formula VIIIa can be isolated utilizing conventional methods, for example, crystallization, chromatography or the like.

In step (bb), the ester of formula XXIV is reacted with a reducing agent, preferably sodium bis(2-methoxyethoxy)-aluminum hydride which has been modified with N-methylpiperazine, in an inert solvent, for example, toluene at a temperature of from −20° C. to room temperature to produce a carboxaldehyde of formula VIIIa that can be isolated utilizing conventional methods, for example, crystallization, chromatography or the like.

Reaction Scheme XII

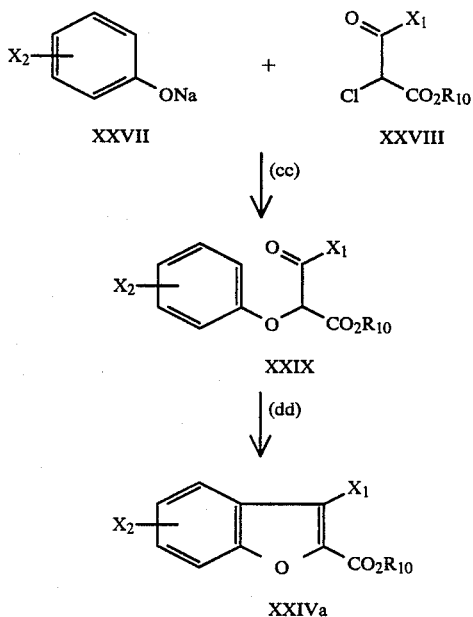

wherein $R_{10}$, $X_1$ and $X_2$ are as previously described.

In Reaction Scheme XII, step (cc), a sodium phenolate of formula XXVII, which are known compounds or can be prepared according to known procedures, is reacted with an alpha-chloro-beta-keto ester of formula XXVIII, which are known compounds or can be prepared according to known procedures, in an inert solvent, for example, benzene or toluene, at a temperature of from 20° C. to 50° C. The resulting corresponding compound of formula XXIX may be isolated utilizing conventional methods, for example, crystallization, chromatography or the like.

In step (dd), a compound of formula XXIX is cyclized by treatment with a strong mineral acid, preferably sulfuric acid, at a temperature of from −40° C. to room temperature. The resulting corresponding benzofurancarboxylic acid ester of formula XXIVa may be isolated utilizing conventional methods, for example, crystallization, chromatography or the like.

Reaction Scheme XIII

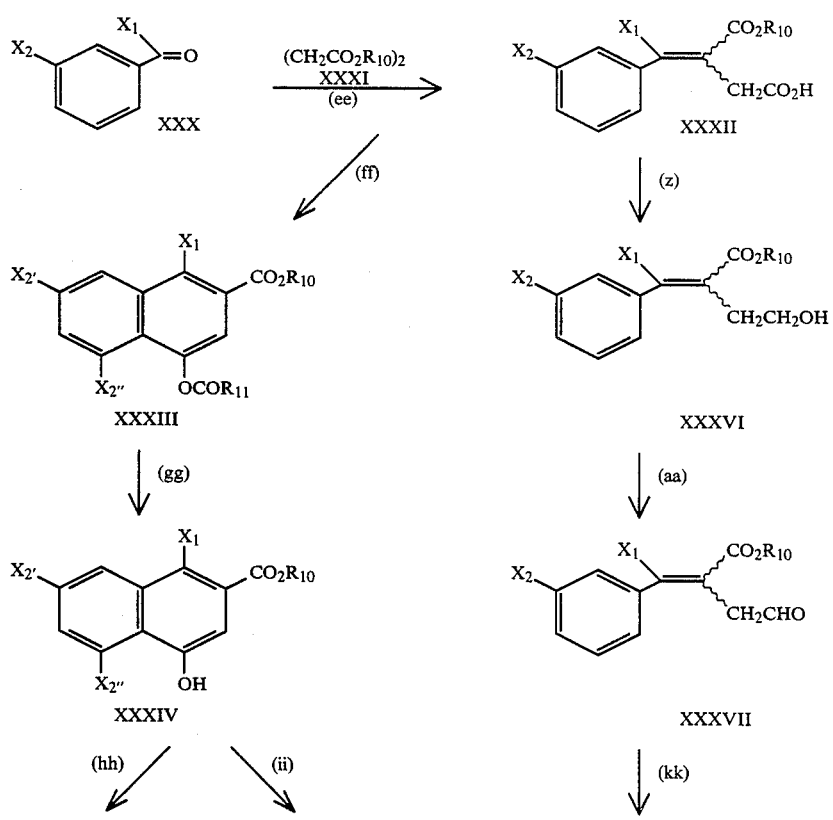

-continued
Reaction Scheme XIII

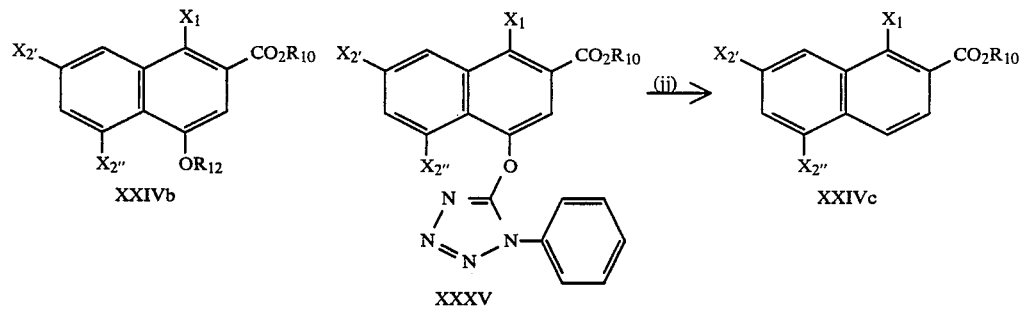

wherein $X_1$ and $X_2$ and $R_{10}$ are as previously described, $R_{11}$ is hydrogen, lower alkyl or trihalomethyl, $R_{12}$ is lower alkoxy and $X_{2'}$ and $X_{2''}$ are as previously described for $X_2$ with the proviso that at least one of $X_{2'}$ or $X_{2''}$ is hydrogen.

In Reaction Scheme XIII, step (ee), a carbonyl compound of formula XXX, which are known compounds or can be prepared according to known procedures, is condensed with a succinic acid diester of formula XXXI, which are known compounds or can be prepared according to known procedures, in a protic solvent, preferably ethanol or t-butanol in the presence of an alkali metal alkoxide, for example, potassium t-butoxide at a temperature of from 50° C. to the reflux temperature of the solvent. The resulting mixture of carboxylic acids of formula XXXII may be isolated utilizing conventional methods, for example, chromatography or the like.

In step (ff), the mixture of acids of formula XXXII is cyclized by treatment with an alkali metal carboxylate, for example, sodium acetate, in a carboxylic acid anhydride, preferably acetic anhydride, at a temperature of from 50° C. to the reflux temperature of the mixture. The resulting isomeric mixture of naphthalenecarboxylic acid esters of formula XXXIII may be separated utilizing conventional methods, for example, chromatography, crystallization or the like.

In step (gg), the carboalkoxy function present in the naphthalenecarboxylic acid esters of formula XXXIII may be selectively hydrolyzed under acidic catalysis, preferably, by using a dilute solution of hydrogen chloride in anhydrous ethanol or methanol, at a temperature of from room temperature to the reflux temperature of the mixture. The resulting 4-hydroxynaphthalenecarboxylic acids esters of formula XXXIV may be isolated utilizing conventional methods, for example, chromatography, crystallization or the like.

In step (hh), a 4-hydroxynaphthalenecarboxylic acids ester of formula XXXIV is reacted with an alkyl halide, for example, methyl iodide, or an arylalkyl halide, for example, benzyl bromide, in an inert solvent such as acetone or dimethylsulfoxide, in the presence of an alkali metal carbonate, preferably potassium carbonate, at a temperature of from room temperature to 60° C. The resulting corresponding compound of formula XXIVb may be isolated utilizing conventional methods, for example, chromatography, crystallization or the like.

In step (ii), a 4-hydroxy-naphthalenecarboxylic acid ester of formula XXXIV is reacted with 5-chloro-1-phenyl-1H-tetrazole, in an inert solvent, preferably, dimethylsulfoxide, in the presence of an alkali metal alkoxide, for example, potassium t-butoxide, at a temperature of from 10° C. to 40° C. The resulting corresponding compound of formula XXXV may be isolated utilizing conventional methods, for example, chromatography, crystallization or the like.

In step (jj), a compound of formula XXXV is hydrogenolyzed over a suitable catalyst, for example, palladium on carbon or platinum oxide, in a suitable solvent, for example, ethanol, or in a mixture of solvents, for example, tetrahydrofuran and ethanol, at a hydrogen pressure of one to three atmospheres until the theoretical amount of hydrogen is taken up to produce a corresponding compound of formula XXIVc that can be isolated utilizing conventional methods, for example, chromatography, crystallization or the like.

In Reaction Scheme XIII, step (z), is the same as step (z) in Reaction Scheme XI to give an alcohol of formula XXXVI which can be isolated utilizing conventional methods, for example, crystallization, chromatography or the like.

In Reaction Scheme XIII, step (aa), is the same as step (aa) in Reaction Scheme XI to give a carboxaldehyde of formula XXXVII which can be isolated utilizing conventional methods, for example, crystallization, chromatography or the like.

In step (kk), a compound of formula XXXVII or a mixture of geometric isomers thereof is treated with a strong acid, preferably trifluoroacetic acid, at a temperature of from 0° C. to 40° C. to furnish the corresponding compound or, if applicable, the mixture of compounds of formula XXIVc which can be isolated and, if applicable, separated utilizing conventional methods, for example, crystallization, chromatography or the like.

Reaction Scheme XIV

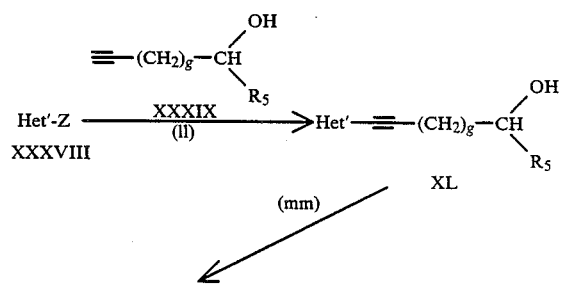

-continued
Reaction Scheme XIV

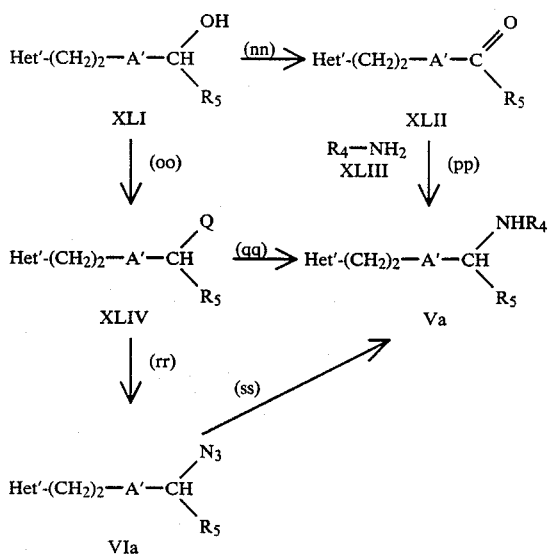

Het'-Z is a 6-membered heteroaromatic radical containing one or two nitrogen atoms which radical may be substituted by halogen, lower alkyl or aryl wherein Z is iodide, bromide, or a perfluoroalkylsulfonate and is substituted in a position on the heteroaromatic ring such that it is active in transition metal catalyzed aryl-alkynyl coupling reactions. The compound of formula XIII becomes attached to Het' at the position of the leaving Z group. Examples of Het' are: 3-pyridinyl, 5-pyrimidinyl, 2-pyridinyl, 6-methyl-3-pyridinyl, 2-methyl-3-pyridinyl and the like. g is an integer of 0 to 4, A' is alkylene of 1 to 4 carbon atoms, Q is bromo, chloro, or an alkyl- or arylsulfonyloxy radical, and $R_4$ and $R_5$ are as previously described.

In Reaction Scheme XIV, step (ll), a compound of formula XXXVIII, which are known compounds or can be prepared according to known methods, is reacted with an acetylene of formula XXXIX in the presence of an excess of a proton acceptor, for example, triethylamine, and a suitable palladium catalyst, for example, bis(triphenylphosphine)palladium dichloride, optionally in the presence of an inert solvent, for example, dichloromethane or dimethylformamide, at a temperature of from room temperature to 100° C., depending on the particular choice of Z-, solvent, and heteroaromatic ring, to give a compound of formula XL. The resulting compound of formula XL can be isolated utilizing conventional methods, for example, distillation, chromatography or the like, or may be used directly in the next step of the synthesis.

In step (mm), an acetylene of formula XL is dissolved in an inert solvent, for example, a lower alkanol, and hydrogenated over a suitable catalyst, for example, palladium on carbon, platinum oxide or the like, at a hydrogen pressure of from one to five atmospheres, preferably at room temperature, until reduction is complete. The resulting compound of formula XLI can be isolated utilizing conventional methods, for example, distillation, chromatography or the like. A compound of formula XLI in which $R_5$ is other than hydrogen may be resolved into its enantiomers using standard methodology, for example, conversion to an ester of a chiral acid and chromatographic separation followed by ester hydrolysis.

In step (oo) an alcohol of formula XLI is reacted with an alkyl or aryl sulfonyl halide, for example, methanesulfonyl chloride or toluenesulfonyl chloride in the presence of a proton acceptor, for example, pyridine or triethylamine to give a compound of formula XLIV wherein Q is an alkyl- or arylsulfonyloxy radical of the same absolute chirality as the starting alcohol XLI. Alternatively, a compound of formula XLI can be reacted with a reagent useful for the conversion of alcohols into halides, for example, thionyl chloride, in the presence of a proton acceptor, for example, pyridine, until conversion to a compound of formula XLIV, Q=Cl or Br, is complete. The resulting compound of formula XLIV generally is not isolated but utilized directly in the next step.

In step (rr), a compound of formula XLIV, is reacted with an alkali metal azide, for example, sodium azide, in the presence of a polar inert solvent, for example, dimethylformamide, N-methylpyrrolidinone, dimethylsulfoxide or the like at a temperature of from about room temperature to 100° C. until azide formation is complete. The resulting compound of formula VIa can be isolated utilizing conventional methods, for example, chromatography or the like. This transformation generally proceeds with inversion of chirality at the carbon atom of a compound of formula XLIV bearing Q.

In step (qq), a compound of formula XLIV is reacted with an amine anion equivalent to give an intermediate which can be deprotected to give an amine of formula Va. For example, a compound of formula XLIV can be reacted with an alkali metal phthalimide, for example, potassium phthalimide, in a polar aprotic solvent, for example, dimethylformamide, dimethyl sulfoxide, N-methylpyrrolidinone, or the like at a temperature of from about 60° to 120° C. until reaction is complete to give an intermediate of formula XLIV, Q=phthalimido, which can be converted to a compound of formula Va, by conventional means, for example, by treatment with hydrazine in a lower alkanol solvent or with methylamine in a polar aprotic solvent such as dimethylformamide. Alternatively, a compound of formula XLIV can be reacted with a perfluoroalkylsulfonamide derived from a primary amine, for example, N-alkyltrifluoromethanesulfonamide, in a polar aprotic solvent, for example, acetone, dimethylformamide, dimethylsulfoxide or the like, in the presence of a base, for example, an alkali metal hydroxide or, as appropriate, an alkali metal hydride, for example, sodium hydride at a temperature of from room temperature to 100° C. The resulting compound of formula Va can be isolated utilizing conventional methods, for example, distillation, crystallization of an acid addition salt, chromatography or the like. When a compound of formula XLIV is chiral, this transformation will generally proceed with inversion of configuration at the carbon atom bearing Q in a compound of formula XLIV.

In step (nn), an alcohol of formula XLI is oxidized to a carbonyl derivative of formula XLII. Reagents which are useful for this transformation include chrominum based oxidizing reagents, for example, pyridinium chlorochromate. A preferable procedure is described in K. Omura and D. Swern, Tetrahedron 1978, 34, 1651, which involves dissolution of a slight excess of an acid halide, for example, oxalyl chloride in an inert halogenated hydrocarbon solvent, for example, dichloromethane, cooling to a reaction temperature of from −50° to −80° C., addition of excess dimethylsulfoxide, stirring for 0.25 to 0.5 hours, addition of one equivalent of an alcohol of formula XLI. After an additional 0.25 to 0.5 hours, addition of excess triethylamine while maintaining the reaction temperature at from −50° to −80° C., and allowing the reaction mixture to warm for 0.5 to 1 hour before quenching with water and excess inorganic base to produce a carbonyl derivative of formula XLII.

In step (pp), a carbonyl derivative of formula XLII is reacted with an amine of formula XLIII, which are known compounds or can be prepared according to known procedures, to form a Schiff's base which is reduced in the presence of an appropriate reducing agent to produce a corresponding amine of formula Va in either a one step or two step process. For example, a compound of formula XLII is treated with a large excess of an amine of formula XLIII and an equivalent amount of a weak organic acid, for example, acetic acid, in the presence of a reducing agent such as sodium cyanoborohydride in a suitable solvent, preferably a lower alkanol, for example, methanol, at room temperature until the starting material is consumed.

Alternatively, an amine of formula XLIII and a carbonyl derivative of formula XLII heated together in aromatic solvent in an apparatus fitted with a water separator until water formation is complete. The resulting Schiff's base can be hydrogenated over a suitable catalyst, preferably Raney nickel, at a hydrogen pressure of from one to five atmospheres to give a compound of formula Va. When $R_5$ is not hydrogen and $R_4$ is chiral, the resulting amine Va may be enriched in one diastereomer over the other. For example, when $R_4$ is a chiral benzyl group, for example, R-alpha-methylbenzyl, and $R_5$ is lower alkyl, for example, methyl, the compound of formula Va may be diastereomerically enriched, and the chiral benzyl moiety may be removed, for example by hydrogenation over palladium on carbon to give an enantiomerically enriched amine of formula Va, $R_4$=hydrogen and $R_5$=lower alkyl. A resulting compound of formula Va can be isolated utilizing conventional methods, for example, extraction followed by distillation, crystallization of an acid addition salt, chromatography or the like.

In Reaction Scheme XIV, step (ss), an azide of formula VIa is dissolved in a solvent, preferably, a lower alkanol, and hydrogenated at a hydrogen pressure of from one to five atmospheres over a nobel metal catalyst, for example, palladium on carbon or platinum oxide. The resulting compound of formula Va can be isolated utilizing conventional methods, for example, distillation, crystallization of an acid addition salt, chromatography or the like. This transformation proceeds without alteration of the chirality of the carbon atom bearing the azido group in a compound of formula VIa.

Reaction Scheme XV

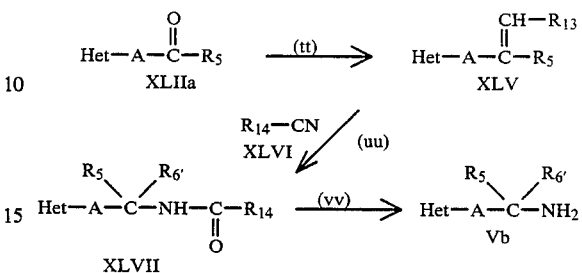

wherein Het, A and $R_5$ are as previously described. $R_6$, is alkyl, $R_{13}$ is hydrogen or lower alkyl, and $R_{14}$ is alkyl, aryl or alkylaryl.

In Reaction Scheme XV, step (tt), a carbonyl derivative of formula XLIIa, which are known compounds or can be prepared according to known methods, is treated with an alkylidene triarylphosphorane in an inert solvent, preferably tetrahydrofuran, dimethylsulfoxide or diethyl ether, at a temperature of from −80° C. to room temperature. The resulting corresponding compound of formula XLV can be isolated utilizing conventional methods, for example, distillation, chromatography or the like.

In step (uu), a nitrile of formula XLVI is reacted with a compound of formula XLV in the presence of a strong mineral acid, preferably sulfuric acid and a small amount of water. The resulting corresponding compound of formula XLVII can be isolated utilizing conventional methods, for example, distillation, crystallization, chromatography or the like.

In step (vv), a compound of formula XLVII is hydrolyzed to a corresponding amine of formula Vb. The hydrolysis is advantageously carried out, when $R_{14}$ is 2-nitrobenzyl, by catalytic reduction of the nitrobenzyl group, for example, over palladium on carbon at one atmosphere hydrogen pressure, and heating of the residue in the absence of solvent or in the presence of a solvent, for example, acetic acid. The resulting corresponding compound of formula Vb can be isolated utilizing conventional methods, for example, distillation, crystallization of an acid addition salt, chromatography or the like.

Reaction Scheme XVI

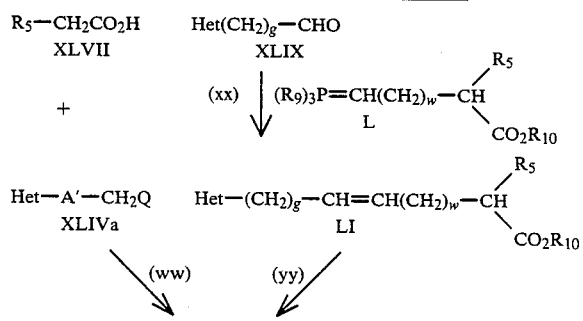

Reaction Scheme XVI

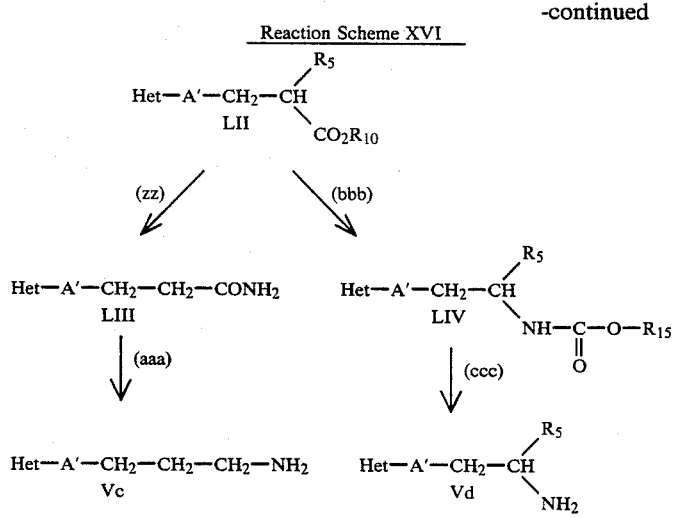

wherein Het, $R_5$, $R_9$, $A'$, Q and g are as previously described, and $R_{10}$ is hydrogen or lower alkyl, $R_{15}$ is alkyl or aryl, and w is an integer of 0 to 3.

In Reaction Scheme XVI, step (ww), the dilithium salt derived from a compound of formula XLVIII, which are known compounds or can be prepared according to known methods, for example, by treatment with lithium diisopropylamide, is reacted with a compound of formula XLIVa, which are known compounds or can be prepared according to known methods, in a suitable inert solvent, for example, tetrahydrofuran, to give the corresponding compound of formula LII, $R_{10}$=hydrogen. A resulting compound of formula LII can be isolated utilizing conventional methods, for example, crystallization, chromatography or the like.

A compound of formula LII, in which $R_5$ is non-hydrogen, and $R_{10}$ is hydrogen, may be resolved into its enantiomers by conversion to salts of chiral, enantiomerically pure amines, for example, cinchonine, brucine, alpha-methylbenzylamine or the like. The pure diastereomeric salts are obtained by fractional crystallization from an appropriate solvent, for example, a lower alkanol. A chiral, enantiomerically pure acid of formula LII, $R_{10}$=hydrogen, may be recovered from its salts by conventional means, for example extraction from an aqueous, acidic solution.

In step (xx), a heteroaromatic carboxaldehyde of formula XLIX, which are known compounds or can be prepared according to known methods, is reacted with a (carboxyakylidene)triarylphosphorane of formula L, which are known compounds or can be prepared according to known methods, in a suitable solvent, for example, tetrahydrofuran, dichloromethane, methanol or dimethylsulfoxide, to give a compound of formula LI. A resulting compound of formula LI can be isolated utilizing conventional methods, for example, crystallization, distillation, chromatography or the like.

In step (yy), a compound of formula LI is hydrogenated over a suitable catalyst, for example, palladium on carbon or platinum oxide, in a suitable solvent, for example, a lower alkanol, at a hydrogen pressure of from one to five atmospheres until the theoretical amount of hydrogen is taken up to give a corresponding compound of formula LII.

In step (zz), a compound of formula LII is converted into an amide of formula LIII using conventional techniques for the conversion of carboxylic acids and esters into the corresponding primary amide. For example, a compound of formula LII, $R_{10}$=hydrogen may be converted to the corresponding acid chloride by treatment with thionyl chloride and then retreating with an excess of ammonia to give a corresponding compound of formula LIII. Alternatively, a compound of formula LII, $R_{10}$=lower alkyl, may be converted into a corresponding compound of formula LIII by treatment with excess ammonia, optionally in the presence of co-solvent, for example, a lower alkanol, at a temperature of from $-33°$ C. to room temperature. The reaction may be run in a pressure vessel, when appropriate.

In step (aaa), a compound of formula LIII is treated with a reducing agent, for example, borane in tetrahydrofuran at a temperature of from room temperature to the reflux temperature of the solvent for 4 to 24 hours or until reduction is complete to give a corresponding compound of formula Vc. A resulting compound of formula Vc can be isolated utilizing conventional methods, for example, by destruction of the excess reagent with a lower alkanol, followed by treatment with a mineral acid, for example, hydrochloric acid, basification, evaporation of the solvent and extraction of the product into a suitable organic solvent, for example, dichloromethane and purified by distillation, chromatography or the like.

In step (bbb), an acid of formula LII, $R_{10}$=hydrogen, which may be obtained from the corresponding ester by hydrolysis, is subjected to conditions leading to a Curtius rearrangement in the presence of a lower alkanol. In a preferred procedure, an acid of formula LII ($R_{10}$=hydrogen), is treated with one equivalent of diphenylphosphoryl azide in the presence of a proton acceptor, for example, triethylamine or the like, and an excess of a lower alkanol or a phenol to give a corresponding compound of formula LIV. A resulting compound of formula LIV can be isolated utilizing conventional methods, for example, crystallization, chromatography or the like.

In step (ccc), a compound of formula LIV is treated with an excess of a mineral acid in water and optionally a co-solvent, for example, a lower alkanol, at a temperature of from room temperature to 100° C. or with a strong base in water, optionally in the presence of a co-solvent, for example, a lower alkanol at a temperature of between 60° C. and 100° C. to form a compound of formula Vd. A resulting compound of formula Vd can be isolated utilizing conventional methods, for example, crystallization of their acid addition salts, distillation, chromatography or the like.

Reaction Scheme XVII

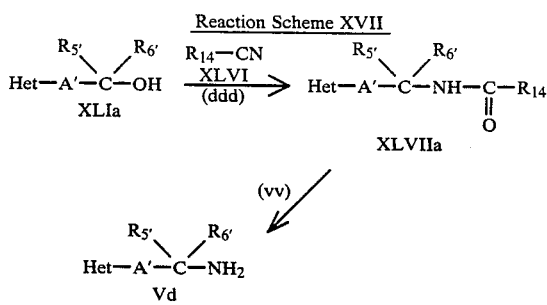

wherein Het, A′, R$_6$, and R$_{14}$, are as previously described, and R$_5$, is lower alkyl.

In Reaction Scheme XVII, step (ddd), an alcohol of formula XLIa is reacted with a nitrile of formula XLVI in the presence of a mineral acid, for example, sulfuric acid, and water at a temperature of from −20° C. to room temperature to give a compound of formula XLVIIa. A resulting compound of formula XLVIIa can be isolated by conventional means, for example chromatography, crystallization or the like.

In Reaction Scheme XVII, step (vv) is the same as step (tt) in Reaction Scheme XV to give a compound of formula Vd which can be isolated by conventional means, for example, chromatography, crystallization or its acid addition salts, distillation or the like.

Reaction Scheme XVIII

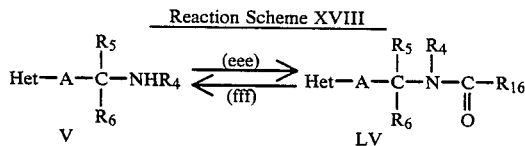

wherein Het, A, R$_4$, R$_5$ and R$_6$ are as previously described, R$_{16}$ is a chiral moiety, for example, a bonded chain lower alkyl or lower alkyl substituted with one or two groups selected from hydroxy, lower alkoxy, lower alkylcarbonyloxy, trifluoromethyl or aryl.

In Reaction Scheme XVIII, step (eee), compounds of formula V which are chiral may be resolved into their enantiomers by conversion to amides of chiral, enantiomerically pure acids using common techniques of peptide coupling. For example, a chiral amine of formula V may be coupled with a chiral, enantiomerically pure acid, for example, (R)-mandelic acid, in the presence of a suitable coupling reagent, for example, dicyclohexylcarbodiimide optionally in the presence of a promoter, for example, 1-hydroxybenzotriazole in a polar, aprotic solvent, for example, dimethylformamide to give a corresponding amide of formula LVI. Amides of formula LVI may be separated into pure diastereomers by fractional crystallization, chromatography or the like.

In step (fff), enantiomerically pure compounds of formula V may be recovered by hydrolysis of diastereomerically pure amides of formula LV, for example with an aqueous mineral acid at a temperature of from 60° C. to 120° C.

The compounds of formula I can form acid addition salts with inorganic or organic acids. Thus, they form pharmaceutically acceptable acid addition salts with both pharmaceutically acceptable organic and inorganic acids, for example, with hydrohalic acids, such as, hydrochloric acid, hydrobromic acid, hydroiodic acid, other mineral acid salts, such as, sulfuric acid, nitric acid, phosphoric acid, perchloric acid or the like, alkyl and mono-aryl sulfonic acids such as, ethanesulfonic acid, toluenesulfonic acid, benzenesulfonic acid, or the like, other organic acids such as tartaric acid, maleic acid, citric acid, salicylic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

The useful activity of the compounds of formula I can be demonstrated by the following procedures:

Binding Assay (a) Assay

The binding assay was done in 400 μl polyethylene microcentrifuge tubes (Beckman) containing 50 μl of an oil mixture of 2 parts Siliconol AR200 (Serva): 1 part Silicone Fluid (Arthur H. Thomas). Buffer, standards, or analogs (150 μl total volume) were added to the tubes. Radiolabelled $^3$H-PAF (50 μl) was then added to the tubes. The reaction was started by the addition of 50 μl of dog platelets (2×10$^7$ platelets). The tubes were capped, inverted several times to mix, and incubated for 10 minutes at room temperature. The platelets were separated from the incubation mixture by centrifuging 1 minute in a Beckman Microfuge B centrifuge. The tip of the microfuge tube was cut off, and the platelets were washed out of the tip with 200 μl of 50% methanol (Burdick and Jackson). Aquasol (NEN, 10 ml) was added and the radioactivity in the samples was determined using an LS 8100 Beckman liquid scintillation counter linked to a Techtran tape recorder. Data was processed through an in-house computer system. Alternatively, radioactivity was determined using a Searle Mark III liquid scintillation counter linked to a Iso-Data microprocessor. Results are set forth in Table I.

(b) Preparation of Platelets

Blood was collected from anesthesized or unanesthesized dogs into 50 ml plastic centrifuge tubes containing 3.8% sodium citrate as the anticoagulant (1 volume of citrate/9 volumes of blood). The red cells were removed by centrifugation for 15 minutes at 600 rpm (100–125 g) at room temperature. An aliquot of the supernatant platelet rich plasma (PRP) was saved for cell counting and the remainder was acidified to pH 6.5 with 0.15M citric acid. The platelet pellet was obtained after a 10 minute centrifugation at 2000 rpm (1000 g) at room temperature. Washed platelets were prepared by resuspending the platelet pellet once with PBS containing 1 mM EDTA, centrifuging as noted, and then resuspending the platelets in 0.1% BSA-PBS. An aliquot of the washed platelets was counted. Platelets used for binding assays were diluted to $2\times 10^7$ platelets/assay tube ($4\times 10^8$ platelets/ml). Platelet counting was done using a Royco Cell-Crit 921.

PAF Induced Bronchoconstriction Assay

Male animals (Hartlet Strain, 400–500 g) were anesthetized with urethane (2 g/kg, i.p.). Each animals' trachea was cannulated and the guinea pigs were respirated using a Harvard small animal rodent respirator (3.0 cc stroke volume, 40 breaths per min.). Tracheal pressure was recorded from a cannula inserted in the trachea and connected to a Statham Pressure Transducer.

The jugular vein was cannulated for administering compounds. Spontaneous breathing was arrested with succinylcholine (1.2 mg/kg, i.v.) administered 2 minutes prior to intravenous injection of platelet activating factor (PAF). Since propranolol has been shown to enhance bronchoconstrictor responses, all animals were pretreated five minutes prior to challenge with propranolol (0.1 mg/kg, i.v.).

For, the intravenous testing, the guinea pig is given a 5-minute pretreatment with propranolol at a dose of 0.1 mg/kg intravenously. The test compound is administered with a 1 minute pretreatment prior to intravenous challenge with PAF. The animal is than challenged with a 1.0 µg/kg intravenous dose of PAF and the change is tracheal pressure is measured.

For the oral testing, the procedure includes a 2-hour pretreatment period with the test compound administered through an oral gavage tube. Propranolol or succinylcholine and PAF are administered intravenously, and the change in tracheal pressure measured.

The change in tracheal pressure is determined by subtracting the steady state baseline achieved after administration of succinylcholine from the peak bronchoconstriction seen after challenge with PAF. The mean is calculated for each test compound and compared to the mean of the control animals to give the percent inhibition of bronchoconstriction. The standard error is calculated as the standard error of the mean.

The compounds of formula I also have Thromboxane Synthase ($TXA_2Syn.$) Inhibitory Activity, which can be demonstrated as follows.

$TXA_2$ Synthesis Inhibition

Thromboxane Synthase inhibitory $TAX_2$ syn. activity is measured by following the conversion of $^{14}C$-thromboxane $A_2$ ($TXA_2$) using microsomal fractions from human platelets as enzyme source. In the aqueous incubation medium, the $TAX_2$ decomposes rapidly into $TXB_2$. The amount of $TXA_2$ syn. is adjusted so that under the conditions of the assay approximately 80–90% of the substrate, $PGH_2$, is converted to product in control tubes. To prepare $^{14}C$-$PGH_2$, $^{14}C$-AA(50–60 mCi/mmole; (Rose Chem.) is incubated with sheep seminal vesicular gland microsomes for 1.5 min. at 37° and then the $^{14}C$-$PGH_2$ is extracted with diethylether, purified on columns of Sephadex LH-20 or silicic acid, and stored in acetone at $-70°$ C. Incubations are done as follows. Sufficient $^{14}C$-$PGH_2$ to yield a final substrate concentration of 10 µM ($\sim$30,000 cpm) is added to the incubation tubes and then the acetone is removed under nitrogen. The tubes are placed in an ice bath and then 215 µl of ice cold phosphate buffered saline, 10 µl of ethanol (control) or of test drug in ethanol, and 25 µl of the microsomal suspension are added with mixing in that order as rapidly as possible. The tubes are incubated at 22° for 2 minutes, the reaction is stopped and then the radioactive products and the unconverted $PGH_2$ are extracted and analyzed by thin layer chromatography. The amount of $^{14}C$-$PGH_2$ converted to products is analyzed by thin layer chromatography. The amount of $^{14}C$-$PGH_2$ converted to products was used as a measure of $TXA_2$ synthase activity. Inhibitors were tested initially at a concentration of 100 µM. $IC_{50}$ values were calculated by linear regression analysis of successive 10 fold dilutions of the test compound concentration.

Test results obtained with compounds of formula I in the described tests are set forth in Table I which follows:

TABLE 1

| | INHIBITION OF PAF INDUCED BRONCHOCONSTRICTION | | | | | |
|---|---|---|---|---|---|---|
| COMPOUND | Inh. of PAF Binding $IC_{50}$(nM) | Bronchoconstriction 1 mg/kg, iv | $ID_{50}$, iv mg/kg | % Inh. (2 hr. pretreatment 50 mg/kg, po | $ID_{50}$, PO[a] mg/kg | % Inh. (6 hr. pretreatment) 50 mg/kg, po |
| (E)-3-(1-Butyl-4-methoxy-2-naphthalenyl)-N-[6-(5-pyrimidinyl)hexyl]-2-propenamide | — | — | | | | |
| (E)-3-[7-Methoxy-1-(3-methoxyphenyl) 2-naphthalenyl]-N-[4-(3-pyridinyl) butyl]-2-propenamide | 8 | 62 ± 8% | | | | |
| [R-(E)]-3-(6-Methoxy-3-pentylinden-2-yl)-N-[1-methyl-4-(3-pyridinyl) butyl]-2-propenamide | 33 | 96 ± 1% | | | | |
| [R-(E)]-3-(6-Methoxy-3-pentylbenzo-[b]thien-2-yl)-N-[1-methyl-4-(3-pyridinyl)butyl]-2-propenamide | 24 | 98 ± 1% | | | | |
| [R-(E)-3-(6-Methoxy-3-pentylbenzo-furan-2-yl)-N-[1-methyl-4-(3-pyridinyl)butyl]-2-propenamide | 40 | 86 ± 9% | | | | |
| [R-(E)]-3-(6-Methoxy-1-methyl-3-pentylindol-2-yl)-N-[1-ethyl-4-(3-pyridinyl)butyl]-2-propenamide. | — | — | | | | |
| [R-(E)]-3-[3,4-Dihydro-6-methoxy-1-(4-methoxyphenyl)-2-naphthalenyl]-N-[1-methyl-4-(3-pyridinyl)butyl]-2-propenamide | 30 | 95 ± 2% | 0.15 | 75 ± 2 | 17.0 | 1 ± 10 |
| [R-(E)]-3-[6-Methoxy-1-(4-methoxyphenyl)-2-naphthalenyl]-N-[1-methyl-4-(3-pyridinyl)butyl]-2-propenamide | 55 | 92 ± 3% | 0.18 | 79 ± 2 | 12.0 | 55 ± 19 |
| [R-(E)]-3-(1-Butyl-5-methoxy-2-naphthalenyl)-N-[1-methyl-4-(3- | 6 | 50 ± 12% | | | | |

TABLE 1-continued

INHIBITION OF PAF INDUCED BRONCHOCONSTRICTION

| COMPOUND | Inh. of PAF Binding $IC_{50}$(nM) | Bronchoconstriction 1 mg/kg, iv | $ID_{50}$, iv mg/kg | % Inh. (2 hr. pretreatment) 50 mg/kg, po | $ID_{50}$, $PO^a$ mg/kg | % Inh. (6 hr. pretreatment) 50 mg/kg, po |
|---|---|---|---|---|---|---|
| pyridinyl)butyl]-2-propenamide | | | | | | |
| [R-(E)]-3-(1-Butyl-7-methoxy-2-naphthalenyl)-N-[1-methyl-4-(3-pyridinyl)butyl]-2-propenamide | 15 | | | | | |
| [R-(E)]-3-(1-Butyl-4,7-dimethoxy-2-naphthalenyl)-N-[1-methyl-4-(3-pyridinyl)butyl]-2-propenamide | 3 | 80 ± 12% | 0.44 | 16 ± 8 | | |
| [R-(E)]-3-(1-Butyl-4-methoxy-2-naphthalenyl)-N-[1-methyl-4-(3-pyridinyl)butyl]-2-propenamide | 1 | 90 ± 5% | 0.11 | 95 ± 2 | | 52 ± 15 |
| 9,9-Diphenyl-N-[4-(3-pyridinyl)-butyl]-7-octenamide | 1000 | — | | | | |
| 9,9-Diphenyl-N-[4-(3-pyridinyl)-butyl]-8-nonenamide | 1000 | — | | | | |
| N-(5,5-Diphenyl-4-pentenyl)-3-pyridine-butanamine (1:1) (E)-2-butenedioate salt | 120 | — | | | | |
| N-(5,5-diphenyl-4-pentenyl)-N-[4-(3-pyridinyl)-butyl]formamide | 1000 | — | | | | |
| N-(5,5-diphenyl-4-pentenyl)-N-methyl-3-pyridinebutanamine (1:1) ethanedioate 0.25 molar ate | 560 | — | | | | |
| [R-(E)]-3-(1-Butyl-6-methoxy-2-naphthalenyl)-N-[1-methyl-4-(3-pyridinyl)butyl]-2-propenamide | 7 | 95 ± 1% 0.45 | 0.45 | 92 ± 3 | 4.2 | 71 ± 10 |
| [R-(E)]-3-(1-Butyl-3,4-dihydro-6-methoxy-2-naphthalenyl)-N-[1-methyl-4-(3-pyridinyl)butyl]-2-propenamide | 90 | 94 ± 2% | | 50 ± 6 | | |
| 3,3-Diphenyl-N-[4-(3-pyridinyl)-butyl]-2-propenamide | 450 | — | | | | |
| 3,3-Diphenyl-N-[6-(3-pyridinyl)-hexyl]-2-propenamide | 1000 | — | | | | |
| 4,4-Diphenyl-N-[4-(3-pyridinyl)-butyl]-3-butenamide | 1000 | — | | | | |
| 5,5-Diphenyl-N-[4-(3-pyridinyl)-butyl]-4-pentenamide | 120 | — | | | | |
| 5,5-bis(4-Methoxyphenyl)-N-[4-(3-pyridinyl)-butyl]-4-pentenamide | 200 | — | | | | |
| 5,5-bis(4-Fluorophenyl)-N-[4-(3-pyridinyl)-butyl]-4-pentenamide | 350 | — | | | | |
| N-[4-(1H-Imidazol-1-yl)butyl]-5,5-diphenyl-4-pentenamide | 1000 | — | | | | |
| 6,6-Diphenyl-N-[4-(3-pyridinyl)-butyl]-5-hexenamide | 1000 | — | | | | |
| 7,7-Diphenyl-N-[4-(3-pyridinyl)-butyl]-6-heptenamide | 550 | — | | | | |

$a$ = 2 hour pretreatment time

TABLE II

| Compound | Inhibition of $TXA_2$ Synthetase $IC_{50}$ (μM) |
|---|---|
| 3,3-Diphenyl-N-[4-(3-pyridinyl)butyl]-2-propenamide | 0.1–1 |
| 4,4-Diphenyl-N-[4-(3-pyridinyl)butyl]-3-butenamide | 1 |
| 5,5-Diphenyl-N-[4-(3-pyridinyl)butyl]-4-pentenamide | 0.1–1 |
| 5,5-bis(4-Methoxyphenyl)-N-[4-(3-pyridinyl)butyl]-4-pentenamide | 1–10 |
| 5,5-bis(4-Fluorophenyl)-N-[4-(3-pyridinyl)butyl]-4-pentenamide | 1–10 |
| 6,6-diphenyl-N-[4-(3-pyridinyl)butyl]-5-hexenamide | 0.1 |
| 7,7-Diphenyl-N-[4-(3-pyridinyl)butyl]-6-heptenamide | 0.1–10 |
| 8,8-Diphenyl-N-[4-(3-pyridinyl)butyl]-7-octenamide | 0.1–1 |
| 9,9-Diphenyl-N-[4-(3-pyridinyl)butyl]-8-nonenamide | 0.01–0.1 |

A compound of formula I, an enantiomer thereof or a salt thereof or a composition containing a therapeutically effective amount of a compound of formula I, an enantiomer thereof or a salt thereof can be administered by methods well known in the art. Thus, a compound of formula I, an enantiomer thereof or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

The geometric isomers encompassed by formula I can be separated by conventional means, for example, chromatography, crystallization and the like. It is noted, however, that the separation in most instances is done at a earlier stage in the synthesis of the compounds of formula I.

Furthermore, since compounds of formula I of the invention, when $R_5$ and $R_6$ are different, possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent, for example, an optically active acid, such as dibenzoyltartaric acid. The formed diastereomers are separated by selective crystallization and converted to the corresponding optical isomer. Thus, the invention covers the racemates of the compounds of formula I as well as their optically active isomers (enantiomers).

The example which follow also further describe the invention. All temperatures given are in degree centigrade unless otherwise stated.

EXAMPLE 1

(R,S)-alpha-Methyl-4-(3-pyridinyl)-3-butyn-1-ol

In an inert atmosphere, 26 g of bis(triphenylphosphine) palladium dichloride and 2.28 g of cuprous iodide were added to a stirred solution of 311.2 g of (R,S)-4-pentyn-2-ol, 556.8 g of 3-bromopyridine and 665 mL of triethylamine in 1.8 L of dichloromethane at ambient temperature. After stirring for 75 minutes, the mildly exothermic reaction reached reflux temperature, and when the gentle boiling had subsided (40 minutes), external heat was applied to maintain reflux for 5 additional hours. The cooled reaction was stirred overnight at room temperature, then 1 L of water and 500 g of ice were added, followed by 420 mL of conc. hydrochloric acid (HCl) and the stirring was continued for several minutes. After the phases were separated, the aqueous layer was extracted with dichloromethane (4×1 L) and then the organic layers were backwashed with 1 L of 1N HCl before being discarded. The original aqueous phase was treated with 500 mL of 10N sodium hydroxide (NaOH) and the second aqueous layer was basified with 200 mL of 10N NaOH before each was extracted in turn with dichloromethane (1×2 L; 3×1 L). The combined organic extracts were dried over potassium carbonate ($K_2CO_3$) and evaporated to constant weight under reduced pressure to yield 477.3 g of crude (R,S)-alpha-methyl-4-(3-pyridinyl)-3-butyn-1-ol as an amber oil.

EXAMPLE 2

Preparation of (R,S)-alpha-methyl-4-pyridinebutanol

The crude (R,S)-alpha-methyl-4-(3-pyridinyl)-3-butyn-1-ol (477.3 g) obtained in the previous Example was hydrogenated over 20 g of platinum oxide in 3.5 L of ethanol at room temperature and atmospheric pressure. After the uptake of hydrogen had stopped, the catalyst was filtered and the solvent was removed under reduced pressure. The residual oil was distilled on a Kugelrohr apparatus (115°-120° C./0.1 mm) to yield 420.5 g of (R,S)-alpha-methyl-3-pyridinebutanol.

EXAMPLE 3

Preparation of 5-(3-pyridinyl)-2-pentanone

A stirred solution of 218.6 g of oxalyl chloride in 1.5 L of dry dichloromethane was cooled to −75° C. under argon, then a mixture of 141 g of dry dimethylsulfoxide in 200 mL of dichloromethane was added dropwise over 75 minutes such that the reaction temperature did not exceed −72° C. The mixture was stirred at −75° C. for 10 minutes, then a solution of 271.5 g of (R,S)-alpha-methyl-3-pyridinebutanol in 125 mL of dichloromethane was added dropwise over 55 minutes, while the reaction temperature was maintained below −70° C. After the addition of substrate was completed, the mixture was stirred at −75° C. for another 30 minutes, then 520 mL of triethylamine was added over 65 minutes while the reaction temperature was maintained between −65° and −70° C. The cooling bath was removed, and after the reaction was allowed to equilibrate to room temperature over 1 hour, 1 L of water was added and the phases separated. The aqueous layer was extracted with dichloromethane (2×800 mL), and then the organic phase and extracts were washed in turn with 800 mL of 1.5N NaOH and with 800 mL of 10% sodium chloride (NaCl). The combined organic layers were dried ($K_2CO_3$) and evaporated to yield 266 g of crude ketone. The product was distilled to yield 248.6 g of 5-(3-pyridinyl)-2-pentanone (bp 100°-102° C./0.2 mm).

EXAMPLE 4

Preparation of (R,S)-methanesulfonic acid 5-(3-pyridinyl)-2-pentyl ester

In an inert atmosphere, a solution of 2.42 mL of methanesulfonyl chloride in 10 mL of dichloromethane was added over 10 minutes to a stirred mixture of 5.0 g of (R,S)-alpha-methyl-3-pyridinebutanol and 6.2 mL of triethylamine in 50 mL of dry dichloromethane maintained at −40° C. After 30 minutes the reaction was warmed to 0° C. then a small piece of ice was added and the mixture was stirred in a an ice bath for another 15 minutes. The solution was then washed in turn with water (3×15 mL), 1N NaOH (2×15 mL) and brine (10 mL). The dried (K₂CO₃) organic layer was evaporated to furnish 7.2 g of (R,S)-methanesulfonic acid 5-(3-pyridinyl)-2-pentyl ester.

EXAMPLE 5

Preparation of (R,S)-3-(4-azidopentyl)pyridine.

A mixture of 2.5 g of (R,S)-methanesulfonic acid 5-(3-pyridinyl)-2-pentyl ester, 0.832 g of sodium azide, 1.5 mL of water and 15 mL of dimethylformamide was stirred at 50° C. under argon for 150 minutes. The cooled solution was diluted with 40 mL of water and extracted with dichloromethane (3×30 mL). The extracts were washed in turn with water (2×20 mL) and then were combined, dried (K₂CO₃) and evaporated to furnish 1.76 g of (R,S)-3-(4-azidopentyl)pyridine as an oil.

EXAMPLE 6

Preparation of (R,S)-3-(ethoxycarbonyl)butyltriphenylphosphonium bromide.

A solution of 86.3 g of (R,S)-4-bromo-2-methylbutanoic acid ethyl ester and 104.9 g of triphenylphosphine in 600 mL of toluene was stirred at reflux for 4 days. As the reaction proceeded, the phosphonium bromide separated from solution as an oil. After the reaction was cooled, the toluene supernatant was decanted and replaced with 500 mL of fresh toluene. The mixture was stirred at reflux for 30 minutes, then was cooled and the toluene layer was again decanted. After this process was repeated a second time, the residual oil was dried in vacuo to give 187 g of (R,S)-3-(ethoxycarbonyl)butyltriphenylphosphonium bromide as a viscous oil.

EXAMPLE 7

Preparation of [(R,S)-Z]-2-methyl-5-(3-pyridinyl)-4-pentenoic acid ethyl ester

A stirred solution of 10.56 g of sodium hydride (60% dispersion in oil) in 1000 mL of dry dimethylsulfoxide was heated at 70° C. until the evolution of hydrogen stopped (30 minutes), then the solution was cooled to 0° C. and a solution of 103.7 g of (R,S)-3-(ethoxycarbonyl)butyltriphenylphosphonium bromide in 200 mL dimethylsulfoxide was added. After the mixture had stirred at room temperature for 30 minutes, a solution of 20.8 mL of 3-pyridinecarboxaldehyde in 100 mL of tetrahydrofuran was added and the reaction was stirred at room temperature overnight. The mixture was diluted with ice-water and extracted with dichloromethane (6×150 mL). The combined organic layers were then extracted with 4×400 mL of 0.5N HCl. The acidic layers were made basic with 125 mL triethylamine and extracted with dichloromethane (5×150 mL), and the dried (K₂CO₃) extracts were evaporated to furnish 34 g of crude reaction product. An initial purification of the material by high pressure liquid chromatography (HPLC) (ether-hexane; 3:2) yielded 11.9 g of a mixture of (Z)-and (E)-isomers (4:1). A subsequent separation of the mixture by HPLC with recycle gave 6.77 g of [(R,S)-Z]-2-methyl-5-(3-pyridinyl)-4-pentenoic acid ethyl ester and 3 g of a mixture of [(R,S)-Z]-2-methyl-5-(3-pyridinyl)-4-pentenoic acid ethyl ester and its (E)-isomer.

EXAMPLE 8

Preparation of (R,S)-alpha-methyl-3-pyridinepentanoic acid ethyl ester

A solution of 5.5 g of a mixture (1:1) of [(R,S)-E]-and [(R,S)-Z]-2-methyl-5-(3-pyridinyl)-4-pentenoic acid ethyl ester in 100 mL was ethanol was hydrogenated over 0.4 g of 10% palladium on carbon (Pd/C). After the uptake of hydrogen had stopped, the catalyst was removed by filtration and the solvent evaporated to give 5.33 g of (R,S)-alpha-methyl-3-pyridinepentanoic acid ethyl ester.

EXAMPLE 9

Preparation of (R,S)-alpha-methyl-3-pyridinepentanoic acid

A mixture of 5.3 g of (R,S)-alpha-methyl-3-pyridinepentanoic acid ethy ester, 35 mL of 1N NaOH and 35 mL of methanol was stirred at reflux for 3 hours, then most of the methanol was removed under reduced pressure. The solution was diluted to 100 mL with water and extracted with dichloromethane (3×35 mL). The aqueous layer was then neutralized with 35 ml of 1N HCl and extracted with dichloromethane (3×30 mL), then dried over sodium sulfate (Na₂SO₄). Extracts were evaporated to yield 3.47 g of (R,S)-alpha-methyl-3-pyridinepentanoic acid.

EXAMPLE 10

Preparation of (R,S)-[1-methyl-4-(3-pyridinyl)butyl]carbamic acid 1,1-dimethylethyl ester.

As in Example 36, 1.93 g of (R,S)-alpha-methyl-3-pyridinepentanoic acid when treated with 2.21 mL of diphenylphosphorylazide in 10 mL of t-butanol containing 1.4 mL of triethylamine furnished 2.45 g of crude product. Purification of the material by HPLC (ethyl acetate) yielded 2.2 g of (R,S)-[1-methyl-4-(3-pyridinyl)butyl]carbamic acid 1,1-dimethylethyl ester as a colorless oil.

EXAMPLE 11

Preparation of (R,S)-N-[1-methyl-4-(3-pyridinyl)butyl]acetamide

To a mixture of 10.6 g of (R,S)-alpha-methyl-3-pyridinebutanol in 30 mL of acetonitrile was added 20 mL of sulfuric acid. After the reaction was stirred at 50° C. for 2 hours, it was poured over a mixture of 500 g of ice and 400 mL of 4N NaOH and extracted with dichloromethane (2×150 mL). Evaporation of the dried (K₂CO₃) extracts gave 6 g of crude product which was purified by HPLC (methanol-ethyl acetate; 1:49) and triturated with ether to yield 2.9 g of (R,S)-N-[1-methyl-4-(3-pyridinyl)butyl]acetamide, mp 70°–71.5° C.

EXAMPLE 12

Preparation of (R,S)-alpha-methyl-3-pyridinebutanamine

A mixture of 248.5 g of 5-(3-pyridinyl)-2-pentanone, 95.85 g of sodium cyanoborohydride and 1170 g of ammonium acetate in 5.3 L of dry methanol was stirred at room temperature for 8 days, then 3 L of methanol was removed by distillation under reduced pressure (internal temp ~30° C.). The reaction was cooled in an ice bath as 3.8 L of 6N HCL was added dropwise over 2 hours. After the mixture was stirred at room temperature overnight, it was made strongly basic by the addition of 2 L of 12.5N NaOH and extracted with dichloromethane (1×2 L; 2×1 L). The combined extracts were dried (K$_2$CO$_3$) and evaporated to yield 244 g of a light brown oil, which was distilled to give 205 g of (R,S)-alpha-methyl-3-pyridinebutanamine (bp 95°–100° C./0.15 mm)

EXAMPLE 13

Preparation of (R,S)-alpha-methyl-3-pyridinebutanamine (a) From 3-(4-azidopentyl)pyridine A solution of 0.9 g of (R,S)-3-(4-azidopentyl)pyridine in 25 mL ethanol was hydrogenated over 0.05 g 10% Pd/C at 50 psi. After 105 minutes, the catalyst was removed by filtration and the solvent was removed under reduced pressure to yield 0.69 g of a colorless oil. Evaporative distillation of the crude product furnished 0.57 g of (R,S)-alpha-methyl-3-pyridinebutanamine.

(b) From (R,S)-[1-methyl-4-(3-pyridinyl)butyl]carbamic acid 1,1-dimethylethyl ester As in Example 37, hydrolysis of 2.1 g of (R,S)-[1-methyl-4-(3-pyridinyl)butyl]carbamic acid 1,1-dimethylethyl ester in 25 mL of 1N HCl yielded, after the usual work up and evaporative distillation of the product (95°–100° C./0.2 mm), 1.25 g of (R,S)-alpha-methyl-3-pyridinebutanamine.

(c) From (R,S)-N-[1-methyl-4-(3-pyridinyl)butyl]acetamide

A solution of 2.06 g of (R,S)-N-[1-methyl-4-(3-pyridinyl)butyl]acetamide in 50 mL of 6N HCl was stirred at reflux for 22 hours. In an argon atmosphere, the cooled mixture was made basic with the careful addition of 30 mL of 10N NaOH and was extracted with dichloromethane (2×75 mL). The extracts were washed with brine, then were combined, dried (K$_2$CO$_3$) and evaporated to give 1.43 g of (R,S)-alpha-methyl-3-pyridinebutanamine.

EXAMPLE 14

Preparation of [R-(R*,R*)]-alpha-hydroxy-N-[1-methyl-4-(3-pyridinyl)butyl]benzeneacetamide (a) From (R,S)-alpha-methyl-3-pyridinebutanamine A solution of 281.5 g of 1,3-dicyclohexylcarbodiimide in 400 ml of dimethylformamide was added to a stirred solution of 204 g of (R,S)-alpha-methyl-3-pyridinebutanamine, 198.4 g of (R)-mandelic acid and 209.75 g of 1-hydroxybenzotriazole in 1400 mL of dimethylformamide, maintained at −10° C. during the addition by intermittent cooling with a dry ice-acetone bath. After stirring at −5° for 4 hours, then at room temperature overnight the mixture was recooled to 0° C. for 2 hours. The precipitated solids were filtered and washed in turn with cold dimethylformamide (2×150 mL) and ethyl acetate (2×300 mL). This material, a mixture of 1,3-dicyclohexylurea (DCU) and the less soluble (R*,R)-mandelamide, was dispersed in 2 L of 1N HCl and stirred at room temperature for 3 hours. The undissolved solids (DCU) were removed by filtration and were washed with 200 mL of dilute HCl and with water. The filtrate was basified and the resulting material was collected by filtration, washed with water and dried in vacuo to give 64.4 g of [R-(R*,R*)]alpha-hydroxy-N-[1-methyl-4-(3-pyridinyl)butyl]benzeneacetamide, the (R*,R)-mandelamide, mp 144°–146° C.; [α]$_D^{25}$ −27.8° (c, 1.0, MeOH).

The original mother liquors and washings were concentrated to dryness under reduced pressure and the residue was dispersed in 2 L of 1.5N NaOH and extracted with dichloromethane (1×2 L; 2×1 L). The organic extracts were washed with in turn with 1N NaOH (2×800 mL) and then in turn with 1N HCl (1×1.5 L; 2×750 mL). The combined acidic aqueous layers were basified with 350 mL of 10N NaOH and extracted with dichloromethane (1×2 L; 2×1 L). The extracts were dried (K$_2$CO$_3$) and evaporated to give 280 g of mandelamide, rich (∼3:2) in the (S*,R)-diastereomer. The residue was crystallized three times from 2-propanol to yield 74.1 g of the less soluble (R*,R)-mandelamide, mp 144°–146° C.

The mother liquors from the final two crystallizations were combined, evaporated and the residue crystallized twice from 2-propanol to give an additional 7.2 g of the (R*,R)-diastereomer, mp 143°–145° C. The total yield of [R-(R*,R*)]-alpha-hydroxy-N-[1-methyl-4-(3-pyridinyl)butyl]benzeneacetamide, obtained in three crops, was 145.6 g (78.5%).

All remaining mother liquors were combined, evaporated and dried to give 198 g of mandelamide rich in the (S*,R)-diastereoisomer. This material was reserved for further processing, particularly to serve as a potential source of (S)-alpha-methyl-4-pyridinebutanamine.

(b) Via an enatioselective process from 5-(3-pyridinyl)-2-pentanone

A solution of 70.5 g of 5-(3-pyridinyl)-2-pentanone and 53.5 g of (R)-(+)-alpha-methylbenzylamine in 700 mL of toluene containing 1.8 g of p-toluenesulfonic acid was heated at reflux for 17 hours. Water was removed from the reaction as it was formed using a Dean-Stark trap. The cooled solution was hydrogenated over 70 g of Raney Nickel at room temperature and 50 psi. When approximately 50% of the theoretical amount of hydrogen had been taken up, the reaction essentially stopped. The spent catalyst was removed and replaced with 70 g of fresh Raney Nickel and the hydrogenation was continued until the absorption of hydrogen ceased. After the catalyst was removed by filtration, the filtrate was washed with 250 mL of 1N sodium hydroxide solution, then was dried and evaporated to give 106 g of an oil. HPLC analysis of the product showed that the main component (∼68%) was [R-(R*,R)]-N-[1-methyl-(3-pyridinyl)butyl]-alpha-methylbenzylamine along with 13% of the related (S*,R)-diastereomer.

The above mixture (105 g) in 1L of ethanol was hydrogenolysed over 21 g of 20% Pd(OH)$_2$ on charcoal (50° C.; 25 psi) for a total of 51 hours. After the catalyst was removed by filtration, the solvent was evaporated and the residue distilled to provide 33.6 g of alpha-methyl-3-pyridinebutanamine enriched in the (R)-enantiomer.

To a cooled (−5° C.) solution of 32 g of the above enriched amine, 33 g of 1-hydroxybenzotriazole and 31.22 g of (R)-mandelic acid in 350 mL of dimethylformamide, was added a solution of 44.26 g of 1,3-dicyclohexylcarbodiimide in 150 mL of dimethylformamide and the mixture was stirred at −5° C. for 18 hours. After the precipitated dicyclohexylurea was removed by filtration, the filtrate was evaporated and the residue dispersed in 300 mL of cold 2N sodium hydroxide. The resulting solids were removed by filtration, washed with dilute sodium hydroxide solution and with water and then dissolved in 500 mL of 2N hydrochloric acid. The acidic solution was extracted with dichloromethane (3×150 mL) to remove neutral impurities, then was basified with 10N sodium hydroxide and extracted with dichloromethane (6×300 mL). The dried extracts were evaporated to give 55 g of residual solid. Crystallization of the product from ethanol gave 25.6 g of [R-(R*,R)]-alpha-hydroxy-N-[1-methyl-4-(3-pyridinyl)butyl]benzeneacetamide, mp 141°–143° C. An additional 1.3 g of product, mp 141°–143° C., was obtained from the mother liquors.

EXAMPLE 15

Preparation of [S-(S*,S*)]-alpha-hydroxy-N-[1-methyl-4-(3-pyridinyl)butyl]benzeneacetamide (a) From (R,S)-alpha-methyl-3-pyridinebutanamine To an ice cold solution of 2.0 g of (S)-(+)-mandelic acid and 1.82 mL of triethylamine in 20 mL of dry dimethylformamide was added 2.82 mL of diphenylphosphoryl azide. The mixture was stirred at 0° C. for 30 minutes before 2.15 g of (R,S)-alpha-methyl-3-pyridinebutanamine was added. After the reaction was stirred at room temperature overnight, it was diluted with 130 mL of ethyl acetate, washed with water (4×50 mL), dried (K$_2$CO$_3$) and evaporated. The residue was crystallized from ethyl acetate (3x) to give 0.45 g of [S-(S*,S)]-alpha-hydroxy-N-[1-methyl-4-(3-pyridinyl)butyl]benzeneacetamide, mp 142°–145° C.

The absolute configuration of [S-(S*,S*)]-alpha-hydroxy-N-[1-methyl-4-(3-pyridinyl)butyl]benzeneacetamide, was established by X-ray crystallographic analysis.

(b) From enriched (S)-alpha-methyl-pyridinebutanamine

A solution of 160 g of crude [S-(R*,R*)]-alpha-hydroxy-N-[1-methyl-4-(3-pyridinyl)butyl]benzeneacetamide in 800 mL of 6N HCl was treated with 85 mL conc. HCl and then was heated at reflux overnight as described in Example 16. The crude amine (~85 g), isolated in the normal manner, was distilled to furnish 76.4 g of (S)-alpha-methyl-3-pyridinebutanamine, (60% ee; bp 89°–91°/0.15 mm).

Under the conditions outlined in Example 14a, 76.2 g of the amine was reacted with 74.2 g of (S)-mandelic acid in the presence of 105.2 g of 1,3-dicyclohexylcarbodiimide and 78.4 g of 1-hydroxybenzotriazole in 1 L of dimethylformamide. A similar workup furnished 109 g of [S-(S*,S*)]-alpha-hydroxy-N-[1-methyl-4-(3-pyridinyl)butyl]benzeneacetamide, mp 143°–145° C, $[\alpha]_D^{25}$+27.8° (c, 1.0, MeOH).

EXAMPLE 16

Preparation of (R)-alpha-methyl-3-pyridinebutanamine

A solution of 145 g of [R-(R*,R*)]-alpha-hydroxy-N-[1-methyl-4-(3-pyridinyl)butyl]benzeneacetamide in 900 mL of 6N HCl was treated with 80 mL of conc. HCl and then was heated at reflux for 2 days. After most of the solvent was removed under reduced pressure, the residue was made decidedly basic with 10N NaOH in an argon atmosphere, and extracted with dichloromethane (1×1.2 L; 2×600 mL). The dried (K$_2$CO$_3$) extracts were evaporated and the crude product was distilled to give 78.5 g of (R)-alpha-methyl-3-pyridinebutanamine, (bp 95° C./0.2 mm).

EXAMPLE 17

Preparation of (S)-alpha-methyl-3-pyridinebutanamine

As in Example 16, a solution of 16.3 g of [S-(S*,S*)]-alpha-hydroxy-N-[1-methyl-4-(3-pyridinyl)butyl]benzeneacetamide in 160 mL of 6N HCl was heated at reflux for 22 hours. The crude product, obtained by the usual work up was distilled to yield 8.3 g of (S)-alpha-methyl-3-pyridinebutanamine, (bp 85°–87° C./0.1 mm)

EXAMPLE 18

Preparation of (R,S)-alpha-ethyl-4-(3-pyridinyl)-3-butyn-1-ol

Under the conditions described in Example 1, 395 g of 3-bromopyridine and 259.3 g of (R,S)-5-hexyn-3-ol were reacted together in 1.5 L of dichloromethane in the presence of 418 mL of triethylamine, 17.56 g of bis(triphenylphosphine)palladium dichloride and 1.7 g of cuprous iodide. The usual work-up furnished 361.5 of crude (R,S)-alpha-ethyl-4-(3-pyridinyl)3-butyn-1-ol as a brown oil.

EXAMPLE 19

Preparation of (R,S)-alpha-ethyl-3-pyridinebutanol

As in Example 2, hydrogenation of 361.5 g of crude (R,S)-alpha-ethyl-4-(3-pyridinyl)-3-butyn-1-ol over 15 g of platinum oxide in 3 L of ethanol at room temperature and atmospheric pressure and distillation of the product furnished 357 g of (R,S)-alpha-ethyl-3-pyridinebutanol (bp 120°–130°/0.1 mm) as a colorless oil.

EXAMPLE 20

Preparation of 6-(3-pyridinyl)-3-hexanone

As in Example 3, 356.6 g of (R,S)-alpha-ethyl-3-pyridinebutanol was added to a mixture prepared in the prescribed manner from 211.7 g of oxalyl chloride and 170 g of dimethylsulfoxide in 1.75 L of dichloromethane. After the addition of 630 mL of triethylamine, the reaction was worked up in the usual way to yield 347.6 g of crude product which was distilled to give 327.9 g of 5-(3-pyridinyl)-3-hexanone (bp 110°–115° C./0.1 mm).

EXAMPLE 21

Preparation of (R,S)-alpha-ethyl-3-pyridinebutanamine

In the manner described in Example 12, 372.9 g of 6-(3-pyridinyl)-3-hexanone was reacted with 116.5 g of sodium cyanoborohydride and 1426 g of ammonium acetate in 6.5 L of dry methanol for 3 days at room temperature, and then 4.5 L of 6N HCl was added and the mixture stirred overnight. Distillation of the crude product gave 289.4 g of (R,S)-alpha-ethyl-3-pyridinebutanamine (bp 95°–100° C./0.1 mm).

EXAMPLE 22

Preparation of [R-(R*,R*)1-alpha-hydroxy-N-[1-ethyl-4-(3-pyridinyl)butyl]benzeneacetamide and [S-(R*,R*)]-alpha-hydroxy-N-[1-ethyl-4-(3-pyridinyl)butyl]benzeneacetamide.

As in Example 14a, a solution of 367.4 g of 1,3-dicyclohexylcarbodiimide in 500 mL of dimethylformamide was added to a stirred solution of 289 g of (R,S)-alpha-ethyl-3-pyridinebutanamine, 259 g of (R)-mandelic acid and 274 g of 1-hydroxybenzotriazole in 1.7 L of dimethylformamide maintained at −10° C. during the addition. After stirring at −5° C. for 3 hours, then at room temperature overnight, the mixture was recooled to 0° C. for 2 hours. The precipitated solids were filtered and washed in turn with cold dimethylformamide (3×150 mL) and ethyl acetate (3×200 mL). The solids, a mixture of 1,3-dicyclohexylurea (DCU) and the less soluble (R*,R)-mandelamide, was dispersed in 1N HCl (2 L) and stirred at room temperature for 4 hours. The undissolved solids (DCU) were removed by filtration and were washed with 200 mL dilute HCl and with water. The filtrate was basified and the resulting crystalline material was collected by filtration, washed with water and dried in vacuo to give 195.4 g of [R-(R*,R*)]-alpha-hydroxy-N-[1-ethyl-4-(3-pyridinyl)butyl]benzeneacetamide, mp 161.5°–163° C.; $[\alpha]_D^{25}$ −14.9° (c, 1.0 MeOH).

The original mother liquors and washings were concentrated to dryness and were worked up as in Example 14a. The crude residue was triturated with hot hexane (1 L), and the solids filtered to give 265 g of mandelamide rich (>7:1) in the more soluble (S*,R)-diastereomer. Fractional crystallization of the residue from 2-propanol furnished 147 g of [S-(R*,R*)]-alpha-hydroxy-N-[1-ethyl-4-(3-pyridinyl)butyl]benzeneacetamide, mp 122°–124° C.; $[\alpha]_D^{25}$ −41.2° (c, 1.0 MeOH).

EXAMPLE 23

Preparation of (R)-alpha-ethyl-3-pyridinebutanamine

As in Example 16, a solution of 195 g of [R-(R*,R*)]-alpha-hydroxy-N-[1-ethyl-4-(3-pyridinyl)butyl]benzeneacetamide in 1.1 L of 6N HCl was treated with 104 mL of conc. HCl and then was heated at reflux for 2 days. The crude amine, obtained by the normal work up, was distilled to give 109 g of (R)-alpha-ethyl-3-pyridinebutanamine, (bp 105° C./0.2 mm); $[\alpha]_D^{25}$ −11.9° (c, 1.0, MeOH)

EXAMPLE 24

Preparation of (S)-alpha-ethyl-pyridinebutanamine

As in Example 16, a solution of 31.2 g of [S-(R*,R*)]-alpha-hydroxy-N-[1-ethyl-4-(3-pyridinyl)butyl]benzeneacetamide in 175 ml of 6N HCl was treated with 16 mL of conc. HCl and then was heated at reflux for 42 hours. The normal work up furnished 16.4 g of (S)-alpha-ethyl-3-pyridinebutanamine, (bp 95°–98° C./0.1 mm); $[\alpha]_D^{25}$ +11.75° (c, 1.0, MeOH).

EXAMPLE 25

Preparation of trifluoromethanesulfonic acid 6-methyl-3-pyridinyl ester

A suspension of 7.48 g of 5-hydroxy-2-methylpyridine and 24.4 g of bis(trifluoromethanesulphonyl)-phenylimide in 25 mL of dichloromethane was cooled in an ice bath as 10 mL of dry triethylamine was added. After 1 hour at 0° C., the mixture was allowed to stir at room temperature for 18 hours, then was washed in turn with 1N NaOH (2×50 mL) and with half saturated K₂CO₃ solution. Concentration of the dried (K₂CO₃) solution gave a yellow oil which was evaporatively distilled to yield 14.48 g of trifluoromethanesulfonic acid 6-methyl-3-pyridinyl ester, (bp 65°–70° C./0.1 mm.)

EXAMPLE 26

Preparation of (R,S)-5-(6-methyl-3-pyridinyl)-4-pentyn-2-ol

A solution of 28 g trifluoromethanesulfonic acid 6-methyl-3-pyridinyl ester and 14.4 g of (R,S)-4-pentyn-2-ol and 110 mL triethylamine in 350 mL of dry dimethylformamide was deoxygenated with argon and 2.4 g of bis(triphenylphosphine)palladium dichloride was added. After the mixture was stirred at 90° C. for 3 hours, it was cooled, then acidified with 300 mL of 6N HCl and extracted with ether. The aqueous phase was made basic with sodium hydroxide solution and extracted with ethyl acetate. The organic extract was washed with brine, then dried (K₂CO₃) and evaporated to furnish an oil which was evaporatively distilled to yield 10.8 g of (R,S)-5-(6-methyl-3-pyridinyl)-4-pentyn-2-ol, bp 123°–130° C./0.02 mm.

EXAMPLE 27

Preparation of (R,S)-alpha-6-dimethyl-3-pyridinebutanol

As in Example 2, 10.3 g of (R,S)-5-(6-methyl-3-pyridinyl)-4-pentyn-2-ol was hydrogenated over 1.1 g of 10% Pd/C in 135 mL of ethanol at room temperature and atmospheric pressure. After the usual workup, the resulting yellow oil was purified by HPLC (ethyl acetate) to give 10.45 g of (R,S)-alpha-6-dimethyl-3-pyridinebutanol. A portion was evaporatively distilled at 105°–110° C./0.1 mm to furnish the analytical sample.

EXAMPLE 28

Preparation of 5-(6-methyl-3-pyridinyl)-2-pentanone

Under conditions similar to that describe in Example 3, 10.25 g of (R,S)-alpha-6-dimethyl-3-pyridinebutanol in 50 mL of dichloromethane was added to an mixture prepared from 8.58 g of oxalyl chloride and 9.27 g of dimethylsulfoxide in 225 mL of dichloromethane. After the addition of 36.8 mL of triethylamine, the reaction was worked up in the usual manner and the crude product was purified by HPLC (ethyl acetate-hexane; 1:1). The resulting material was distilled to give 7.4 g of 5-(6-methyl-3-pyridinyl)-2-pentanone (bp 88°–92° C./0.05 mm).

EXAMPLE 29

Preparation of (R,S)-6-alpha-dimethyl-3-pyridinebutanamine

As in Example 12, 7.27 g of 5-(6-methyl-3-pyridinyl)-2-pentanone was reacted with 2.71 g of sodium cyanoborohydride and 31.1 g of ammonium acetate in 115 mL of dry methanol for 3 days at room temperature. After the chilled reaction was quenched by the addition of 110 mL of 6N HCl, the mixture heated at reflux for 90 minutes then was cooled and worked up in the usual manner. Distillation of the crude product gave 4.31 g of (R,S)-6-alpha-dimethyl-3-pyridinebutanamine (bp 98°–101° C./0.1 mm).

EXAMPLE 30

Preparation of 5-bromo-2-[(2-trimethylsilyl)ethynyl]pyridine

A degassed solution of 15.0 g of 2,5-dibromopyridine, 9.0 mL of trimethylsilylacetylene and 0.27 g of cuprous iodide in 200 mL of triethylamine was treated with 1.0 g of bis(triphenylphosphine)palladium dichloride. After an ice bath was used to control the initial exotherm, the reaction was stirred at room temperature overnight, then was diluted with 400 mL ether. The mixture was washed in turn with water (4×75 mL) and with brine (75 mL), then was dried ($K_2CO_3$) and evaporated. The residual dark oil was passed through a plug of silica gel (ether) and then was purified by HPLC (ether-hexane; 1:49). Crystallization of the resulting material from hexane gave 11.86 g of 5-bromo-2-[(2-trimethylsilyl)ethynyl]pyridine, mp 56°–59° C.

EXAMPLE 31

Preparation of (R,S)-5-[6-[2-trimethylsilyl)ethynyl]-3-pyridinyl]-4-pentyn-2-ol

A solution of 9.78 g of 5-bromo-2-[(2-trimethylsilyl)ethynyl]pyridine and 0.19 g of cuprous iodide in 150 mL of triethylamine and 50 mL dichloromethane were deoxygenated with argon and 3.4 g of (R,S)-4-pentyn-2-ol and 0.7 g of bis(triphenylphosphine)palladium dichloride were added. After the dark mixture was stirred overnight at room temperature, the solvents were removed under reduced pressure and the residue was dissolved in ether. The solution was washed with water and brine, then was dried ($K_2CO_3$) and evaporated. The crude product was filtered through a plug of silica gel (ethyl acetate-hexane; 1:10) and then was purified by HPLC (ethyl acetate) to give (R,S)-5-[6-[2-trimethylsilyl)ethynyl]-3-pyridinyl]-4-pentyn-2-ol, mp 79°–80° C.

EXAMPLE 32

Preparation of (R,S)-6-ethyl-3-pyridine-alpha-methylbutanol

A solution of 8.51 g of (R,S)-5-[6-[2-(trimethylsilyl)ethynyl]-3-pyridinyl]-4-pentyn-2-ol in 60 mL of methanol and 15 mL of 2.5N NaOH was stirred for 1 hour and diluted to 300 mL with ethyl acetate. The separated organic layer was washed in turn with water and brine, then was dried ($K_2CO_3$) and evaporated. The residue was hydrogenated over 0.7 g of 10% Pd/C in 150 mL of ethanol at atmospheric pressure and room temperature. After the normal work up, the crude hydrogenation product was evaporatively distilled to afford 5.61 g of (R,S)-6-ethyl-3-pyridine-alpha-methylbutanol (bp 110°–115° C./0.1 mm).

EXAMPLE 33

Preparation of 5-(6-ethyl-3-pyridinyl)-2-pentanone 5-(6-Ethyl-3-pyridinyl)-2-pentanone was prepared by the method described in Example 3. Starting with 4.4 g of (R,S)-6-ethyl-3-pyridine-alpha-methylbutanol, there was obtained 4.9 g of 5-(6-ethyl-3-pyridinyl)-2-pentanone (bp 107°–110° C./0.1 mm).

EXAMPLE 34

Preparation of (R,S)-6-ethyl-alpha-methyl-3-pyridinebutanamine (R,S)-6-ethyl-alpha-methyl-3-pyridinebutanamine was made by the method outlined in Example 12. Starting from 4.75 g of 5-(6-ethyl-3-pyridinyl)-2-pentanone there was obtained 2.44 g of (R,S)-6-ethyl-alpha-methyl-3-pyridinebutanamine, bp 101°–104° C./0.15 mm.

EXAMPLE 35

Preparation of (R,S)-alpha-cyclopropyl-3-pyridinepentanoic acid

In an inert atmosphere, 33 mL of 1.6M butyl lithium in hexane was added to a stirred solution of 7.4 mL diisopropylamine in 20 mL dry tetrahydrofuran previously cooled to −78° C. for 30 minutes, then a solution of 2.5 g cyclopropaneacetic acid in 10 mL dry tetrahydrofuran was added over 3 minutes. The reaction was allowed to equilibrate to ambient temperature and then was heated at 50° C. for 1 hour to complete the formation of the dianion. The mixture was recooled to −78° C. and a solution of 7.67 g 3-(3-bromopropyl) pyridine (freshly liberated from its HBr salt) in 20 mL tetrahydrofuran was added. The reaction was allowed to warm to room temperature and then was heated at 50° C. for 7 hours. The solvents were removed in vacuo and the residue was dissolved in 100 mL 1N HCl and extracted with dichloromethane (3×50 ml). The organic layers were backwashed in turn with 2×25 mL portions of 1N HCl, then the aqueous layers were basified with 17 mL 10N NaOH solution and extracted with dichloromethane (3×100 mL) to remove the starting bromide. The aqueous phase was then acidified by the addition of 3 mL acetic acid and extracted with dichloromethane (1×150 mL; 2×100 mL). The extracts were washed with brine, then were combined, dried ($Na_2SO_4$) and evaporated to give 4.6 g of (R,S)-alpha-cyclopropyl-3-pyridinepentanoic acid as a colorless solid. A portion was crystallized from ether-hexane to yield the analytical sample, mp 82°–84° C.

EXAMPLE 36

Preparation of (R,S)-[1-cyclopropyl-4-(3-pyridinyl)butyl]carbamic acid 1,1-dimethylethyl ester A solution of 4.2 g of (R,S)-alpha-cyclopropyl-3-pyridinepentanoic acid 5.8 g of diphenylphosphorylazide and 3 mL of triethylamine in 40 mL of t-butanol was stirred at reflux under argon overnight. After the solvents were removed under reduced pressure, the residue was dissolved in 100 mL of dichloromethane and washed with 2×50 mL portions of 1N NaOH. The aqueous layers were washed in turn with 50 mL of dichloromethane. Then the combined organic extracts were dried ($K_2CO_3$) and evaporated to yield 5.6 g of an oil. The crude carbamate was purified by HPLC (ethyl acetate) to furnish 4.8 g of (R,S)-[1-cyclopropyl-4-(3-pyridinyl)butyl]carbamic acid 1,1-dimethylethyl ester as a colorless oil.

EXAMPLE 37

Preparation of (R,S)-alpha-cyclopropyl-3-pyridinebutanamine

A solution of 4.4 g of (R,S)-[1-cyclopropyl-4-(3-pyridinyl)butyl]-carbamic acid 1,1-dimethylethyl ester in 50 mL of 1N HCl was heated on a steam bath for 75 minutes then was cooled and extracted with 50 mL of ether. In an atmosphere of argon, the aqueous layer was treated with 6 mL of 10N NaOH and extracted with 2×50 mL portions of dichloromethane. Evaporation of the dried ($K_2CO_3$) extracts gave 2.8 g of (R,S)-alpha-cyclopropyl-3-pyridinebutanmine as a colorless oil.

EXAMPLE 38

Preparation of (R,S)-alpha-propyl-3-pyridinepentanoic acid

As in Example 35, 2.04 g of pentanoic acid was treated with two equivalents of lithium diisopropylamide (LDA) and then reacted with 4.0 g of 3-(3-bromopropyl)pyridine. After workup, the crude product (3.5 g) was crystallized from ether-hexane to afford 2.7 g of (R,S)-alpha-propyl-3-pyridinepentanoic acid, mp 55°–57° C.

EXAMPLE 39

Preparation of (R,S)-[1-propyl-4-(3-pyridinyl)butyl]carbamic acid 1,1-dimethylethyl ester As in Example 36, 2.5 g of (R,S)-alpha-propyl-3-pyridinepentanoic acid when reacted with 2.45 mL of diphenylphosphorylazide in 25 mL of t-butanol containing 1.6 mL of triethylamine furnished 3.1 g of crude carbamate. Purification of the material by HPLC (ethyl acetate) yielded 2.75 g (R,S)-[1-propyl-4-(3-pyridinyl)butyl]carbamic acid 1,1-dimethylethyl ester as an oil.

EXAMPLE 40

Preparation of (R,S)-alpha-propyl-3-pyridinebutanamine

As in Example 37, hydrolysis of 1.8 g of (R,S)-[1-propyl-4-(3-pyridinyl)butyl]carbamic acid 1,1-dimethylethyl ester in 25 mL of 1N HCl, after the usual workup, gave 1.15 g of (R,S)-alpha-propyl-3-pyridinebutanamine. A portion was distilled on a Kugelrohr apparatus (110° C./0.1 mm) to yield the analytical sample.

EXAMPLE 41

Preparation of (R,S)-alpha-(1-methylethyl)-3-pyridinepentanoic acid

As in Example 35, 2.04 g of isovaleric acid was treated with two equivalents of LDA and then reacted with 4.0 g of 3-(3-bromopropyl)pyridine. The crude product was crystallized from ether-hexane to yield 2.8 g of (R,S)-alpha-(1-methylethyl)-3-pyridinepentanoic acid, mp 52°–55° C. Recrystallization of a sample from the same solvents gave the analytical specimen, mp 54°–56° C.

EXAMPLE 42

Preparation of (R,S)-[1-(1-methylethyl)-4-(3-pyridinyl)butyl]carbamic acid 1,1-dimethylethyl ester As in Example 36, 2.3 g of (R,S)-alpha-(1-methylethyl-3-pyridine-pentanoic acid, when reacted with 2.3 mL of diphenylphosphorylazide in 25 mL of t-butanol containing 1.5 mL of triethylamine gave 2.8 g of product. Purification of the crude ester by HPLC (ethyl acetate) gave 2.5 g of (R,S)-[1-(1-methylethyl)-4-(3-pyridinyl)butyl]carbamic acid 1,1-dimethylethyl ester as an oil.

EXAMPLE 43

Preparation of (R,S)-alpha-(1-methylethyl)-3-pyridinebutanamine

As in Example 37, hydrolysis of 1.7 g of (R,S)-[1-(1-methylethyl)-4-(3-pyridinyl)butyl]carbamic acid 1,1-dimethylethyl ester in 25 mL of 1N HCl yielded 1.1 g of (R,S)-alpha-(1-methylethyl)-3-pyridinebutanamine. A small sample was distilled on a Kugelrohr (110°–115° C./0.1 mm) to furnish the analytical specimen.

EXAMPLE 44

Preparation of (R,S)-alpha-butyl-3-pyridinepentanoic acid

As in Example 35, 2.32 g of hexanoic acid was treated with two equivalents of LDA and then reacted with 4.0 g of 3-(3-bromopropyl)pyridine. The usual workup yielded 4 g of (R,S)-alpha-butyl-3-pyridinepentanoic acid, as an oil.

EXAMPLE 45

Preparation of (R,S)-1-[1-butyl-4-(3-pyridinyl)butyl]carbamic acid 1,1-dimethylethyl ester As in Example 36, 3.7 g of (R,S)-alpha-butyl-3-pyridine-pentanoic acid, when reacted with 3.4 mL of diphenylphosphorylazide in 25 mL of t-butanol containing 2.2 mL of triethylamine yielded 4.4 g of crude carbamate. Purification of the product by HPLC (ethyl acetate) gave 3.6 g of (R,S)-[1-butyl-4-(3-pyridinyl)butyl]carbamic acid 1,1-dimethylethyl ester as an oil.

EXAMPLE 46

Preparation of (R,S)-alpha-butyl-3-pyridinebutanamine

As in Example 37, hydrolysis of 2.2 g of (R,S)-[1-butyl-4-(3-pyridinyl)butyl]carbamic acid 1,1-dimethylethyl ester in 25 mL 1N HCl, after the usual workup, yielded 1.35 g of (R,S)-alpha-butyl-3-pyridinebutanamine. A portion was distilled on a Kugelrohr (115° C./0.1 mm) to yield the analytical sample.

EXAMPLE 47

Preparation of (R,S)-alpha-cyclopentyl-3-pyridinepentanoic acid

As in Example 35, 2.56 g of cyclopentaneacetic acid was treated with two equivalents of LDA and then reacted with 4.0 g of 3-(3-bromopropyl)pyridine. The crude product (4 g) was crystallized from ether-hexane to yield 3.1 g of (R,S)-alpha-cyclopentyl-3-pyridinepentanoic acid, mp 95°–97° C.

EXAMPLE 48

Preparation of (R,S)-[1-cyclopentyl-4-(3-pyridinyl)butyl]carbamic acid 1,1-dimethylethyl ester As in Example 36, 2.8 g of (R,S)-alpha-cyclopentyl-3-pyridinepentanoic acid, when treated with 2.5 mL of diphenylphosphorylazide in 25 mL of t-butanol containing 1.58 mL of triethylamine yielded 3.4 g of product. Purification of the crude by HPLC (ethyl acetate) yielded 2.5 g of (R,S)-[1-cyclopentyl-4-(3-pyridinyl)butyl]carbamic acid 1,1-dimethylethyl ester as an oil.

EXAMPLE 49

Preparation of (R,S)-alpha-(1-cyclopentyl)-3-pyridinebutanamine

As in Example 37, hydrolysis of 1.6 g of (R,S)-[1-cyclopentyl)-4-(3-pyridinyl)butyl]carbamic acid 1,1-dimethylethyl ester in 25 mL of 1N HCl yielded 1.05 g of (R,S)-alpha-(1-cyclopentyl)-3-pyridinebutanamine. A sample was distilled (125°–130° C./0.1 mm) to yield the analytical specimen.

EXAMPLE 50

Preparation of
(R,S)-alpha-cyclohexyl-3-pyridinepentanoic acid

As in Example 35, 2.84 g of cyclohexaneacetic acid was treated with two equivalents of LDA and then reacted with 4.0 g of 3-(3-bromopropyl)pyridine. The crude product (3.8 g) was crystallized from ether-hexane to give 2.7 g of (R,S)-alpha-cyclohexyl-3-pyridinepentanoic acid, mp 92°–93° C.

EXAMPLE 51

Preparation of
(R,S)-[1-cyclohexyl-4-(3-pyridinyl)butyl]carbamic acid 1,1-dimethylethyl ester As in Example 36, 2.5 g of (R,S)-alpha-cyclohexyl-3-pyridinepentanoic acid, when reacted with 2.68 g of diphenylphosphorylazide in 25 mL of t-butanol containing 0.97 g of triethylamine yielded 3.1 g of crude product. Purification by HPLC (ethyl acetate) furnished 2.8 g of (R,S)-[1-cyclohexyl-4-(3-pyridinyl)butyl]carbamic acid 1,1-dimethylethyl ester. The material was crystallized from ether-hexane to yield the analytical sample, mp 64°–66° C.

EXAMPLE 52

Preparation of
(R,S)-alpha-(1-cyclohexyl)-3-pyridinebutanamine

As in Example 37, hydrolysis of 1.9 g of (R,S)-1-[1-cyclohexyl-4-(3-pyridinyl)butyl]carbamic acid 1,1-dimethylethyl ester in 25 mL of 1N HCl yielded 1.25 g of (R,S)-alpha-(1-cyclohexyl)-3-pyridinebutanamine. Distillation of a portion of the material on a Kugelrohr apparatus (140°–145° C./0.1 mm) yielded the analytical sample.

EXAMPLE 53

Preparation of
alpha-[3-(3-pyridinyl)propyl]-3-pyridinepentanoic acid

As in Example 35, 7.16 g of 3-pyridinepentanoic acid was treated with two equivalents of LDA and then reacted with 8.8 g of 3-(3-bromopropyl)pyridine. The usual work-up yielded 8.9 g of an orange colored oil, consisting mainly of alpha-[3-(3-pyridinyl)propyl]-3-pyridinepentanoic acid contaminated by a small amount of starting 3-pyridinepentanoic acid.

EXAMPLE 54

Preparation of
[1-[3-(3-pyridinyl)propyl]-4-(3-pyridinyl)butyl]carbamic acid 1,1-dimethylethyl ester As in Example 36, 8.8 g of alpha-[3-(3-pyridinyl)propyl]-3-pyridinepentanoic acid, when reacted with 9.1 g of diphenylphosphorylazide in 75 mL of t-butanol containing 4.1 mL of triethylamine furnished 11.1 g of product. Purification of the crude by HPLC (ethyl acetate-methanol; 13:1) yielded 5.5 g of [1-[3-(3-pyridinyl)propyl]-4-(3-pyridinyl)butyl]carbamic acid 1,1-dimethylethyl ester as an oil.

EXAMPLE 55

Preparation of
alpha-[3-(3-pyridinyl)propyl]-3-pyridinebutanamine

As in Example 37, hydrolysis of 5.4 g of [1-[3-(3-pyridinyl)-propyl)-4-(3-pyridinyl)butyl]carbamic acid 1,1-dimethylethyl ester in 55 mL of 1N HCl yielded 3.15 g of alpha-[3-(3-pyridinyl)propyl]-3-pyridinebutanamine.

EXAMPLE 56

Preparation of
(R,S)-alpha-(4-bromophenyl)-3-pyridinepentanoic acid

As in Example 35, 2.15 g of p-bromophenylacetic acid was treated with two equivalents of LDA and then reacted with 2.0 g of 3-(3-bromopropyl)pyridine. The crude product was crystallized from ether-hexane to yield 1.46 g of (R,S)-alpha-(4-bromophenyl)-3-pyridinepentanoic acid, mp 123°–126° C.

EXAMPLE 57

Preparation of
(R,S)-[1-(4-bromophenyl)-4-(3-pyridinyl)butyl]carbamic acid 1,1-dimethylethyl ester As in Example 36, 1.45 g of (R,S)-alpha-(4-bromophenyl)-3-pyridinepentanoic acid, when treated with 0.94 mL of diphenylphosphorylazide in 10 mL of t-butanol containing 0.44 g of triethylamine yielded 1.7 g of crude (R,S)-[1-(4-bromophenyl)-4-(3-pyridinyl)butyl]carbamic acid 1,1-dimethylethyl ester as an oil.

EXAMPLE 58

Preparation of
(R,S)-alpha-(4-bromophenyl)-3pyridinebutanamine

As in Example 37, hydrolysis of 1.7 g of (R,S)-[1-(4-bromophenyl)-4-(3-pyridinyl)butyl]carbamic acid 1,1-dimethylethyl ester in 15 mL of 1N HCl yielded 1.1 g of (R,S)-alpha-(4-bromophenyl)-3-pyridinebutanamine.

EXAMPLE 59

Preparation of
[(R,S)-Z]-2-methyl-5-(3-pyridinyl)-4-pentenoic acid

A solution of 9.95 g of [(R,S)-Z]-2-methyl-5-(3-pyridinyl)-4-pentenoic acid ethyl ester in 75 mL of 1N NaOH and 75 mL of methanol were stirred at reflux for 3 hours, then most of the methanol was removed under reduced pressure. After the solution was extracted with dichloromethane (3×50 mL), the aqueous layer was neutralized with 75 ml of 1N HCl and extracted with dichloromethane (4×40 mL). The dried (Na$_2$SO$_4$) extracts were evaporated to give 7.28 g of a solid which was crystallized from ether-hexane to yield 6.12 g of [(R,S)-Z]-2-methyl-5-(3-pyridinyl)-4-pentenoic acid, mp 79°–82° C.

EXAMPLE 60

[(R,S)-Z]-[1-methyl-4-(3-pyridinyl)-3-butenyl]carbamic acid 1,1-dimethylethyl ester As in Example 36, 2.87 g of [(R,S)-Z]-2-methyl-5-(3-pyridinyl)-4-pentenoic acid was reacted with 3.31 mL of diphenylphosphoryl azide in 30 mL of t-butanol containing 2.1 mL of triethylamine. The product was isolated in the usual manner to yield 3.88 g of [(R,S)-Z]-1-[1-methyl-4-(3-pyridinyl)-3-butenyl]carbamic acid 1,1-dimethylethyl ester as an oil.

EXAMPLE 61

[(R,S)-Z]-1-methyl-4-(3-pyridinyl)-3-butenamine

As in Example 37, hydrolysis of 3.88 g of [(R,S)-Z]-[1-methyl-4-(3-pyridinyl)-3-butenyl]carbamic acid 1,1-dimethylethyl ester in 50 mL of 1N HCl yielded, after the usual work-up and evaporative distillation of the product (100°-120° C./0.1 mm), 1.7 g of [(R,S)-Z]-1-methyl-4-(3-pyridinyl)-3-butenamine as an oil.

EXAMPLE 62

Preparation of 3-(4-methyl-4-pentenyl)pyridine

A suspension of 7.0 g of sodium hydride (60% dispersion in oil) in 75 mL of dry dimethylsulfoxide was stirred at 75° C. under argon for 45 minutes, at which time the evolution of hydrogen had ceased. After the solution was cooled, 61 g of methyltriphenylphosphonium bromide was added and the mixture was stirred at room temperature for 30 minutes before the addition of 25 g of 5-(3-pyridinyl)-2-pentanone in 125 mL of dimethylsulfoxide. The reaction was then stirred at room temperature overnight. After the addition of 1L of 1N hydrochloric acid solution, the precipitated triphenylphosphine oxide was removed by filtration, and the filtrate was basified with 110 mL of 10N sodium hydroxide. The product was extracted with dichloromethane (4×300 ml) and the extracts were washed with brine, then were combined, dried ($K_2CO_3$) and evaporated to give 25 g of crude product. The material was purified by HPLC (ethyl acetate:hexane: 1:1) to yield 17.5 g of 3-(4-methyl-4-pentenyl)pyridine as a colorless oil.

EXAMPLE 63

Preparation of N-[1,1-dimethyl-4-(3-pyridyl)butyl]-2-nitrobenzeneacetamide

A mixture of 22.7 g of 3-(4-methyl-pentenyl)pyridine and 22.8 g of 2-nitrobenzeneacetonitrile in 80 mL of acetic acid was cooled to 12°-13° C. and then 16 mL of sulfuric acid was added dropwise over 6 minutes. The reaction was stirred for 2 hours at ambient temperature, then after the acetic acid was removed in vacuo, 1 L of water was added and the mixture was extracted with dichloromethane to remove neutral impurities. The aqueous layer was basified with 10N sodium hydroxide, and extracted with dichloromethane (4×200 mL). The dried ($K_2CO_3$) extracts were evaporated to give 35.6 g of N-[1,1-dimethyl-(3-pyridyl)butyl]-2-nitrobenzeneacetamide. A portion was crystallized from ethyl acetate-hexane to yield the analytical sample, mp 117°-118.5° C.

EXAMPLE 64

Preparation of alpha,alpha-dimethyl-3-pyridinebutanamine.

A solution of 35.2 g of N-[1,1-dimethyl-4-(3-pyridyl)-butyl]-2-nitrobenzeneacetamide in 250 mL of acetic acid was hydrogenated over 3.5 g of 10% Pd/C at atmospheric pressure and ambient temperature. The reaction was exothermic and stopped abruptly after the uptake of the theoretical amount of hydrogen (7.5 L). The catalyst was removed by filtration and the filtrate was heated at reflux for 90 minutes. After the solution was cooled, 10 mL of conc. HCl was added and the solvent was removed under reduced pressure. The residue was taken up in 1 L of water and extracted with ethyl acetate (4×200 mL) to remove the byproduct, oxindole. The aqueous layer was basified with 10N NaOH and extracted with dichloromethane to give, after evaporation of the dried ($K_2CO_3$) extracts 15 g of product. The material was distilled on a Kugelrohr apparatus (95° C.; 0.1 mm) to yield 14.3 g of alpha,alpha-dimethyl-3-pyridinebutanamine.

EXAMPLE 65

Preparation of 4-pyridinepropanamide

In an inert atmosphere 10.7 g of 4-pyridinecarboxaldehyde was added to a stirred solution of 35.1 g of (carbomethoxy)methylenetriphenylphosphorane in 250 mL of methanol. After 90 minutes, the solvent was removed under reduced pressure and the residue was triturated with ether-hexane. The resulting solid (triphenylphosphine oxide) was removed by filtration, and the filtrate was evaporated to yield 18 g of a mixture of (E)- and (Z)-3-(4-pyridinyl)-2-propenoic acid methyl ester contaminated with a small amount of residual triphenylphosphine oxide.

The crude mixture (18 g) was hydrogenated over 1.6 g of 10% Pd/C in 200 mL of methanol at atmospheric pressure and room temperature. After the uptake of hydrogen had stopped, the catalyst was removed by filtration and the solvent was removed in vacuo to furnish 16 g of crude 4-pyridinepropanoic acid methyl ester.

The crude ester was dissolved in 250 mL of 7.1M methanolic ammonia solution and was stirred at room temperature for 65 hours. After the solvent and excess ammonia were removed by distillation under reduced pressure, the residue was dissolved in 150 mL of 1N HCl and extracted with dichloromethane to remove residual triphenylphosphine oxide. The aqueous phase was basified with 40 mL of 4N NaOH and then was extracted with ethyl acetate (5×300 mL). The dried ($Na_2SO_4$) extracts were evaporated to furnish 6 g of the amide. The aqueous layer was concentrated to dryness and triturated with tetrahydrofuran (4×100 mL) and evaporation of the tetrahydrofuran extracts yielded an additional 5 g of amide. The combined crude products were dried, triturated with ether and the solids were filtered to yield 10.7 g of 4-pyridinepropanamide, mp 164°-166° C.

EXAMPLE 66

Preparation of 4-pyridinepropanamine

A 1M solution of $BH_3$ in tetrahydrofuran (192 mL) was added over 10 minutes to a stirred suspension of 7.2 g of 4-pyridinepropanamide in 50 mL of tetrahydrofuran at 0°-5° C. After the cooling bath was removed, the reaction was stirred at reflux for 17 hours and then the solvent was removed in vacuo. The residue was dissolved in 160 mL of 3.5N HCl and after the solution was heated on a steam bath overnight, it was cooled, basified with excess 10N NaOH and then extracted with dichloromethane. The dried ($K_2CO_3$) extract was evaporated to furnish 6.98 g of an amber oil, which was distilled in vacuo to give 4.3 g of 4-pyridinepropanamine (bp 100°-110° C./0.2 mm).

EXAMPLE 67

Preparation of 5-(2-pyridinyl)-4-pentyn-1-ol.

As in Example 1, 15.8 g of 2-bromopyridine and 8.4 g of 4-pentyn-1-ol were reacted together in 125 mL of dichloromethane in the presence of 4.2 mL of triethylamine, 2.1 g of bis(triphenylphosphine)palladium dichloride and 0.135 g of cuprous iodide. After 48 hours at reflux, the reaction was worked up in the usual manner. Distillation of the crude product yielded 8.8 g of 5-(2-pyridinyl)-4-pentyn-1-ol (bp 115°–120° C./0.25 mm).

EXAMPLE 68

Preparation of 2-pyridinepentanol 5-(2-Pyridinyl)-4-pentyn-1-ol (8.8 g) was hydrogenated over 1.0 g of 10% Pd/C in 125 mL of ethanol at room temperature and atmospheric pressure. After the uptake of hydrogen had stopped, the catalyst was removed by filtration and the solvent was removed under reduced pressure. The residual oil was distilled on a Kugelrohr apparatus (115°–120° C./0.1 mm) to yield 8.4 g of 2-pyridinepentanol.

EXAMPLE 69

Preparation of 2-(5-chloropentyl)pyridine

A solution of 4.1 mL of thionyl chloride in 30 mL of dichloromethane was added over 10 minutes to a stirred solution of 6.65 g of 2-pyridinepentanol in 60 mL of dichloromethane maintained at −5° C. After the addition was complete, the mixture was stirred at room temperature for 17 hours, then was rechilled to 5° C. as 150 ml of 1N NaOH was added dropwise over 10 minutes. The layers were separated and the aqueous layer was extracted with 75 mL of dichloromethane. The organic layers were washed with brine, then were combined, dried ($K_2CO_3$) and evaporated to yield 7.4 g of 2-(5-chloropentyl)pyridine as an oil.

EXAMPLE 70

Preparation of 1-[5-(2-pyridinyl)pentyl]-1H-isoindole-1,3-(2H)-dione

A mixture of 6.35 g of 2-(5-chloropentyl)pyridine, 7.7 g potassium phthalimide, 5.2 g of sodium iodide and 3.7 g of sodium carbonate in 50 mL of dimethylformamide was stirred at 50° C. for 20 hours. After the solvent was removed under reduced pressure, the residue was taken up in 100 mL of water and extracted with dichloromethane (1×250 mL; 1×150 mL). The organic extracts were washed with brine, then were combined, dried ($K_2CO_3$) and concentrated in vacuo to give 10.1 g of an orange colored oil. Purification of the crude material by HPLC (ethyl acetate-hexane) yielded 6.7 g of 1-[5-(2-pyridinyl)pentyl]-1H-isoindole-1,3-(2H)-dione.

EXAMPLE 71

Preparation of 2-pyridinepentanamine

A solution of 6.5 g of 1-[5-(2-pyridinyl)pentyl]-1H-isoindole-1,3-(2H)-dione and 1.15 mL of hydrazine hydrate in 35 mL of ethanol was heated at reflux for 90 minutes. The cooled reaction mixture was treated with 10 ml of 6N HCl, and the solids were removed by filtration and washed with 20 mL of 0.5N HCl. After the filtrate was concentrated to remove ethanol, it was basified with 10N NaOH and extracted with dichloromethane. The organic extract was washed with brine, then was dried ($K_2CO_3$) and evaporated to give 3.4 g of a yellow oil. The crude reaction product was evaporatively distilled (105°–110° C./0.01 mm) to yield 2.4 g of 2-pyridinepentanamine.

EXAMPLE 72

Preparation of 3-(8-isoquinolinyl)-2-propyn-1-ol

In an inert atmosphere, 0.068 g of bis(triphenylphosphine)palladium dichloride and 0.013 g of cuprous iodide was added with stirring to a deoxygenated solution of 1 g of 8-bromoisoquinoline, 0.56 mL of propargyl alcohol and 2 mL of triethylamine in 25 mL of dichloromethane. The mixture was stirred at room temperature for 2 hours and then at reflux for 20 hours. The cooled reaction was filtered and the filtrate was concentrated in vacuo. The residual oil was purified by HPLC (ethyl acetate-toluene; 2:3) to yield 0.4 g of 3-(8-isoquinolinyl)-2-propyn-1-ol, mp 138°–139° C.

EXAMPLE 73

Preparation of 8-isoquinolinepropanol

A solution of 0.4 g of 3-(8-isoquinolinyl)-2-propyn-1-ol in a mixture of 10 mL of ethanol and 5 mL of methanol was hydrogenated over 0.06 g 10% Pd/C at room temperature and atmospheric pressure for 22 hours and then at 50 psi for 20 hours. After the catalyst was removed by filtration and the filtrate was concentrated, the residual oil was purified by HPLC (methanol-chloroform; 1:19) and crystallized from ethyl acetate-hexane to yield 0.136 g of 8-isoquinolinepropanol, mp 66°–69° C.

EXAMPLE 74

Preparation of [3-(8-isoquinolinyl)propyl]-1H-isoindole-1,3-(2H)-dione

A solution of 0.142 g of 8-isoquinolinepropanol in 3 mL of chloroform was added to a solution of 0.085 mL of thionyl chloride in 1 mL of chloroform and the reaction was stirred at reflux for 3 hours. The cooled mixture was washed with $NaHCO_3$ solution and with brine, then was dried ($Na_2SO_4$) and evaporated. The residual oil was stirred with 0.281 g of potassium phthalimide and 0.126 potassium iodide in 3 mL of dry dimethylformamide at 130° C. for 90 minutes. After evaporation of the solvent, the residue was partitioned between dichloromethane and water. The dried ($Na_2SO_4$) organic layer was concentrated and the crude product was purified by HPLC (ethyl acetate-toluene; 1:4) and then crystallized from ether to give 0.177 g of [3-(8-isoquinolinyl)propyl]-1H-isoindole-1,3-(2H)-dione, mp 135°–140° C.

EXAMPLE 75

Preparation of 8-isoquinolinepropanamine

To a refluxing solution of 0.174 g of [3-(8-isoquinolinyl)propyl]-1H-isoindole-1,3-(2H)-dione in 8 mL of ethanol was added 0.12 mL of hydrazine hydrate and the reaction was stirred at reflux for 5.5 hours. The solvent was removed under reduced pressure and the residue was triturated with chloroform. The chloroform extract was concentrated to an oil which was passed through a short column of silica gel (chloroform-methanoltriethylamine; 1:4:15) to yield 0.103 g of 8-isoquinolinepropanamine as an oil.

EXAMPLE 76

Preparation of 4-(4-isoquinolinyl)-3-butyn-1-ol

In an inert atmosphere, 0.268 g of bis(triphenylphosphine) palladium dichloride and 0.072 g of cuprous iodide was added with stirring to a deoxygenated solution of 5 g of 4-bromoisoquinoline, 3.02 g of 3-butyn-1-ol and 10 mL of triethylamine in 20 mL of dichloromethane. The reaction was stirred at room temperature for 1 hour and then at reflux for 18 hours. The cooled mixture was filtered and the filtrate was washed with water. The dried ($Na_2SO_4$) organic phase was concentrated in vacuo and the residual oil was purified by HPLC (ethyl acetate-toluene; 2:3) to yield 3.4 g of 4-(4-isoquinolinyl)-3-butyn-1-ol as an oil.

EXAMPLE 77

Preparation of (E)-4-(4-isoquinolinyl)-3-buten-1-ol

A solution of 3.4 g of 4-(4-isoquinolinyl)-3-butyn-1-ol in 35 mL of ethanol was hydrogenated over 0.35 g of 10% Pd/C at room temperature and atmospheric pressure for 5 hours. The catalyst was removed by filtration and the filtrate was evaporated to yield 3.3 g of (E)-4-(4-isoquinolinyl)-3-buten-1-ol as an oil.

EXAMPLE 78

Preparation of (E)-4-(4-chloro-1-butenyl)isoquinoline

A solution of 3.3 g of (E)-4-(4-isoquinolinyl)-3-buten-1-ol in 15 mL of dry chloroform was added to a cold solution of 1.8 mL of thionyl chloride in 5 mL of dry chloroform. After 15 minutes, the cooling bath was removed and the reaction was stirred at room temperature for 1 hour and then at reflux for 3 hours. The cooled mixture was washed with NaHCO$_3$ solution and with brine, then was dried (Na$_2$SO$_4$) and evaporated. The residue was purified by chromatography over silica gel (ethyl acetate-toluene; 3:17) to yield 2.2 g of (E)-4-(4-chloro-1-butenyl)isoquinoline as an oil.

EXAMPLE 79

Preparation of (E)-1-[4-(4-isoquinolinyl)-3-butenyl]-1H-isoindole-1,3-(2H)-dione A mixture of 2.2 g of (E)-4-(4-chloro-1-butenyl) isoquinoline, 3.8 g of potassium phthalimide and 1.7 g of potassium iodide in 20 mL of dry dimethylformamide was maintained at 130° C. for 5 hours. After evaporation of the solvent, the residue was partitioned between dichloromethane and water. The dried (Na$_2$SO$_4$) organic layer was concentrated and the crude product was purified by chromatography over silica gel (ethyl acetate-toluene; 3:7) to yield 1.75 g of (E)-1-[4-(4-isoquinolinyl)-3-butenyl]-1H-isoindole-1,3-(2H)-dione, mp 135°–140°.

EXAMPLE 80

Preparation of (E)-4-(4-isoquinolinyl)-3-buten-1-amine

To a refluxing solution of 1.75 g of (E)-1-[4-(4-isoquinolinyl)-3-butenyl]-1H-isoindole-1,3-(2H)-dione in 80 mL of ethanol was added 1.1 mL of hydrazine hydrate and the reaction was stirred at reflux for 17 hours. The solvent was removed in vacuo and the residue was triturated with chloroform. The extract was concentrated to yield 1 g of (E)-4-(4-isoquinolinyl)-3-buten-1-amine as an oil.

EXAMPLE 81

Preparation of 4-isoquinolinebutanamine

A solution of 1 g of (E)-4-(4-isoquinolinyl)-3-buten-1-amine in 20 mL of ethanol was hydrogenated over 0.12 g of 10% Pd/C at room temperature and atmospheric pressure. After 8 hours, the catalyst was removed by filtration and the filtrate was concentrated to yield 0.893 g of 4-isoquinolinebutanamine.

EXAMPLE 82

(5-Carboxypentyl)triphenylphosphonium bromide

An intimate mixture of 6-bromohexanoic acid (19.5 g) and triphenylphosphine (26.3 g) was heated at 150° for three hours in a closed flask. After the reaction was cooled, the crude product was dissolved in chloroform (200 mL) and the resulting solution was diluted just to the cloud point with ether. The mixture was stored at 0° C. for several hours, then the solids were collected by filtration, washed with ether and dried in vacuo to yield 41.3 g of (5-carboxypentyl)triphenylphosphonium bromide, mp 197°–198° C. Anal. Calculated for C$_{24}$H$_{26}$BrO$_2$P: C, 63.03; H, 5.73; Br, 17.47. Found: C, 63.00; H, 5.76; Br, 17.54.

EXAMPLE 83

(7-Carboxyhexyl)triphenylphosphonium bromide 7-bromoheptanoic acid (19.7 g) and triphenylphosphine (22.1 g) were reacted together as in the previous example. Crystallization of the crude salt from chloroform-ether afforded 38.9 g of (7-carboxyhexyl)triphenylphosphonium bromide, mp 182°–183° C. Anal. Calculated for C$_{25}$H$_{28}$BrO$_2$P: C, 63.70; H, 5.99; Br, 16.95. Found: C, 63.31; H, 6.10; Br, 17.15.

EXAMPLE 84

(7-Carboxyheptyl)triphenylphosphonium bromide

Triphenylphosphine (26.3 g) and 8-bromooctanoic acid (21.3 g) were reacted as in Example 82. The crude salt was crystallized from a mixture of ethanol (100 mL), chloroform (200 mL) and ether (500 mL) to give 41 g of (7-carboxyheptyl) triphenylphosphonium bromide, mp 121°–123° C. Anal. Calculated for C$_{26}$H$_{30}$BrO$_2$P: C, 64.33; H, 6.23; Br, 16.46. Found: C, 63.97; H, 6.23; Br, 16.07.

EXAMPLE 85

3,3-Diphenyl-2-propenoic acid

In an inert atmosphere, sodium hydride (56% dispersion in oil; 4.3 g) was triturated with dry pentane and then was dispersed in dimethylsulfoxide (100 mL). After stirring at 70° C. for 1 hour, the solution was cooled to 0° C., then trimethyl phosphonoacetate (38.8 g) in dry tetrahydrofuran (100 mL) was added over 15 min. The reaction was stirred at 0° C. for 30 min, then benzophenone (15 g) was added and the mixture was stirred at room temperature for 16 hours and then at 50° C. for 4 hours to complete the reaction. After dilution with water, the mixture was extracted with ethyl acetate. The organic layer was washed with water, then was dried (MgSO$_4$) and evaporated. The residual oil was dissolved in methanol (150 mL) containing 10N sodium hydroxide (30 mL) and after the mixture was stirred at reflux for 16 hours, it was cooled, acidified with excess 1N hydrochoric acid solution and extracted with dichloromethane (3×150 mL). The combined extracts were washed with water, dried (Na$_2$SO$_4$) and evaporated. The crude product was passed through a short column of silica gel (200 g) using dichloromethane-ethyl acetate (1:1) as the eluant. The resulting material was crystallized from hexane to furnish 13.1 g of 3,3-diphenyl-2-propenoic acid, mp 162°–164° C.

EXAMPLE 86

4,4-diphenyl-3-butenoic acid

A mixture of diphenylacetaldehyde (19.6 g), malonic acid (10.9 g) and piperidine (0.4 mL) in pyridine (20 mL) was heated at reflux until the evolution of gas had subsided (1.25 h). The solution was cooled and poured into a stirred mixture of ice (100 g) and 2N hydrochloric acid (150 mL). The resulting solid was recovered by filtration, washed with water and dried to provide 23.1 g of 4,4-diphenyl-3-butenoic acid, mp 109°–111° C. A portion was crystallized from ethyl acetate-hexane to give the pure acid of 4,4-diphenyl-3-butenoic acid, mp 112.5°–114° C.

EXAMPLE 87

5,5-Diphenyl-4-pentenoic acid

In an inert atmosphere, sodium hydride (56% dispersion in oil; 9.5 g) triturated with pentane and then was dispersed in dry dimethylsulfoxide (100 mL). The mixture was stirred at 70° C. for 1 hour, then it was cooled to 0° C. and (3-carboxy-propyl)triphenylphosphonium chloride (35 g) was added in several portions over 5 min. The deep red solution was stirred at 0°–5° C. for 15 min, then a solution of benzophenone (19.86 g) in dry tetrahydrofuran (100 mL) was added at such a rate that the temperature did not exceed 25° C. The light brown reaction mixture was stirred at 16 hours at room temperature, then it was diluted with water (500 mL) and extracted with dichloromethane (3×200 mL). The organic extracts were discarded and the aqueous layer was acidified with 6N hydrochloric acid (40 mL) and extracted with dichloromethane (3×200 mL). The organic extracts were washed in turn with water (3×100 mL), then were combined, dried (MgSO4), decolorized with charcoal and evaporated in vacuo. The residue was passed through a short column of silica gel (150 g) made up in dichloromethane and the product was eluted with ethyl acetate-dichloromethane (1:1). After the appropriate fractions were concentrated, the residual solid was crystallized from ether-hexane to yield 14.3 g of 5,5-diphenyl-4-pentenoic acid, mp 80°–81.5° C.

EXAMPLE 88

5,5-bis(4-Fluorophenyl)-4-pentenoic acid

The reaction was performed as in Example 87 using sodium hydride (56% dispersion in oil; 9.5 g) dimethylsulfoxide (100 mL), (3-carboxypropyl)triphenylphosphonium chloride (35 g), 4,4'-difluorobenzophenone (23.8 g) and tetrahydrofuran (100 mL). After the usual work up, the crude product was crystallized from ether-hexane to furnish 18.2 g of 5,5-bis(4-fluorophenyl)-4-pentenoic acid, mp 100°–100° C. Anal. Calculated for $C_{17}H_{14}F_2O_2$: C, 70.82; H, 4.89. Found: C, 70.77; H, 5.00.

EXAMPLE 89

5,5-bis(4-Methoxyphenyl)-4-pentenoic acid

The reaction was performed as in Example 87 using sodium hydride (56% dispersion in oil; 9.5 g) dimethylsulfoxide (100 mL), (3-carboxypropyl)triphenylphosphonium chloride (35 g); 4,4'-dimethoxybenzophenone (26.4 g); and tetrahydrofuran (100 mL). After the usual work up, the crude acid was crystallized from dichloromethane-hexane to give 15.6 g of 5,5-bis(4-methoxyphenyl)-4-pentenoic acid, mp 113°–114° C. Anal. Calculated for $C_{19}H_{20}O_4$: C, 73.06; H, 6.45. Found: C, 73.00; H, 6.45.

EXAMPLE 90

6,6-Diphenyl-5-hexenoic acid

The reaction was carried out as in Example 87 using the following reagents: sodium hydride (56% dispersion in oil; 8.6 g), dimethylsulfoxide (100 mL), (4-carboxybutyl)triphenylphosphonium bromide (36.5 g), benzophenone (18.2 g), and tetrahydrofuran (100 mL). The crude product, isolated in the usual manner, was crystallized from hexane to give 16.5 g of 6,6-diphenyl-5-hexenoic acid, mp 111°–112.5° C. Anal. Calculated for $C_{18}H_{18}O_2$: C, 81.17; H, 6.81. Found: C, 81.39; H, 6.88.

EXAMPLE 91

7,7-Diphenyl-6-heptenoic acid

The reaction was carried out as in Example 87 using the following reagents: sodium hydride (56% dispersion in oil; 8.6 g); dimethylsulfoxide (100 mL), (5-carboxypentyl)triphenylphosphonium bromide (37.64 g); benzophenone (18 g) and tetrahydrofuran (100 mL). The acid, isolated in the normal manner, was crystallized from hexane to give 16.3 g of 7,7-diphenyl-6-heptenoic acid, mp 71.5°–72.5° C. A portion was recrystallized from hexane to give the analytical sample, mp 72.5°–73.5° C. Anal. Calculated for $C_{19}H_{20}O_2$: C, 81.40; H, 7.19. Found: C, 81.61; H, 7.40.

EXAMPLE 92

8,8-Diphenyl-7-octenoic acid

The reaction was carried out as in Example 87 using the following reagents: sodium hydride (56% dispersion in oil; 8.36 g); dimethylsulfoxide (100 mL), (6-carboxyhexyl)triphenylphosphonium bromide (37.7 g), benzophenone (17.5 g); and tetrahydrofuran (100 mL). The crude product, isolated in the usual way, was recrystallized from hexane (200 mL) to yield 16.6 g of 8,8-diphenyl-7-octenoic acid, mp 88°–89° C. Anal. Calculated for $C_{20}H_{22}O_2$: C, 81.60; H, 7.53. Found: C, 81.34; H, 7.25.

EXAMPLE 93

9,9-Diphenyl-8-nonenoic acid

The reaction was carried out as in Example 87 using the following reagents: sodium hydride (56% dispersion in oil; 8.6 g), dimethylsulfoxide (100 mL), (7-carboxyheptyl)triphenylphosphonium bromide (39.95 g), benzophenone (18.2 g), and tetrahydrofuran (100 mL). The crude acid, isolated in the usual manner, required further purification by HPLC (hexane-ether; 3:2). The appropriate fractions were combined and evaporated and the residue was crystallized from hexane to provide 14.1 g of 9,9-diphenyl-8-nonenoic acid, mp 77.5°–78.5° C. Anal. Calculated for $C_{21}H_{24}O_2$: C, 81.78; H, 7.84. Found: C, 81.71; H, 7.70.

EXAMPLE 94

3,3-Diphenyl-N-[4-(3-pyridinyl)butyl]-2-propenamide

To a stirred solution of 3,3-diphenyl-2-propenoic acid (6.23 g), and triethylamine (4.25 mL) in dry tetrahydrofuran (40 mL) at 0° C., was added a solution of ethyl chloroformate (2.74 mL) in tetrahydrofuran (20 mL) dropwise such that the reaction temperature was maintained at 0° C. After the addition was completed, the reaction was stirred at 0° C. for 15 min, then a solution of 3-pyridinebutanamine (4.38 g), in tetrahydrofuran (20 mL) was added dropwise while keeping the reaction at −50° C. The mixture was stirred at 0° C. for 1 hour and then at room temperature for 2 hours before the precipitated triethylamine hydrochloride was removed by filtration. The evaporated filtrate was partitioned between 1N hydrochloric acid solution (80 mL) and ether (80 mL). After the ethereal extract was discarded, the aqueous layer was basified with 4N sodium hydroxide (30 mL) and extracted with ether (4×100 mL). Evaporation of the dried ($K_2CO_3$) organic extracts afforded 11.1 g of amide which was purified by HPLC (ethyl acetate) to yield 7.42 g of 3,3-diphenyl-N-[4-(3-pyridinyl)butyl]-2-propenamide. A portion was crystallized from ether to give the analytical sample, mp 78°–80° C. Anal. Calculated for $C_{24}H_{24}N_2O$: C, 80.87; H, 6.79; N, 7.86. Found: C, 81.11; H, 6.86; N, 7.89.

The amine (6.8 g) in 2-propanol (20 mL) was treated with 2.1N hydrobromic acid in 2-propanol (9 mL) and the solution was diluted with ethyl acetate to give 7.9 g of 3,3-diphenyl-N-[4-(3-pyridinyl)butyl]-2-propenamide HBr salt (1:1), mp 173°–174.5° C. Anal. Calculated for $C_{24}H_{24}N_2O \cdot HBr$: C, 65.91; H, 5.76; N, 6.40; Br, 18.27. Found: C, 65.93; H, 5, 98; N, 6.53; Br, 18.14.

EXAMPLE 95

3,3-Diphenyl-N-[6-(3-pyridinyl)hexyl]-2-propenamide

As in Example 94, the mixed anhydride formed from 3,3-diphenyl-2-propenoic acid (4.49 g), triethylamine (3 mL; 0.0215 mol) and ethyl chloroformate (1.97 mL) in tetrahydrofuran (44 mL) was reacted with 3-pyridine-hexanamine (3.74 g). The material obtained after the usual work up was purified by HPLC (ether-hexane; 7:3) and then crystallized from ether to give 4.45 g of 3,3-diphenyl-N-[6-(3-pyridinyl)hexyl]-2-propenamide, mp 73°–74° C. Anal. Calculated for $C_{26}H_{28}N_2O$: C, 81.21; H, 7.34; N, 7.29. Found: C, 80.98; H, 7.42; N, 7.07.

EXAMPLE 96

4,4-Diphenyl-N-[4-(3-pyridinyl)butyl]-3-butenamide

A solution of 4,4-diphenyl-3-butenoic acid (10.15 g) 3-pyridinebutanamine (6.4 g) and 1,3-dicyclohexylcarbodiimide (8.8 g) in dichloromethane (100 mL) was stirred at ambient temperature for 10 days. The precipitated dicyclohexylurea was filtered off, then the evaporated filtrate was partitioned between 1N hydrochloric acid (150 mL) and ethyl acetate (2×50 mL). The aqueous layer was basified with 10N sodium hydroxide and extracted with ethyl acetate. Concentration of the dried (MgSO$_4$) organic extract furnished 5.1 g of crude amide which was purified by HPLC (ether-hexane; 2:1) to yield 3.4 g of 4,4-diphenyl-N-[4-(3-pyridinyl)butyl]-3-butenamide. A portion was crystallized from ether to give the analytical sample, 69°–70° C. Anal. Calculated for $C_{25}H_{26}N_2O$: C, 81.05; H, 7.07; N, 7.56 Found: C, 80.92; H, 6.90; N, 7.58.

EXAMPLE 97

5,5-Diphenyl-N-[4-(3-pyridiyl)butyl]-4-pentenamide

Treatment of 5,5-diphenyl-4-pentenoic acid (30.3 g) with thionyl chloride (30 mL) at room temperature for 15 min followed by evaporation from toluene provided the acid chloride. A solution of the acid chloride in dichloro- methane (125 mL) was added over 15 min to a stirred solution of 3-pyridinebutanamine (18 g) in dichloromethane (125 mL) maintained at 0° C. The resulting mixture was allowed to equilibrate to room temperature over 1 hour and then excess 1N sodium hydroxide solution was added. The phases were separated and the organic layer was washed with water, dried ($Na_2SO_4$) and evaporated. The residue was purified by HPLC (ethyl acetate-triethylamine; 49:1) to afford 45.1 g of 5,5-diphenyl-N-[4-(3-pyridinyl)butyl]-4-pentenamide as a pale yellow oil. Anal. Calculated for $C_{26}H_{28}N_2O$: C, 81.21; H, 7.34; N, 7.29 Found: C, 80.96; H, 7.61; N, 7.15.

EXAMPLE 98

5,5-bis(4-Methoxyphenyl)-N-[4-(3-pyridinyl)butyl]-4-pentenamide

As in Example 94, the mixed anhydride formed from 5,5-bis(4-methoxyphenyl)-4-pentenoic acid (8.68 g), triethylamine (4.25 mL) and ethyl chloroformate (2.74 mL) in tetrahydrofuran (60 mL) was reacted with 3-pyridine-butanamine (4.38 g). The material obtained from the usual work up was purified by HPLC (ethyl acetate-triethylamine; 49:1) to give 9.4 g of 5,5-bis(4-methoxyphenyl)-N-[4-(3-pyridinyl)butyl]-4-pentenamide as an oil. Anal. Calculated for $C_{28}H_{32}N_2O_3$: C, 75.65; H, 7.26; N, 6.30 Found: C, 75.70; H, 7.15; N, 6.20.

EXAMPLE 99

5,5-bis(4-Fluorophenyl)-N-[4-(3-pyridinyl)butyl]-4-pentenamide

As in Example 94, the mixed anhydride formed from 5,5-bis(4-fluorophenyl)-4-pentenoic acid (8 g) triethylamine (4.25 mL; 0.0305 mol) and ethyl chloroformate (2.74 mL; 0.0278 mol) in tetrahydrofuran (60 mL) was treated with 3-pyridine-butanamine (4.38 g). The crude product obtained after the usual work up was purified by HPLC (ethyl acetate-triethylamine; 49:1) to give, 10.1 g of 5,5-bis(4-fluorophenyl)-N-[4-(3-pyridinyl)butyl]-4-pentenamide as an oil. Anal. Calculated for $C_{26}H_{26}F_2N_2O$: C, 74.26; H, 6.23; N, 6.66 Found: C, 73.99; H, 6.20; N, 6.44.

EXAMPLE 100

N-[4-(1H-Imidazol-1-yl)butyl]-5,5-diphenyl-4-pentenamide

As in Example 94, the mixed anhydride formed from 5,5-diphenyl-4-pentenoic acid (5.05 g) triethylamine (3 mL) and ethyl chloroformate (1.97 mL) in tetrahydrofuran (44 mL) was reacted with 1H-imidazole-1-butanamine (3.74 g). The material obtained from the usual work up was purified by HPLC (ethyl acetate-methanol-triethylamine; 45:3:2) and then crystallized from ethyl acetate-hexane to provide 2.25 g of N-[4-(1H-imidazol-1-yl)butyl]-5,5-diphenyl-4-pentenamide, mp 102°–103° C. Anal. Calculated for $C_{24}H_{27}N_3O$: C, 77.17; H, 7.29; N, 11.25 Found: C, 77.36; H, 7.35; N, 11.36

EXAMPLE 101

6,6-Diphenyl-N-[4-(3-pyridinyl)butyl)-5-hexenamide

As in Example 94, the mixed anhydride formed from 6,6-diphenyl-5-hexenoic acid (7.4 g), triethylamine (4.25 mL) and ethyl chloroformate (2.74 mL) in tetrahydrofuran (60 mL) was reacted with 3-pyridinebutanamine (4.38 g). The material obtained after the usual work up was purified by HPLC (ethyl acetate-triethylamine; 49:1) to provide 8.2 g of 6,6-biphenyl-N-[4-(3-pyridinyl)butyl]-5-hexenamide as an oil. Anal. Calculated for $C_{27}H_{30}N_2O$: C, 81.37; H, 7.59; N, 7.03 Found: C, 81.27; H, 7.59; N, 7.06.

EXAMPLE 102

7,7-Diphenyl-N-[4-(3-pyridinyl)butyl]-6-heptenamide

As in Example 94, the mixed anhydride formed from 7,7-diphenyl-6-heptenoic acid (7.8 g) triethylamine (4.25 mL) and ethyl chloroformate (2.74 mL) in tetrahydrofuran (60 mL) was reacted with 3-pyridinebutanamine (4.38 g). The material obtained after the usual work up was purified by HPLC (ethyl acetate-triethylamine; 49:1) to furnish 9.85 g of 7,7-biphenyl-N-[4-(3-pyridinyl)butyl]-6-heptenamide as an oil. Anal. Calculated for $C_{28}H_{32}N_2O$: C, 81.51; H, 7.82; N, 6.79 Found: C, 81.56; H, 7.67; N, 6.77.

EXAMPLE 103

8,8-Diphenyl-N-[4-(3-pyridinyl)butyl]-7-octenamide

As in Example 94, the mixed anhydride formed from 8,8-diphenyl-7-octenoic acid (8.18 g) triethylamine (4.25 mL) and ethyl chloroformate (2.74 mL) in tetrahydrofuran (60 mL) was reacted with 3-pyridinebutanamine (4.38 g). The material obtained after the usual work up was purified by HPLC (ethyl acetate-triethylamine; 49:1) to afford 8.95 g of 8,8-biphenyl-N-[4-(3-pyridinyl)butyl]-7-octenamide as an oil.

The product was characterized as its (1:1) hydrobromide salt, mp 98.5°-102° C., that had been crystallized from 2-propanol-ethyl acetate. Anal. Calculated for $C_{29}H_{34}N_2O \cdot HBr$: C, 68.63; H, 6.95; Br, 15.75; N, 5.52 Found: C, 68.48; H, 6.68; Br, 15.92; N, 5.52.

EXAMPLE 104

9,9-Diphenyl-N-[4-(3-pyridinyl)butyl]-8-nonenamide

As in Example 94, the mixed anhydride formed from 9,9-diphenyl-8-nonenoic acid (8.75 g) triethylamine (4.25 mL) and ethyl chloroformate (2.74 mL) in tetrahydrofuran (60 mL) was reacted with 3-pyridinebutanamine (4.38 g). The material obtained after the usual work up was purified by HPLC (ethyl acetate-triethylamine; 49:1) to give 8.3 g of 9,9-biphenyl-N-[4-(3-pyridinyl)butyl)-8-nonenamide as an oil. Anal. Calculated for $C_{30}H_{36}N_2O$: C, 81.78; H, 8.24; N, 6.36 Found: C, 81.89; H, 8.21; N, 6.40.

EXAMPLE 105

N-(5,5-Diphenyl-4-pentenyl)-3-pyridinebutanamine and its (1:1) (E)-2-butenedioate salt A solution of 5,5-diphenyl-N-[4-(3-pyridinyl)butyl]-4-pentenamide (40.1 g) in toluene (250 mL) was added in a slow stream with stirring to a chilled 3.5M solution of sodium bis(2-methoxyethoxy)aluminum hydride in toluene (101.5 mL). After the mixture was stirred at 50° C. for 2 hours, it was cooled in an ice-water bath and excess 4N sodium hydroxide solution was added. The separated aqueous layer was extracted with toluene and the organic layers were washed with brine, then were dried ($Na_2SO_4$) and evaporated to furnish 35.9 g of crude amine. The material was purified by HPLC (ethyl acetate-methanol-triethylamine; 95:5:2) to yield 23 g of N-(5,5-diphenyl-4-pentenyl)-3-pyridinebutanamine as an oil. The amine (5 g) in methanol was treated with fumaric acid (1.6 g) and ethyl acetate was added to the boiling solution to the cloud point. The resulting salt was recrystallized from methanol-ethyl acetate to provide 6.2 g of N-(5,5-diphenyl-4-pentenyl)-3-pyridinebutanamine (1:1)-(E)-2-butenedioate salt, mp 160°-161° C. (dec). Anal. Calculated for $C_{26}H_{30}N_2 \cdot C_4H_4O_4$: C, 74.05; H, 7.04; N, 5.76 Found: C, 74.02; H, 7.03; N, 5.89.

EXAMPLE 106

N-(5,5-Diphenyl-4-pentenyl)-N-[4-(3-pyridinyl)butyl]-formamide

A mixture of N-(5,5-diphenyl-4-pentenyl)-3-pyridinebutanamine (10 g) and 98% formic acid (6 mL) in toluene (50 mL) was refluxed for 2 hours through a Soxhlet extractor charged with 4 A molecular sieves. The cooled solution was washed in turn with water, saturated sodium carbonate solution and brine. The dried ($Na_2SO_4$) toluene layer was evaporated to give 9.5 g of crude amide which was purified by HPLC (ethyl acetate-triethylamine; 49:1) to furnish 8.5 g of N-(5,5-diphenyl-4-pentenyl)-N-[4-(3-pyridinyl)butyl]-formamide as a colorless oil. Anal. Calculated for $C_{27}H_{30}N_2O$: C, 81.37; H, 7.59; N, 6.96 Found: C, 81.50; H, 7.64; N, 6.96.

EXAMPLE 107

N-(5,5-Diphenyl-4-pentenyl)-N-methyl-3-pyridinebutanamine ethanedioate 0.25 molar hydrate A solution of N-(5,5-diphenyl-4-pentenyl)-N-[4-(3-pyridinyl)butyl]formamide (4.5 g) in toluene (50 mL) was added dropwise with stirring to a 3.5M solution of sodium bis(2-methoxyethoxy)aluminum hydride in toluene (13 mL; 0.0455 mol) at 50° C. After 30 min the cooled solution was treated with excess 4N sodium hydroxide solution and the separated aqueous phase was extracted with toluene. The organic layers were washed with brine, then were combined, dried ($Na_2SO_4$) and evaporated to afford 4.2 g of crude amine. This material (4.2 g) in methanol was treated with oxalic acid dihydrate (1.4 g) and ethyl acetate was added to the boiling solution just to the cloud point. The resulting solids were recrystallized from methanol-ethyl acetate to provide 4.6 g of N-(5,5-diphenyl-4-pentenyl)-N-methyl-3-pyridinebutanamine ethanedioate 0.25 molar hydrate mp 118°-119° C. Anal. Calculated for $C_{27}H_{32}N_2 \cdot C_2H_2O_4 \cdot 0.25H_2O$: C, 72.70; H, 7.26; N, 5.85 Found: C, 72.78; H, 7.20; N, 5.84.

EXAMPLE 108

1-Butyl-3,4-dihydro-6-methoxynaphthalene

A solution of 2.5M n-butyl lithium in hexane (160 mL) was added to a stirred mixture of 6-methoxytetralone (70.5 g) in diethyl ether (500 mL) maintained at 10° C. The reaction was stirred at room temperature overnight, then water (20 mL) was added dropwise over several minutes followed by 2N HCl (200 mL). The phases were separated and the aqueous layer was extracted with diethyl ether (2×250 mL). The combined organic extracts were dried ($MgSO_4$) and evaporated to give 80 g of a mixture (~1:1) of 1-butyl-1-hydroxy-6-methoxytetralin and the starting ketone as an oil.

A solution of the crude material (80 g) in chloroform (250 mL) containing trifluoroacetic acid (25 mL) was stirred at ambient temperature for 16 hours then the solvents were removed under reduced pressure. The residue was partitioned between dichloromethane (500 mL) and 1N sodium hydroxide solution (200 mL) and the separated aqueous layer was extracted with dichloromethane (100 mL). The organic extracts were washed in turn with brine, then were combined, dried ($MgSO_4$) and concentrated in vacuo. The resulting oil was passed through a column of silica gel (400 g) made up in hexane and eluted with hexane. Evaporation of the fractions (3×500 mL) containing the non-polar product furnished 34.9 g of 1-butyl-3,4-dihydro-6-methoxynaphthalene as an oil.

EXAMPLE 109

1-Butyl-3,4-dihydro-6-methoxy-2-naphthalenecarboxaldehyde

Phosphorus oxychloride (16.6 mL) was added dropwise with stirring to dimethylformamide (70 mL) at −5° C. After the addition was completed, the mixture was stirred at 0° C. for 15 minutes, then a solution of 1-butyl-3,4-dihydro-6-methoxy-naphthalene (34.9 g) in dimethylformamide (30 mL) was added slowly over 15 minutes while the reaction temperature was maintained at 0° C. The cooling bath was then withdrawn and after the mixture had stirred at room temperature for 1.5 hours, a few chips of ice were added, followed, after 5 minutes, by 10N sodium hydroxide (200 mL). The reaction was heated to 110° C. which caused the vigorous evolution of dimethylamine from the mixture and after 10 minutes the reaction was cooled, diluted with water (750 mL) and extracted with dichloromethane (1×500 mL; 2×300 mL). The organic layers were washed in turn with water (2×200 mL), then were combined, dried (MgSO$_4$) and evaporated to furnish an amber oil which was passed through a short column of silica gel (200 g) in dichloromethane. The fractions containing the product were evaporated to yield 39.4 g of crude 1-butyl-3,4-dihydro-6-methoxy-2-naphthalene-carboxaldehyde as an oil.

EXAMPLE 110

1-Butyl-6-methoxy-2-naphthalenecarboxaldehyde

1-Butyl-3,4-dihydro-6-methoxy-2-naphthalenecarboxaldehyde (4.6 g) and 2,3-dichloro-4,5-dicyano-1,4-benzoquinone (5.43 g) were stirred together in benzene (100 mL) at reflux for 5.5 hours. The reaction was then cooled and after the precipitated hydroquinone was filtered off, the filtrate was washed with 1N sodium hydroxide (3×75 mL). Each aqueous layer was backwashed with benzene (50 mL), then the combined organic extracts were dried (MgSO$_4$) and evaporated to provide 4.2 g of product. Crystallization of the material from 2-propanol afforded 3.1 g of 1-butyl-6-methoxy-2-naphthalenecarboxaldehyde as a light tan solid, mp 56°–57° C. A sample was recrystallized from the same solvent to yield the analytical specimen, mp 57°–58° C. Anal. Calcd for $C_{16}H_{18}O_2$: C, 79.31; H, 7.49 Found: C, 79.32; H, 7.44

EXAMPLE 111

(E)-3-(1-Butyl-6-methoxy-2-naphthalenyl)-2-propenoic acid methyl ester

A solution of 1-butyl-6-methoxy-2-naphthalenecarboxaldehyde (1.6 g) and (carbomethoxymethylene)-triphenyl- phosphorane (2.45 g) in dichloromethane (20 mL) was stirred at room temperature for 40 hours. The solvent was removed in vacuo and the residue was triturated with a mixture of diethyl ether (20 mL) and hexane (50 mL). After the resulting solid was filtered off, the filtrate was evaporated and the residue was passed through a column of silica gel (20 g) made up in diethyl ether-hexane (1:9). Evaporation of the appropriate fractions furnished 1.75 g of (E)-3-(1-butyl-6-methoxy-2-naphthalenyl)-2-propenoic acid methyl ester. A sample was crystallized from hexane to give the analytical sample, mp 71°–72° C. Anal. Calcd for $C_{19}H_{22}O_3$: C, 76.48; H, 7.43 Found: C, 76.23; H, 7.46

EXAMPLE 112

(E)-3-(1-Butyl-6-methoxy-2-naphthalenyl)-2-propenoic acid

A solution of (E)-3-(1-butyl-6-methoxy-2-naphthalenyl)-2-propenoic acid methyl ester (1.7 g) in methanol (10 mL) was treated with 2N sodium hydroxide (4.5 mL) and the mixture was stirred at reflux for 1 hour. The warm reaction mixture was acidified by the addition of 1N hydrochloric acid (9.2 mL). After the mixture cooled, the resulting solid was filtered off to provide 1.6 g of (E)-3-(1-butyl-6-methoxy-2-naphthalenyl)-2-propenoic acid. Crystallization of a portion from methanol gave the analytical specimen, mp 163°–164° C. Anal. Calcd for $C_{18}H_{20}O_3$: C, 76.03; H, 7.09 Found: C, 76.31; H, 7.32

EXAMPLE 113

(E)-3-(1-Butyl-6-methoxy-2-naphthalenyl)-2-propenoic acid 4-nitrophenyl ester

A stirred mixture of (E)-3-(1-butyl-6-methoxy-2-naphthalenyl)-2-propenoic acid (1.5 g) and 4-nitrophenol (0.81 g) in dichloromethane, was cooled in an ice bath, during the addition of a solution of 1,3-dicyclohexyl- carbodiimide (1.1 g) in dichloromethane (5 mL) then the reaction was stirred at room temperature over the weekend. After the precipitated dicyclohexylurea was removed by filtration, the filtrate was concentrated and applied to a column of silica gel (25 g) made up in dichloromethane-hexane (2:1). Elution with the same solvent mixture and concentration of the appropriate fractions yielded 2 g of (E)-3-(1-butyl-6-methoxy-2-naphthalenyl)-2-propenoic acid 4-nitrophenyl ester. Crystallization of the material from 2-propanol gave 1.85 g of the active ester, mp 140°–141° C. Anal. Calcd for $C_{24}H_{23}NO_5$: C, 71.10; H, 5.72; N, 3.45 Found: C, 70.98; H, 5.50; N, 3.33

EXAMPLE 114

[R-(E)]-3-(1-Butyl-6-methoxy-2-naphthalenyl)-N-[1-methyl-4-(3-pyridinyl)butyl]-2-propenamide A solution of [(E)-3-(1-butyl-6-methoxy-2-naphthalenyl]-2-propenoic acid 4-nitrophenyl ester (1.8 g) and (R)-α-methyl-3-pyridinebutanamine (0.73 g) in tetrahydrofuran (25 mL) at room temperature for 42 hours. After the solvent was removed in vacuo, the residue was dissolved in dichloromethane (75 mL) and washed with 0.5N sodium hydroxide solution (3×50 mL). The aqueous layers were back washed in turn with dichloromethane (50 mL) and then the combined extracts were dried (K$_2$CO$_3$) and evaporated. The crude product was purified by HPLC (ethyl acetate) and then was crystallized from dichloromethane-hexane to yield 1.5 g of [R-(E)]-3-(1-butyl-6-methoxy-2-naphthalenyl]-N-[1-methyl-4-(3-pyridinyl)butyl]-2-propenamide, mp 159°–160° C. Anal. Calcd for $C_{28}H_{34}N_2O_2$: C, 78.10; H, 7.96; N, 6.51 Found: C, 78.42; H, 7.93; N, 6.45

EXAMPLE 115

(E)-3-(1-Butyl-3,4-dihydro-6-methoxy-2-naphthalenyl)-2-propenoic acid methyl ester As in Example 111, 1-butyl-3,4-dihydro-6-methoxy-2-naphthalenecarboxaldehyde (3.05 g) and (carbomethoxymethylene)triphenylphosphorane (4.5 g) in dichloromethane (25 mL) was stirred at room temperature for 64 hours. The usual work up furnished 2.9 g of (E)-3-(1-butyl-3,4-dihydro-6-methoxy-2-naphthalenyl)-2-propenoic acid methyl ester as an oil.

EXAMPLE 116

(E)-3-(1-Butyl-3,4-dihydro-6-methoxy-2-naphthalenyl)-2-propenoic acid

As in Example 112, (E)-3-(1-butyl-3,4-dihydro-6-methoxy-2-naphthalenyl)-2-propenoic acid methyl ester (2.9 g) in methanol (12 mL) was treated with 2N sodium hydroxide solution (7 mL) at reflux for 1.5 hours. The usual work up provided 2.6 g of (E)-3-(1-butyl-3,4-dihydro-6-methoxy-2-naphthalenyl)-2-propenoic acid as an oil.

EXAMPLE 117

(E)-3-(1-Butyl-3,4-dihydro-6-methoxy-2-naphthalenyl)-2-propenoic acid 4-nitrophenyl ester As in Example 113, (E)-3-(1-butyl-3,4-dihydro-6-methoxy-2-naphthalenyl)-2-propenoic acid (1.8 g) was reacted with 4-nitrophenol (0.97 g) in dichloromethane (30 mL) in the presence of 1,3-dicyclohexylcarbodiimide (1.3 g) overnight at room temperature. The normal work up yielded 1.5 g of crude ester. Crystallization from diethyl ether-2-propanol furnished (E)-3-(1-butyl-3,4-dihydro-6-methoxy-2-naphthalenyl)-2-propenoic acid 4-nitrophenyl ester, mp 94°–95° C. Anal. Calcd for $C_{24}H_{25}NO_5$: C, 70.74; H, 6.18; N, 3.44 Found: C, 70.42; H, 6.04; N, 3.29

EXAMPLE 118

[(R-(E)]-3-(1-Butyl-3,4-dihydro-6-methoxy-2-naphthalenyl)-N-[1-methyl-4-(3-pyridinyl)butyl]-2-propenamide As in Example 114, (E)-3-(1-butyl-3,4-dihydro-6-methoxy-2-naphthalenyl)-2-propenoic acid 4-nitrophenyl ester (1.1 g) was treated with (R)-α-methyl-3-pyridinebutanamine (0.45 g) in tetrahydrofuran (10 mL) at room temperature for 24 hours and then at 50° C. for 4 hours. The crude product was purified by HPLC (ethyl acetate) to afford 1.05 g of [R-(E)]-3-(1-butyl-3,4-dihydro-6-methoxy-2-naphthalenyl)-N-[1-methyl-4-(3-pyridinyl)butyl]-2-propenamide as an amorphous solid. Anal. Calcd for $C_{28}H_{36}N_2O_2$: C, 77.74; H, 8.39; N, 6.47 Found: C, 77.22; H, 8.71; N, 6.32

EXAMPLE 119

3,4-Dihydro-6-methoxy-1-(4-methoxyphenyl)naphthalene

A solution of 4-methoxyphenyl magnesium bromide, freshly prepared in the normal manner in tetrahydrofuran (200 mL) from 4-bromoanisole (101 g) and magnesium metal (14.5 g), was added over 45 minutes with stirring to a chilled (0° C.) solution of 6-methoxytetralone (85 g) in dry tetrahydrofuran (500 mL). After the addition was completed, the reaction was stirred at room temperature for 2 hours and the excess reagent was destroyed by the careful addition of water (50 mL). Most of the solvent was removed in vacuo and the concentrate was partitioned between ethyl acetate and 1N sodium hydroxide. After the resultant solids were filtered off, the layers were separated and the organic layer was washed with brine, then was dried (MgSO₄) and evaporated to give 123 g of crude carbinol as an oil. A solution of the above carbinol (100 g) in toluene (800 mL) containing p-toluenesulfonic acid (1 g) was refluxed for 3 hours in a flask equipped with a Dean-Stark trap. The cooled solution was washed with 10% sodium bicarbonate solution and with brine, then was dried (MgSO₄) and evaporated. The residual material was passed though a short column of silica gel (250 g) made up in dichloromethane-hexane (1:3) and the product was eluted with dichloromethane-hexane (1:1). Evaporation of the appropriate fractions and crystallization of the residue from toluene-hexane (2x) gave 37.1 g of 3,4-dihydro-6-methoxy-1-(4-methoxyphenyl)naphthalene, mp 100.5°–102° C.

EXAMPLE 120

3,4-Dihydro-6-methoxy-1-(4-methoxyphenyl)-2-naphthalenecarboxaldehyde

As in Example 109, 3,4-dihydro-6-methoxy-1-(4-methoxyphenyl)naphthalene (17 g) was added to the reagent formed from the addition of phosphorus oxychloride (6.54 mL) to dimethylformamide (35 mL) at −5° C. The cooling bath was then withdrawn and after the mixture had stirred at 35° C. for 1.5 hours, a few chips of ice were added followed after 5 minutes by 10N sodium hydroxide (70 mL). After the reaction was heated to 110° C. for 10 minutes the reaction was cooled and the resulting solid was filtered off, washed with water and dried in vacuo to give 18.75 g of 3,4-dihydro-6-methoxy-1-(4-methoxyphenyl)-2-naphthalenecarboxaldehyde, mp 104°–105° C. Crystallization of a portion from diethyl ether furnished the pure aldehyde, mp 105°–106° C. Anal. Calcd for $C_{19}H_{18}O_3$: C, 77.53; H, 6.16 Found: C, 77.62; H, 6.20

EXAMPLE 121

(E)-3-[3,4-Dihydro-6-methoxy-1-(4-methoxyphenyl)-2-naphthalenyl]-2-propenoic acid methyl ester As in Example 111, 3,4-dihydro-6-methoxy-1-(4-methoxyphenyl)-2-naphthalenecarboxaldehyde (2.94 g) and (carbomethoxymethylene)triphenylphosphorane (3.7 g) in dichloromethane (30 mL) was stirred at room temperature for 64 hours. After the normal work up, the crude product was crystallized from 2-propanol to afford 2.65 g of (E)-3-[3,4-dihydro-6-methoxy-1-(4-methoxyphenyl)-2-naphthalenyl]-2-propenoic acid methyl ester, mp 116°–118° C. Anal. Calcd for $C_{22}H_{22}O_4$: C, 75.41; H, 6.33 Found: C, 75.55; H, 6.23

EXAMPLE 122

(E)-3-[3,4-Dihydro-6-methoxy-1-(4-methoxyphenyl)-2-naphthalenyl]-2-propenoic acid As in Example 112, (E)-3-[3,4-dihydro-6-methoxy-1-(4-methoxyphenyl)-2-naphthalenyl]-2-propenoic acid methyl ester (2.5 g) in methanol (15 mL) was heated at reflux with 1N sodium hydroxide solution (11 mL) at reflux for 1 hour. The usual work up furnished 2 g of (E)-3-[3,4-dihydro-6-methoxy-1-(4-methoxyphenyl)-2-naphthalenyl]-2-propenoic acid. Crystallization of a small sample from dichloromethane-ethyl acetate gave the analytical specimen, mp 222°–224° C. Anal. Calcd for $C_{21}H_{20}O_4$: C, 74.98; H, 5.99 Found: C, 74.89; H, 6.00

EXAMPLE 123

(E)-3-[3,4-Dihydro-6-methoxy-1-(4-methoxyphenyl)-2-naphthalenyl]-2-propenoic acid 4-nitrophenyl ester As in Example 113, (E)-3-[3,4-dihydro-6-methoxy-1-(4-methoxyphenyl)-2-naphthalenyl]-2-propenoic acid (1.7 g) was reacted with 4-nitrophenol (0.775 g) in dichloromethane (25 mL) in the presence of 1,3-dicyclohexylcarbodiimide (1.04 g) overnight at room temperature. After the normal work up, the crude ester was triturated with diethyl ether and then crystallized from 2-propanol to give 1 g of (E)-3-[3,4-dihydro-6-methoxy-1-(4-methoxyphenyl)-2-naphthalenyl]-2-propenoic acid 4-nitrophenyl ester as a yellow solid, mp 151°–152° C. Anal. Calcd for $C_{27}H_{23}NO_6$: C, 70.89; H, 5.07; N, 3.06 Found: C, 70.52; H, 5.10; N, 3.08

EXAMPLE 124

[(R-(E)]-3-[3,4-Dihydro-6-methoxy-1-(4-methoxyphenyl)-2-naphthalenyl]-N-[1-methyl-4-(3-pyridinyl)butyl]-2-propenamide As in Example 114, (E)-3-[3,4-dihydro-6-methoxy-1-(4-methoxyphenyl)-2-naphthalenyl]-2-propenoic acid 4-nitrophenyl ester (0.71 g) was treated with (R)-α-methyl-3-pyridinebutanamine (0.33 g) in tetrahydrofuran (5 mL) at room temperature for 24 hours. The crude product was purified by HPLC (ethyl acetate) to yield 0.625 g of [R-(E)]-3-[3,4-dihydro-6-methoxy-1-(4-methoxyphenyl)-2-naphthalenyl]-N-[1-methyl-4-(3-pyridinyl)butyl]-2-propenamide as an amorphous solid. Anal. Calcd for $C_{31}H_{32}N_2O_3 \cdot 0.25H_2O$: C, 76.43; H, 7.14; N, 5.75; $H_2O$, 0.93 Found: C, 76.51; H, 7.15; N, 5.70; $H_2O$, 1.04

EXAMPLE 125

6-Methoxy-1-(4-methoxyphenyl)-2-naphthalenecarboxaldehyde

As in Example 110, 3,4-dihydro-6-methoxy-1-(4-methoxyphenyl)-2-naphthalenecarboxaldehyde (9.7 g) and 2,3-dichloro-4,5-dicyano-1,4-benzoquinone (9.36 g) were stirred together in benzene (150 mL) at reflux for 17 hours. The usual workup provided 9.5 g of crude product which was crystallized from 2-propanol to give 7.4 g of 6-methoxy-1-(4-methoxyphenyl)-2-naphthalenecarboxaldehyde, mp 99°–101° C. Anal. Calcd for $C_{19}H_{16}O_3$: C, 78.06; H, 5.52 Found: C, 78.05; H, 5.59

EXAMPLE 126

(E)-3-[6-Methoxy-1-(4-methoxyphenyl)-2-naphthalenyl]-2-propenoic acid methyl ester As in Example 111, 6-methoxy-1-(4-methoxyphenyl)-2-naphthalenecarboxaldehyde (2.92 g) and (carbomethoxymethylene)triphenylphosphorane (3.7 g) in dichloromethane (30 mL) was stirred at room temperature for 18 hours. After the normal work up, the crude product was crystallized from diethyl ether-hexane to provide 1.95 g of (E)-3-[6-methoxy-1-(4-methoxyphenyl)-2-naphthalenyl]-2-propenoic acid methyl ester. Recrystallization of a sample from the same solvents furnished the pure aldehyde, mp 118°–121° C. Anal. Calcd for $C_{22}H_{22}O_4$: C, 75.84; H, 5.79 Found: C, 75.79; H, 5.86

EXAMPLE 127

(E)-3-[6-Methoxy-1-(4-methoxyphenyl)-2-naphthalenyl]-2-propenoic acid

As in Example 112, (E)-3-[6-methoxy-1-(4-methoxyphenyl)-2-naphthalenyl]-2-propenoic acid methyl ester (1.8 g) in methanol (10 mL) was heated at reflux with 1N sodium hydroxide solution (8 mL) for 1 hour. The usual work up provided 1.6 g of (E)-3-[6-methoxy-1-(4-methoxyphenyl)-2-naphthalenyl]-2-propenoic acid. Crystallization of a small portion from dichloromethane-ethyl acetate gave the analytical sample, mp 248°–249° C. Anal. Calcd for $C_{21}H_{18}O_4$: C, 75.43; H, 5.43 Found: C, 75.65; H, 5.70

EXAMPLE 128

(E)-3-[6-Methoxy-1-(4-methoxyphenyl)-2-naphthalenyl]-2-propenoic acid 4-nitrophenyl ester As in Example 113, (E)-3-[6-methoxy-1-(4-methoxyphenyl)-2-naphthalenyl]-2-propenoic acid (1.4 g) was reacted with 4-nitrophenol (0.64 g) in dichloromethane (25 mL) in the presence of 1,3-dicyclohexylcarbodiimide (0.87 g) overnight at room temperature to give, after the normal work up and crystallization of the crude product from 2-propanol, 1.6 g of (E)-3-[6-methoxy-1-(4-methoxyphenyl)-2-naphthalenyl]-2-propenoic acid 4-nitrophenyl ester, mp 160°–161° C. Anal. Calcd for $C_{27}H_{21}NO_6$: C, 71.20; H, 4.65; N, 3.08 Found: C, 70.87; H, 4.89; N, 3.06

EXAMPLE 129

[(R-(E)]-3-[6-Methoxy-1-(4-methoxyphenyl)-2-naphthalenyl]-N-[1-methyl-4-(3-pyridinyl)butyl]-2-propenamide As in Example 114, (E)-3-[6-methoxy-1-(4-methoxyphenyl)-2-naphthalenyl]-2-propenoic acid 4-nitrophenyl ester (1.37 g) was treated with (R)-α-methyl-3-pyridinebutanamine (0.51 g) in tetrahydrofuran (10 mL) at room temperature for 24 hours. The crude amide was purified by HPLC (ethyl acetate) to yield 1.15 g of [R-(E)]-3-[6-methoxy-1-(4-methoxyphenyl)-2-naphthalenyl]-N-[1-methyl-4-(3-pyridinyl)butyl]-2-propenamide as an amorphous solid. Anal. Calcd for $C_{31}H_{32}N_2O_3 \cdot 0.25H_2O$: C, 76.75; H, 6.75 N, 5.77; $H_2O$, 0.97 Found: C, 76.69; H, 6.63; N, 5.73; $H_2O$, 1.05

EXAMPLE 130

4-Acetoxy-1-butyl-5-methoxy-2-naphthalenecarboxylic acid ethyl ester and
4-acetoxy-1-butyl-7-methoxy-2-naphthalenecarboxylic acid ethyl ester To a solution of potassium t-butoxide (25 g) in t-butanol (180 mL) at 60° C. was added a mixture of diethyl succinate (52.3 g) and 1-(3-methoxyphenyl)pentanone (38.5 g) at a rapid dropwise rate and the reaction was refluxed with stirring for 2.5 hours. After the solvent was removed under reduced pressure, the residue was dissolved in water (250 mL) and extracted with diethyl ether (3×150 mL) to remove neutral materials. The aqueous layer was then acidified and extracted with dichloromethane (3×200 mL) to yield, after evaporation of the dried (MgSO$_4$) organic extracts, 61.3 g of a mixture of the isomeric 3-(ethoxycarbonyl)-4-(3-methoxyphenyl)-3-octenoic acids as an oil. A solution of the above mixture of acids (15 g) and sodium acetate (3.9 g) in acetic anhydride (90 mL) was heated at reflux for 4 hours. The solvent was removed in vacuo and the residue was partitioned between dichloromethane (200 mL) and 10% potassium carbonate solution (100 mL). The dried (MgSO$_4$) organic layer was concentrated and the resulting mixture was separated by using HPLC (diethyl ether-hexane; 1:3). Evaporation of the appropriate fractions furnished two isomeric compounds weighing 7.2 g and 2.7 g respectively. Crystallization of the major component from hexane afforded pure 4-acetoxy-1-butyl-7-methoxy-2-naphthalenecarboxylic acid ethyl ester, mp 70°–71.5° C. Anal. Calcd for C$_{20}$H$_{24}$O$_5$: C, 69.75; H, 7.02 Found: C, 69.57; H, 7.05.

Crystallization of the more polar minor isomer from hexane gave 4-acetoxy-1-butyl-5-methoxy-2-naphthalenecarboxylic acid ethyl ester, mp 86°–88° C. Anal. Calcd for C$_{20}$H$_{24}$O$_5$: C, 69.75; H, 7.02 Found: C, 69.47; H, 7.24

EXAMPLE 131

1-Butyl-4-hydroxy-5-methoxy-2-naphthalenecarboxylic acid ethyl ester

A solution of 4-acetoxy-1-butyl-5-methoxy-2-naphthenecarboxylic acid ethyl ester (3.3 g) in 1.05M ethanolic hydrogen chloride (35 mL) was heated at reflux for 1.5 hour and then the solvent was removed under reduced pressure. Crystallization of the residual material from hexane provided 2.5 g of 1-butyl-4-hydroxy-5-methoxy-2-naphthalenecarboxylic acid ethyl ester, mp 80°–82° C. Anal. Calcd for C$_{18}$H$_{22}$O$_4$: C, 71.50; H, 7.33 Found: C, 71.21; H, 7.48

EXAMPLE 132

1-Butyl-5-methoxy-4-[(1-phenyl-1H-tetrazole-5-yl)oxy]-2-naphthalenecarboxylic acid ethyl ester Potassium t-butoxide (1.03 g) was added to a solution of 1-butyl-4-hydroxy-5-methoxy-2-naphthalenecarboxylic acid ethyl ester (2.4 g) and 5-chloro-1-phenyl-1H-tetrazole (1.55 g) in dimethylformamide (20 mL) and the reaction was stirred at room temperature for 1.25 hours. After the solvent was removed in vacuo, the residual material was partitioned between dichloromethane (150 mL) and water (75 mL). The separated aqueous layer was re-extracted with dichloromethane, and after each organic extract was washed with water, they were combined, dried (Na$_2$SO$_4$) and evaporated. Crystallization of the crude product from diethyl ether-hexane gave 2.15 g of 1-butyl-5-methoxy-4-[(1-phenyl-1H-tetrazole-5-yl)oxy]-2-naphthalenecarboxylic acid ethyl ester, mp 144°–146° C. A portion was recrystallized from the same solvents to provide the analytical sample, mp 145°–146° C. Anal. Calcd for C$_{25}$H$_{26}$N$_4$O$_4$: C, 67.25; H, 5.87; N, 12.55 Found: C, 67.07; H, 5.99; N, 12.51

EXAMPLE 133

1-Butyl-5-methoxy-2-naphthalenecarboxylic acid ethyl ester

A solution of 1-butyl-5-methoxy-4-[(1-phenyl-1H-tetrazole-5-yl)oxy]-2-naphthalenecarboxylic acid ethyl ester in a mixture of tetrahydrofuran (25 mL) and ethanol (75 mL) was hydrogenated over 10% palladium on carbon (1.3 g) at 50° C. and three atmospheres. After the uptake of hydrogen had stopped, the catalyst was removed by filtration and the filtrate was concentrated to dryness. The resulting material was dissolved in diethyl ether (150 mL) and the solution extracted with 1N sodium hydroxide (2×50 mL). After the base extracts were backwashed with diethyl ether, the combined organic layers were dried (MgSO$_4$) and evaporated to yield 3.6 g of 1-butyl-5-methoxy-2-naphthalenecarboxylic acid ethyl ester as an oil. A portion was distilled on a Kugelrohr apparatus (140° C.; 0.1 mm) to furnish the analytical sample. Anal. Calcd for C$_{18}$H$_{22}$O$_3$: C, 75.50; H, 7.74 Found: C, 75.02; H, 7.97

EXAMPLE 134

1-Butyl-5-methoxy-2-naphthalenecarboxylic acid

As in Example 112, 1-butyl-5-methoxy-2-naphthalenecarboxylic acid ethyl ester (3.45 g) in methanol (40 mL) was saponified with 2N sodium hydroxide solution (10 mL) at reflux for 1.75 hours. 3.1 g of crude acid, mp 151°–153° C., was obtained from the usual work up and crystallization of a sample from diethyl ether-hexane gave 1-butyl-5-methoxy-2-naphthalenecarboxylic acid, mp 154°–155° C. Anal. Calcd for C$_{16}$H$_{18}$O$_3$: C, 74.39; H, 7.02 Found: C, 74.05; H, 7.05

EXAMPLE 135

1-Butyl-5-methoxy-2-naphthalenemethanol

A solution of borane in tetrahydrofuran (1M; 10 mL) was added to a solution of 1-butyl-5-methoxy-2-naphthalenecarboxylic acid in tetrahydrofuran (15 mL) at 0°–5° C. and the mixture was stirred at room temperature for 3 hours. After the solvent was evaporated off, the reaction was diluted with 1N sodium hydroxide and extracted with dichloromethane. The organic layer was washed with brine then was dried (MgSO$_4$), evaporated and crystallized from hexane to give 1.58 g of 1-butyl-5-methoxy-2-naphthalenemethanol, mp 100°–102° C. Recrystallization of a portion from diethyl ether-hexane afforded the pure alcohol, 101°–102° C. Anal. Calcd for C$_{16}$H$_{20}$O$_2$: C, 78.65; H, 8.25 Found: C, 78.36; H, 8.33

EXAMPLE 136

1-Butyl-5-methoxy-2-naphthalenecarboxaldehyde

A solution of dimethylsulfoxide (0.54 mL) in dry dichloromethane (3 mL) was added with stirring to a chilled (<−60° C.) solution of oxalyl chloride (0.59 mL) in dry dichloromethane (15 mL) at such a rate that the reaction temperature did not exceed −60° C. After 15 minutes a solution of 1-butyl-5-methoxy-2-naphthalenemethanol (1.54 g) in dichloromethane (6 mL) was added while the reaction temperature was still maintained below −60° C. The reaction was allowed to proceed for 15 minutes then triethylamine (2.9 mL) was added to the chilled reaction and, after an additional 20 minutes the cooling bath was removed and the mixture was allowed to equilibrate to room temperature. After 2N hydrochloric acid (225 mL) was added, the layers were separated and the aqueous phase was extracted with dichloromethane (50 mL), then the combined organic extracts were dried (MgSO$_4$) and evaporated to yield 1.6 g of 1-butyl-5-methoxy-2-naphthalenecarboxaldehyde. Sublimation of a portion (50° C.; 0.1 mm) furnished the analytical sample, mp 61.5°–62.5° C. Anal. Calcd for C$_{16}$H$_{18}$O$_2$: C, 79.31; H, 7.49 Found: C, 79.02; H, 7.53

EXAMPLE 137

(E)-3-(1-Butyl-5-methoxy-2-naphthalenyl)-2-propenoic acid methyl ester

As in Example 111, 1-butyl-5-methoxy-2-naphthalenecarboxaldehyde (1.5 g) and (carbomethoxymethylene)triphenylphosphorane (2.13 g) in dichloromethane (20 mL) was stirred at room temperature for 42 hours to provide, after the usual work up, 1.75 g of (E)-3-(1-butyl-5-methoxy-2-naphthalenyl)-2-propenoic acid methyl ester. Crystallization of a sample from hexane provided the pure ester, mp 53.5°–54.5° C. Anal. Calcd for $C_{22}H_{22}O_4$: C, 76.48; H, 7.43 Found: C, 76.53; H, 7.34

EXAMPLE 138

(E)-3-(1-Butyl-5-methoxy-2-naphthalenyl)-2-propenoic acid

As in Example 112, (E)-3-(1-butyl-5-methoxy-2-naphthalenyl)-2-propenoic acid methyl ester (1.65 g) in methanol (10 mL) was treated with 2N sodium hydroxide solution (6 mL) at reflux for 2 hours. A sample of the acid (1.55 g) obtained from the usual work up was crystallized from diethyl ether to give pure (E)-3-(1-butyl-5-methoxy-2-naphthalenyl)-2-propenoic acid, mp 202°–204° C. Anal. Calcd for $C_{18}H_{20}O_3$: C, 76.03; H, 7.09 Found: C, 75.95 H, 7.19

EXAMPLE 139

(E)-3-(1-Butyl-5-methoxy-2-naphthalenyl)-2-propenoic acid 4-nitrophenyl ester

As in Example 113, (E)-3-(1-butyl-5-methoxy-2-naphthalenyl)-2-propenoic acid (1.4 g) was reacted with 4-nitrophenol (0.76 g) in dichloromethane (25 mL) in the presence of 1,3-dicyclohexylcarbodiimide (1.02 g) to give 1.51 g of (E)-3-(1-butyl-5-methoxy-2-naphthalenyl)-2-propenoic acid 4-nitrophenyl ester. Crystallization of a portion from diethyl ether afforded the analytical sample, mp 115°–116° C. Anal. Calcd for $C_{24}H_{23}NO_5$: C, 71.10; H, 5.72; N, 3.45 Found: C, 71.25; H, 5.75; N, 3.39

EXAMPLE 140

[(R-(E)]-3-(1-Butyl-5-methoxy-2-naphthalenyl)-N-[1-methyl-4-(3-pyridinyl)butyl]-2-propenamide As in Example 114, (E)-3-(1-butyl-5-methoxy-2-naphthalenyl)-2-propenoic acid 4-nitrophenyl ester (1.4 g) was reacted with (R)-α-methyl-3-pyridinebutanamine (0.575 g) in tetrahydrofuran (25 mL) at room temperature for 17 hours. The product was isolated in the usual way and then was crystallized from ethyl acetate-hexane to afford 1.18 g of [R-(E)]-3-(1-butyl-5-methoxy-2-naphthalenyl)-N-[1-methyl-4-(3-pyridinyl)butyl]-2-propenamide, mp 138°–139° C. Anal. Calcd for $C_{29}H_{36}N_2O_3$: C, 78.10; H, 7.96; N, 6.51 Found: C, 77.81; H, 7.96; N, 6.60

EXAMPLE 141

1-Butyl-4-hydroxy-7-methoxy-2-naphthalenecarboxylic acid ethyl ester

As in Example 131, a solution of 4-acetoxy-1-butyl-7-methoxy-2-naphthenecarboxylic acid ethyl ester (9.1 g) in 1.05M ethanolic hydrogen chloride (100 mL) was heated at reflux for 2.5 hours. After removal of the solvent the residue was crystallized from hexane to give 6.5 g. of 1-butyl-4-hydroxy-7-methoxy-2-naphthalenecarboxylic acid ethyl ester, mp 112°–115° C. Recrystallization of a sample from hexane afforded the analytical specimen, mp 114°–115° C. Anal. Calcd for $C_{18}H_{22}O_4$: C, 71.50; H, 7.09 Found: C, 71.21; H, 7.39

EXAMPLE 142

1-Butyl-7-methoxy-4-[(1-phenyl-1H-tetrazole-5-yl)oxy]-2-naphthalenecarboxylic acid ethyl ester As in Example 132, 1-butyl-4-hydroxy-7-methoxy-2-naphthalenecarboxylic acid ethyl ester (2.9 g) was reacted with 5-chloro-1-phenyl-1H-tetrazole (1.87 g) in dimethylformamide (25 mL) in the presence of potassium t-butoxide (1.25 g). After 0.5 hours at room temperature, the reaction was worked up in the described manner and the crude product was crystallized from diethyl ether-hexane to afford 2.9 g of 1-butyl-7-methoxy-4-[(1-phenyl-1H-tetrazole-5-yl)oxy]-2-naphthalenecarboxylic acid ethyl ester, mp 94°–96° C. A sample was recrystallized from the same solvents to provide the analytical specimen, mp 95.5°–96.5° C. Anal. Calcd for $C_{25}H_{26}N_4O_4$: C, 67.25; H, 5.87; N, 12.55 Found: C, 67.16; H, 5.99; N, 12.66

EXAMPLE 143

1-Butyl-7-methoxy-2-naphthalenecarboxylic acid ethyl ester

As in Example 133, 1-butyl-7-methoxy-4-[(1-phenyl-1-H-tetrazole-5-yl)oxy]-2-naphthalenecarboxylic acid ethyl ester (2.85 g) was hydrogenolyzed in ethanol (100 mL) over 10% palladium on carbon (0.57 g) at 50° C. and three atmospheres to give, after the usual work up, 1.5 g of crude 1-butyl-7-methoxy-2-naphthalenecarboxylic acid ethyl ester as an oil. The material was combined with 4.8 g of crude product from another experiment and was purified by HPLC (diethyl ether-hexane; 1:9) to give 5.8 g of pure ester.

EXAMPLE 144

1-Butyl-7-methoxy-2-naphthalenecarboxylic acid

As in Example 112, 1-butyl-7-methoxy-2-naphthalenecarboxylic acid ethyl ester (5.4 g) in methanol (40 mL) was reacted with 2N sodium hydroxide solution (20 mL) at reflux for 2 hours to give, after the normal work up, 4.9 g of crude acid. Crystallization of the material from diethyl ether-hexane furnished 4.22 g of 1-butyl-7-methoxy-2-naphthalenecarboxylic acid, mp 123°–125° C. Anal. Calcd for $C_{16}H_{18}O_3$: C, 74.39; H, 7.02 Found: C, 74.27; H, 6.93

EXAMPLE 145

1-Butyl-7-methoxy-2-naphthalenemethanol

As in Example 135, 1-butyl-7-methoxy-2-naphthalenecarboxylic acid (2.73 g) in tetrahydrofuran (15 ml) was treated with a solution of borane in tetrahydrofuran (1M; 22 mL) at 0°–5° C. and then mixture was stirred at room temperature overnight. The product was isolated in the usual manner and was crystallized from hexane to give 2.32 g of 1-butyl-7-methoxy-2-naphthalenemethanol, mp 52°–53° C. Anal. Calcd for $C_{16}H_{20}O_2$: C, 78.65; H, 8.25 Found: C, 78.50; H, 8.12

EXAMPLE 146

1-Butyl-7-methoxy-2-naphthalenecarboxaldehyde

As in Example 136, 1-butyl-7-methoxy-2-naphthalenemethanol (2.25 g) was oxidized by using the reagent prepared from dimethylsulfoxide (0.54 mL) and oxalyl chloride (0.9 mL) in dry dichloromethane (25 mL). The usual work up gave 2 g of 1-butyl-7-methoxy-2-naphthalenecarboxaldehyde and distillation of a sample on a Kugelrohr apparatus (138°–140° C.; 0.1 mm)

furnished the analytical specimen. Anal. Calcd for $C_{16}H_{18}O_2$: C, 79.31; H, 7.49 Found: C, 79.11; H, 7.49

EXAMPLE 147

(E)-3-(1-Butyl-7-methoxy-2-naphthalenyl)-2-propenoic acid methyl ester

As in Example 111, 1-butyl-7-methoxy-2-naphthalenecarboxaldehyde (1.7 g) and (carbomethoxymethylene)triphenylphosphorane (2.85 g) in dichloromethane (20 mL) was stirred at room temperature for 42 hours to give after the normal work up, 1.6 g of (E)-3-(1-butyl-7-methoxy-2-naphthalenyl)-2-propenoic acid methyl ester as an oil.

EXAMPLE 148

(E)-3-(1-Butyl-7-methoxy-2-naphthalenyl)-2-propenoic acid

As in Example 112, (E)-3-(1-butyl-7-methoxy-2-naphthalenyl)-2-propenoic acid methyl ester (1.55 g) in methanol (20 mL) was treated with 2N sodium hydroxide solution (4 mL) at reflux for 2 hours and the normal isolation procedure afforded 1.45 g of (E)-3-(1-butyl-7-methoxy-2-naphthalenyl)-2-propenoic acid. Crystallization of a sample from diethyl ether gave the analytical specimen. Anal. Calcd for $C_{18}H_{20}O_3$: C, 76.03; H, 7.09 Found: C, 75.66; H, 7.13

EXAMPLE 149

(E)-3-(1-Butyl-7-methoxy-2-naphthalenyl)-2-propenoic acid 4-nitrophenyl ester

As in Example 113, (E)-3-(1-butyl-7-methoxy-2-naphthalenyl)-2-propenoic acid (1.35 g) was reacted with 4-nitrophenol (0.73 g) in dichloromethane (25 mL) in the presence of 1,3-dicyclohexylcarbodiimide (0.99 g) to give 1.6 g of (E)-3-(1-butyl-7-methoxy-2-naphthalenyl)-2-propenoic acid 4-nitrophenyl ester. Crystallization of a portion from diethyl ether furnished the analytical sample, mp 114°-115° C. Anal. Calcd for $C_{24}H_{23}NO_5$: C, 71.10; H, 5.72; N, 3.45 Found: C, 70.85; H, 5.56; N, 3.24

EXAMPLE 150

[(R-(E)]-3-(1-Butyl-7-methoxy-2-naphthalenyl)-N-[1-methyl-4-(3-pyridinyl)butyl]-2-propenamide As in Example 114, (E)-3-(1-butyl-7-methoxy-2-naphthalenyl)-2-propenoic acid 4-nitrophenyl ester (1.73 g) was treated with (R)-α-methyl-3-pyridinebutanamine (0.71 g) in tetrahydrofuran (25 mL) at room temperature overnight. The product was isolated in the described manner and then crystallized from ethyl acetate-hexane to furnish 1.32 g of [R-(E)]-3-(1-butyl-7-methoxy-2-naphthalenyl)-N-[1-methyl-4-(3-pyridinyl)-butyl]-2-propenamide, mp 127°-128° C. Anal. Calcd for $C_{28}H_{34}N_2O_2$: C, 78.10; H, 7.96; N, 6.51 Found: C, 77.79; H, 8.01; N, 6.55

EXAMPLE 151

1-Butyl-4,7-dimethoxy-2-naphthalenecarboxylic acid ethyl ester

A solution of 1-butyl-4-hydroxy-7-methoxy-2-naphthalenecarboxylic acid ethyl ester (6.5 g) and methyl iodide (7 mL) in acetone (65 mL) containing potassium carbonate (5 g) was stirred at room temperature for 64 hours. After the reaction mixture was filtered, the filtrate was concentrated to dryness and the residue was partitioned between dichloromethane (150 mL) and water (100 mL). The dried ($MgSO_4$) organic layer was evaporated and the residual material crystallized from 2-propanol to yield 5.35 g of 1-butyl-4,7-dimethoxy-2-naphthalenecarboxylic acid ethyl ester, mp 44°-45° C. Anal. Calcd for $C_{19}H_{24}O_3$: C, 72.13; H, 7.64 Found: C, 72.03; H, 7.78

EXAMPLE 152

1-Butyl-4,7-dimethoxy-2-naphthalenecarboxaldehyde

N-methylpiperazine (8.3 mL) in toluene (15 mL) was added dropwise over 5 minutes to a chilled (−5° C.) mixture of sodium bis(2-methoxyethoxy)aluminum hydride in toluene (3.4M; 20.6 mL) and toluene (25 mL). This solution was added to a stirred solution of 1-butyl-4,7-dimethoxy-2-naphthalenecarboxylic acid ethyl ester (4 g) in toluene (50 mL) at −40° C. After 5 hours the cooling bath was removed and the reaction was allowed to equilibrate to −15° C. over 45 minutes, whereupon conc. hydrochloric acid (30 mL) was added slowly to destroy excess reagent. The mixture was diluted with ice cold 1N hydrochloric acid (200 mL), and after the phases were separated, the aqueous layer was extracted with toluene (2×150 mL). The combined organic extracts were dried ($MgSO_4$) and evaporated to yield 1.35 g of crude 1-butyl-4,7-dimethoxy-2-naphthalenecarboxaldehyde as an oil. This material was used in subsequent reactions without further purification.

EXAMPLE 153

(E)-3-(1-Butyl-4,7-dimethoxy-2-naphthalenyl)-2-propenoic acid

As in Example 111, 1-butyl-4,7-dimethoxy-2-naphthalenecarboxaldehyde (1.35 g) and (carbomethoxymethylene)triphenylphosphorane (1.35 g) in dichloromethane (10 mL) was stirred at room temperature for 42 hours. The crude ester obtained from the usual work up was dissolved in methanol (25 mL) containing 1N sodium hydroxide solution (4 mL) and heated at reflux for 2 hours. The normal isolation procedure furnished 0.725 g of (E)-3-(1-butyl-4,7-dimethoxy-2-naphthalenyl)-2-propenoic acid. A portion was crystallized from diethyl ether-hexane to give the analytical specimen, mp 174°-176° C. Anal. Calcd for $C_{19}H_{22}O_4$: C, 72.59; H, 7.05 Found: C, 72.58; H, 7.18

EXAMPLE 154

(E)-3-(1-Butyl-4,7-dimethoxy-2-naphthalenyl)-2-propenoic acid 4-nitrophenyl ester As in Example 113, (E)-3-(1-butyl-4,7-dimethoxy-2-naphthalenyl)-2-propenoic acid (0.71 g) was treated with 4-nitrophenol (0.35 g) in dichloromethane (10 mL) in the presence of 1,3-dicyclohexylcarbodiimide (0.475 g) to furnish, after the normal work up and crystallization of the crude product from 2-propanol, 1.17 g of (E)-3-(1-butyl-4,7-dimethoxy-2-naphthalenyl)-2-propenoic acid 4-nitrophenyl ester., mp 144°-145.5° C. Anal. Calcd for $C_{25}H_{25}NO_6$: C, 68.95; H, 5.79; N, 3.22 Found: C, 69.05; H, 5.74; N, 3.25

EXAMPLE 155

[(R-(E)]-3-(1-Butyl-4,7-dimethoxy-2-naphthalenyl)-N-[1-methyl-4-(3-pyridinyl)butyl]-2-propenamide As in Example 114, (E)-3-(1-butyl-4,7-dimethoxy-2-naphthalenyl)-2-propenoic acid 4-nitrophenyl ester (1 g) was reacted with (R)-α-methyl-3-pyridinebutanamine (0.385 g) in tetrahydrofuran (15 mL) at room temperature for 17 hours. The product was isolated in the usual manner and crystallized twice from ethyl acetate-hexane to provide 0.65 g of [R-(E)]-3-(1-butyl-4,7-dimethoxy-2-naphthalenyl)-N-[1-methyl-4-(3-pyridinyl)-butyl]-2-propenamide, mp 168°-169° C. Anal. Calcd for $C_{29}H_{36}N_2O_3$: C, 75.62; H, 7.88; N, 6.08 Found: C, 75.33; H, 7.65; N, 6.12

EXAMPLE 156

4-Acetoxy-1-butyl-2-naphthalenecarboxylic acid ethyl ester

As in Example 130, 1-phenylpentanone (50 g) was reacted with diethyl succinate (80.5 g) in t-butanol at 60° C. for 6 hours in the presence of potassium t-butoxide (38 g). The normal work up furnished 81 g of a mixture of the isomeric 3-(ethoxycarbonyl)-3-octenoic acids as an oil. The acids (79.4 g) were cyclized as before by refluxing in acetic anhydride (500 mL) containing sodium acetate (22.5 g) for 9 hours. After work up, the crude product was passed through a short column of silica gel (650 g) made up in dichloromethane-hexane (2:1) to give 60 g of 4-acetoxy-1-butyl-2-naphthalenecarboxylic acid ethyl ester as an oil.

EXAMPLE 157

1-Butyl-4-hydroxy-2-naphthalenecarboxylic acid ethyl ester

As in Example 131, a solution of 4-acetoxy-1-butyl-2-naphthenecarboxylic acid ethyl ester (60 g) in 1M ethanolic hydrogen chloride (500 mL) was heated at reflux for 0.75 hours. After the solvent was evaporated, the residue was crystallized from hexane to give 46.6 g of 1-butyl-4-hydroxy-2-naphthalenecarboxylic acid ethyl ester, mp 117°-120° C. Recrystallization of a portion from hexane gave the pure ester, mp 118°-119° C. Anal. Calcd for $C_{17}H_{20}O_4$: C, 74.97; H, 7.40 Found: C, 75.02; H, 7.35

EXAMPLE 158

1-Butyl-4-methoxy-2-naphthalenecarboxylic acid ethyl ester

1-Butyl-4-hydroxy-2-naphthalenecarboxylic acid ethyl ester (27 g) was reacted with methyl iodide (17 mL) in acetone (200 mL) containing potassium carbonate (13.8 g) with stirring at room temperature for 24 hours. The crude product obtained after the usual work up was distilled on a Kugelrohr apparatus (135°-138° C.; 0.1 mm) to provide 25.8 g of 1-butyl-4-methoxy-2-naphthalenecarboxylic acid ethyl ester as oil. Anal. Calcd for $C_{18}H_{22}O_3$: C, 75.50; H, 7.74 Found: C, 75.36; H, 7.84

EXAMPLE 159

1-Butyl-4-methoxy-2-naphthalenecarboxaldehyde

As in Example 152, a solution of 1-butyl-4-methoxy-2-naphthalenecarboxylic acid ethyl ester (8.6 g) in toluene (100 mL) was reacted with the reagent formed from the addition of N-methylpiperazine (19.6 mL) to a mixture of sodium bis(2-methoxyethoxy)aluminum hydride in toluene (3.4M; 49 mL) and toluene (90 mL) at −45° C. for 2 hours and then at −15° C. for 1 hour. The usual work up gave 7.5 g of crude aldehyde, which was crystallized from 2-propanol to provide 4.1 g of 1-butyl-4-methoxy-2-naphthalenecarboxaldehyde, mp 51°-52° C. Anal. Calcd for $C_{16}H_{18}O_2$: C, 79.31; H, 7.49 Found: C, 79.56; H, 7.59

EXAMPLE 160

(E)-3-(1-Butyl-4-methoxy-2-naphthalenyl)-2-propenoic acid methyl ester

As in Example 111, 1-butyl-4-methoxy-2-naphthalenecarboxaldehyde (4.05 g) and (carbomethoxymethylene)triphenylphosphorane (6 g) in dichloromethane (40 mL) was stirred at room temperature for 42 hours. Crystallization of the crude reaction product from the normal work up gave 4.1 g of (E)-3-(1-butyl-4-methoxy-2-naphthalenyl)-2-propenoic acid methyl ester, mp 63°-64° C. Anal. Calcd for $C_{19}H_{22}O_3$: C, 76.48; H, 7.43 Found: C, 75.89; H, 7.26

EXAMPLE 161

(E)-3-(1-Butyl-4-methoxy-2-naphthalenyl)-2-propenoic acid

As in Example 112, (E)-3-(1-butyl-4-methoxy-2-naphthalenyl)-2-propenoic acid methyl ester (4 g) in methanol (20 mL) was treated with 2N sodium hydroxide solution (5 mL) at reflux for 1 hour and the normal isolation procedure afforded 3.8 g of (E)-3-(1-butyl-4-methoxy-2-naphthalenyl)-2-propenoic acid. Crystallization of a sample from diethyl ether gave the analytical specimen, mp 166°-167° C. Anal. Calcd for $C_{18}H_{20}O_3$: C, 76.03; H, 7.09 Found: C, 75.89; H, 7.13

EXAMPLE 162

(E)-3-(1-Butyl-4-methoxy-2-naphthalenyl)-2-propenoic acid 4-nitrophenyl ester

As in Example 113, (E)-3-(1-butyl-4-methoxy-2-naphthalenyl)-2-propenoic acid (3.7 g) was reacted with 4-nitrophenol (1.99 g) in dichloromethane (40 mL) in the presence of 1,3-dicyclohexylcarbodiimide (2.7 g). The crude reaction product was crystallized from 2-propanol to give 4.63 g of (E)-3-(1-butyl-4-methoxy-2-naphthalenyl)-2-propenoic acid 4-nitrophenyl ester, mp 121.5°-122.5° C. Anal. Calcd for $C_{24}H_{23}NO_5$: C, 71.10; H, 5.72; N, 3.45 Found: C, 70.93; H, 5.77; N, 3.52

EXAMPLE 163

[(R-(E)]-3-(1-Butyl-4-methoxy-2-naphthalenyl)-N-[1-methyl-4-(3-pyridinyl)butyl]-2-propenamide As in Example 114, (E)-3-(1-butyl-4-methoxy-2-naphthalenyl)-2-propenoic acid 4-nitrophenyl ester (2.03 g) was reacted with (R)-α-methyl-3-pyridinebutanamine (0.83 g) in tetrahydrofuran (30 mL) at room temperature overnight. The product was isolated in the usual manner and crystallized from ethyl acetate-hexane to provide 1.76 g of [R-(E)]-3-(1-butyl-4-methoxy-2-naphthalenyl)-N-[1-methyl-4-(3-pyridinyl)butyl]-2-propenamide, mp 133°-134° C. Anal. Calcd for $C_{28}H_{34}N_2O_2$: C, 78.10; H, 7.96; N, 6.51 Found: C, 78.18; H, 8.06; N, 6.49

EXAMPLE 164

(E)-3-(1-Butyl-4-methoxy-2-naphthalenyl)-N-[6-(5-pyrimidinyl)hexyl]-2-propenamide As in Example 114, (E)-3-(1-butyl-4-methoxy-2-naphthalenyl)-2-propenoic acid 4-nitrophenyl ester (1.21 g) was reacted with 5-pyrimidinehexanamine (0.505 g) in tetrahydrofuran (20 mL) at room temperature overnight and then at 50° C. for 1.5 hour. The product was isolated in the usual manner then was purified by HPLC (ethyl acetate) and twice crystallized from ethyl acetate-hexane to provide 0.86 g of (E)-3-(1-butyl-4-methoxy-2-naphthalenyl)-N-[6-(5-pyrimidinyl)hexyl]-2- propenamide, mp 128°–129° C. Anal. Calcd for $C_{28}H_{35}N_3O_2$: C, 75.47; H, 7.92; N, 9.43 Found: C, 75.52; H, 7.95; N, 9.40

EXAMPLE 165

2-Hydroxyethyl-3,3-bis(3-methoxyphenyl)-2-propenoic acid ethyl ester

As described in Example 135, a solution of 3-carboethoxy-4,4-bis(3-methoxyphenyl)-3-butenoic acid (20.5 g) in dry tetrahydrofuran (100 mL) was treated with a solution of 1M borane in tetrahydrofuran (57 mL) and the reaction was stirred at room temperature overnight. After the usual work up, the crude product was purified by HPLC (diethyl etherhexane; 65:35) to provide 15.4 g of 2-hydroxyethyl-3,3-bis(3-methoxyphenyl)-2-propenoic acid ethyl ester, mp 102.5°–103.5° C. Anal. Calcd for $C_{19}H_{20}O_3$: C, 77.00; H, 6.80 Found: C, 77.12; H, 6.69

EXAMPLE 166

7-Methoxy-1-(3-methoxyphenyl)-2-naphthalenecarboxylic acid ethyl ester

A solution of dimethylsulfoxide (3.8 mL) in dry dichloromethane (10 mL) was added with stirring to a chilled ($< -60°$ C.) solution of oxalyl chloride (4 mL) in dry dichloromethane (80 mL) at such a rate that the reaction temperature did not exceed $-60°$ C. After 15 minutes a solution of 2-hydroxyethyl-3,3-bis(3-methoxyphenyl)-2-propenoic acid ethyl ester (15 g) in dichloromethane (20 mL) was added while the reaction temperature was still maintained below $-60°$ C. The reaction was allowed to proceed for 15 minutes then triethylamine (27 mL) was added to the chilled reaction and after an additional 20 minutes the cooling bath was removed and the mixture was allowed to equilibrate to room temperature. After 2N hydrochloric acid (100 mL) was added, the layers were separated and the aqueous phase was extracted with dichloromethane (25 mL), then the combined organic extracts were dried (MgSO$_4$) and evaporated to yield 14.8 g of the crude aldehyde. The crude material was dissolved in dichloromethane (100 mL) containing trifluoroacetic acid (1 mL) and was left at room temperature for 4 hours. The usual work up gave 13 g of crude acid which was purified by HPLC (ethyl acetate-hexane; 1:4) to provide 7 g of 7-methoxy-1-(3-methoxyphenyl)-2-naphthalenecarboxylic acid ethyl ester contaminated with a minor amount (~12%) of the corresponding 5-methoxy isomer. This material was used in subsequent transformations without further purification.

EXAMPLE 167

7-Methoxy-1-(3-methoxyphenyl)-2-naphthalenecarboxylic acid

A solution of crude 7-methoxy-1-(3-methoxyphenyl)-2-naphthalenecarboxylic acid ethyl ester (4.1 g) in a mixture of methanol (20 mL) and 4N potassium hydroxide (5 mL) was heated at reflux for 3 hours. After the methanol was evaporated off, the reaction was diluted with water and extracted with ether (2×25 mL). The aqueous layer was acidified, extracted with dichloromethane (3×25 mL) and the dried (MgSO$_4$) extracts evaporated to give 3.9 g of crude 7-methoxy-1-(3-methoxyphenyl)-2-naphthalenecarboxylic acid. Crystallization from toluene-hexane provided 3.05 g of acid, mp 164°–168° C. Anal. Calcd for $C_{19}H_{16}O_4$: C, 74.01; H, 5.23 Found: C, 73.58; H, 5.49

EXAMPLE 168

7-Methoxy-1-(3-methoxyphenyl)-2-naphthalenemethanol

A solution of borane in tetrahydrofuran (1M; 10 mL) was added to a solution of crude 7-methoxy-1-(3-methoxyphenyl)-2-naphthalenecarboxylic acid (2 g) in tetrahydrofuran (10 mL) at 0°–5° C. and the mixture was stirred at room temperature for 3 hours. After the solvent was evaporated off, the reaction was diluted with 1N sodium hydroxide and extracted with dichloromethane. The organic layer was washed with brine then was dried (MgSO$_4$) and evaporated to give 1.75 g of crude 7-methoxy-1-(3-methoxyphenyl)-2-naphthalenemethanol.

EXAMPLE 169

7-Methoxy-1-(3-methoxyphenyl)-2-naphthalenecarboxaldehyde

7-Methoxy-1-(3-methoxyphenyl)-2-naphthalenemethanol (1.75 g) was oxidized using the reagent prepared as in Example 136 from oxalyl chloride (0.62 mL) and dimethylsulfoxide (0.9 mL) in dichloromethane (14 mL). The usual work up furnished 1.6 g of 7-methoxy-1-(3-methoxyphenyl)-2-naphthalenecarboxaldehyde.

EXAMPLE 170

(E)-3-[7-Methoxy-1-(3-methoxyphenyl)-2-naphthalenyl]-2-propenoic acid

A solution of 7-methoxy-1-(3-methoxyphenyl)-2-naphthalenecarboxaldehyde (1.6 g) and (carbethoxymethylene)triphenylphosphorane (2.1 g) in dichloromethane (15 mL) was stirred at room temperature overnight. The mixture was evaporated to dryness and the residue was dissolved in a mixture of methanol (15 mL) and 4N potassium hydroxide solution and heated at reflux for 1.25 hours. After the methanol was removed under reduced pressure, the reaction was diluted with water (15 mL) and was extracted with dichloromethane (3×10 mL) to remove neutral impurities. The aqueous layer was acidified, extracted with dichloromethane (6×25 mL), then the combined extracts were dried (MgSO$_4$) and evaporated to furnish 1.35 g of crude (E)-3-[7-methoxy-1-(3-methoxyphenyl)-2-naphthalenyl]-2-propenoic acid. Crystallization of the material from toluene-hexane yielded 1.03 g of the acid, mp 198.5°–202° C. Anal. Calcd for $C_{21}H_{18}O_4$: C, 75.43; H, 5.43 Found: C, 75.64; H, 5.61

EXAMPLE 171

(E)-3-[7-Methoxy-1-(3-methoxyphenyl)-2-naphthalenyl]-2-propenoic acid 4-nitrophenyl ester As in Example 113, (E)-3-[7-methoxy-1-(3-methoxyphenyl)-2-naphthalenyl]-2-propenoic acid (0.982 g) was reacted with 4-nitrophenol (0.493 g) in dichloromethane (10 mL) in the presence of 1,3-dicyclohexylcarbodiimide (606 g) at room temperature overnight. The usual work up provided 1.2 g of (E)-3-[7-methoxy-1-(3-methoxyphenyl)-2-naphthalenyl]-2-propenoic acid 4-nitrophenyl ester.

EXAMPLE 172

(E)-3-[7-Methoxy-1-(3-methoxyphenyl)-2-naphthalenyl]-N-[4-(3-pyridinyl)butyl]-2-propenamide As in Example 114, (E)-3-[7-methoxy-1-(3-methoxyphenyl)-2-naphthalenyl]-2-propenoic acid 4-nitrophenyl ester (1.2 g) was reacted with 3-pyridinebutanamine (0.46 g) in tetrahydrofuran (12 mL) for 2 hours at room temperature. The crude product, isolated in the usual manner was purified by using HPLC (ethyl acetate) and then was crystallized from diethyl ether to yield 0.83 g of (E)-3-[7-methoxy-1-(3-methoxyphenyl)-2-naphthalenyl]-N-[4-(3-pyridinyl)butyl]-2-propenamide, mp 108.5°–110° C. Anal. Calcd for $C_{30}H_{30}N_2O_3 \cdot 0.15\ H_2O$: C, 76.78; H, 6.51; N, 5.97; $H_2O$, 0.57 Found: C, 76.68; H, 6.51; N, 6.04; $H_2O$, 0.57

EXAMPLE 173

6-Methoxy-3-pentyl-1H-indene

A solution of pentyl magnesium bromide (2M; 83 mL) was added with stirring to a chilled (−5° C.) solution of 5-methoxy-1-indenone (24.33 g) in dry tetrahydrofuran (100 mL) and the mixture was stirred at room temperature for 1.5 hours. A few chips of ice were added to destroy excess reagent and after the solvents had been removed under reduced pressure, the residue was taken up in a mixture of dichloromethane (250 mL) and 2N hydrochloric acid and stirred at room temperature for 3 hours. The separated aqueous phase was extracted with dichloromethane (150 mL) then the combined organic layers were dried ($MgSO_4$) and evaporated to provide 30 g of crude product as an oil. Purification of the material by HPLC (dichoromethane-hexane; 2:5) gave 21.62 g of 6-methoxy-3-pentyl-1H-indene as an oil

EXAMPLE 174

6-Methoxy-3-pentyl-1H-2-indenecarboxaldehyde

As in Example 109, 6-methoxy-3-pentyl-1H-indene (21.6 g) was reacted with the reagent formed from the addition of phosphorus oxychloride (10.25 mL) to dimethylformamide (70 mL) at −5° C. The cooling bath was withdrawn and after the reaction stirred at room temperature for 1.5 hours, excess reagent was destroyed by the addition of a few ice chips followed in 5 minutes by the addition of 10N sodium hydroxide (70 mL). The reaction was heated to 110° C. for 10 minutes, then it was worked up in the described manner to give the crude aldehyde. Purification of the crude product by HPLC (dichloromethane-hexane; 3:2) gave 8.6 g of 6-methoxy-3-pentyl-1H-2-indenecarboxaldehyde as an oil.

EXAMPLE 175

(E)-3-(6-Methoxy-3-pentyl-1H-inden-2-yl)-2-propenoic acid methyl ester

As in Example 111, 6-methoxy-3-pentyl-1H-2-indenecarboxaldehyde (8.5 g) and (carbomethoxymethylene)triphenylphosphorane (18.8 g) in dichloromethane (75 mL) was stirred at room temperature for 42 hours. The crude reaction product from the normal work up was purified by HPLC (diethyl ether-hexane; 1:3) to provide 6.4 g of (E)-3-(6-methoxy-3-pentyl-1H-inden-2-yl)-2-propenoic acid methyl ester as an oil.

EXAMPLE 176

(E)-3-(6-Methoxy-3-pentyl-1H-inden-2-yl)-2-propenoic acid

As in Example 112, (E)-3-(6-methoxy-3-pentyl-1H-inden-2-yl)-2-propenoic acid methyl ester (6 g) in methanol (40 mL) was treated with 2N sodium hydroxide solution (20 mL) for 0.5 hours at reflux and worked up in the described manner. Crystallization of the crude product from ethyl acetate furnished 4.2 g of (E)-3-(6-methoxy-3-pentyl-1H-inden-2-yl)-2-propenoic acid. A sample was recrystallized from ethyl acetate-hexane to give the analytical specimen, mp 165°–166° C. Anal. Calcd for $C_{18}H_{22}O_3$: C, 75.50; H, 7.74 Found: C, 75.53; H, 7.83

EXAMPLE 177

[R-(E)]-3-(6-Methoxy-3-penthylinden-2-yl)-N-[1-methyl-4-(3-pyridinyl)butyl]-2-propenamide A suspension of (E)-3-(6-methoxy-3-pentyl-1H-inden-2-yl)-2-propenoic acid (1.43 g) in toluene (15 mL) at 0° C. was treated dropwise with a solution of oxalyl chloride (1.09 mL) in toluene (5 mL) and the reaction was stirred at room temperature for 20 minutes. After the mixture was concentrated to ∼half volume in vacuo, the resulting solution of crude acid chloride was added dropwise with stirring to a chilled (−75° C.) solution of (R)-α-methyl-3-pyridinebutanamine (0.825 g) in toluene (25 mL). The cooling bath was removed and after 1.5 hours at room temperature, the reaction was diluted with toluene (50 mL) and washed with 1N sodium hydroxide solution. The dried ($K_2CO_3$) toluene layer was evaporated and the residue crystallized two times from diethyl ether-hexane to furnish 1.55 g of [R-(E)]-3-(6-methoxy-3-pentylindene-2-yl)-N-[1-methyl-4-(3-pyridinyl)butyl]-2-propenamide, mp 104°–105.5° C. Anal. Calcd for $C_{28}H_{36}O_2$: C, 77.74; H, 8.39; N, 6.47 Found: C, 77.73; H, 8.40; N, 6.55

EXAMPLE 178

6-Methoxy-3-pentylbenzo[b]thiophene

To a stirred solution of 3-methoxythiophenolate (45 g) in water (100 mL) at 15° C. was added dropwise over 20 minutes 1-bromo-2-heptanone (54.4 g). The reaction was stirred for 1 hour at room temperature then was extracted with diethyl ether (2×250 mL) and the ether extracts were washed in turn with water (2×100 mL) and 1N hydrochloric acid (2×100 mL). The dried ($MgSO_4$) organic layers were combined and evaporated to yield crude 1-(3-methoxyphenylthio)-2-heptanone (71 g). The crude 1-(3-methoxyphenylthio)-2-heptanone (65 g) was added over 30 minutes with stirring to sulfuric acid at −10° C. After 30 minutes at −5° C., the reaction mixture was diluted carefully with ice (200 g) and the resulting solid was filtered off, washed with water and dried. Crystallization of the crude product from hexane gave 18.4 g of 6-methoxy-3-pentylbenzo[b]thiophene, mp 43°–45° C. A small sample was recrystallized from hexane to provide the analytical specimen, mp 45°–47° C. Anal. Calcd for $C_{14}H_{18}OS$: C, 71.75; H, 7.74; S, 13.68 Found: C, 71.81; H, 7.60; S, 13.37

EXAMPLE 179

6-Methoxy-3-pentyl-2-benzo[b]thiophenecarboxaldehyde

As in Example 109, 6-methoxy-3-pentylbenzo[b]thiophene (9.37 g) was reacted with the reagent formed from the addition of phosphorus oxychloride (4.1 mL) to dimethylformamide (25 mL) at −5° C. The cooling bath was withdrawn and after the reaction stirred at room temperature for 3 hours and then at 45° C. overnight, excess reagent was destroyed by the addition of a few ice chips followed in 5 minutes by the addition of 10N sodium hydroxide (50 mL). The reaction was heated to 110° C. for 10 minutes, then it was worked up in the described manner to give 9 g of crude aldehyde. Crystallization of the reaction product from hexane gave 7.83 g of 6-methoxy-3-pentyl-2-benzo[b]thiophenecarboxaldehyde, mp 44°–46° C. Recrystallization of a portion from ether furnished the pure aldehyde, mp 48.5°–50° C. Anal. Calcd for $C_{19}H_{16}O_3S$: C, 68.67; H, 6.91; S, 12.22 Found: C, 68.77; H, 7.08; S, 12.15

EXAMPLE 180

(E)-3-(6-Methoxy-3-pentylbenzo[b]thien-2-yl)-2-propenoic acid methyl ester

As in Example 111, 6-methoxy-3-pentyl-2-benzo[b]thiophenecarboxaldehyde (7.37 g) and (carbomethoxymethylene)triphenylphosphorane (9.7 g) in dichloromethane (100 mL) was stirred at room temperature for 42 hours. Crystallization of the crude reaction product, obtained by using the normal work up, from hexane gave 7.6 g of (E)-3-(6-methoxy-3-pentyl-benzo[b]thien-2-yl)-2-propenoic acid methyl ester, mp 49°–50° C. Anal. Calcd for $C_{18}H_{22}O_3S$: C, 67.90; H, 6.96: S, 10.07 Found: C, 68.21; H, 6.80; S, 10.22

EXAMPLE 181

(E)-3-(6-Methoxy-3-pentylbenzo[b]thien-2-yl)-2-propenoic acid

As in Example 112, (E)-3-(6-methoxy-3-pentylbenzo[b]thien-2-yl)-2-propenoic acid methyl ester (7.45 g) in methanol (40 mL) was treated with 2N sodium hydroxide solution (25 mL) at reflux for 15 minutes and the normal isolation procedure afforded 7.1 g of (E)-3-(6-methoxy-3-pentylbenzo[b]thien-2-yl)-2-propenoic acid. Crystallization of a sample from 2-propanol provided the analytical specimen, mp 209°–210° C. Anal. Calcd for $C_{17}H_{20}O_3S$: C, 67.08; H, 6.62; S, 10.53 Found: C, 66.51; H, 6.49; S, 10.31

EXAMPLE 182

(E)-3-(6-Methoxy-3-pentylbenzo[b]thien-2-yl)-2-propenoic acid 4-nitrophenyl ester As in Example 113, (E)-3-(6-methoxy-3-pentylbenzo[b]thien-2-yl)-2-propenoic acid (7 g) was reacted with 4-nitrophenol (3.6 g) in dichloromethane (70 mL) in the presence of 1,3-dicyclohexylcarbodiimide (4.8 g). The crude reaction product was crystallized from dichloromethane-2-propanol to give 8.1 g of (E)-3-(6-methoxy-3-pentylbenzo[b]thien-2-yl)-2-propenoic acid 4-nitrophenyl ester, mp 111°–113° C. Anal. Calcd for $C_{23}H_{23}NO_5S$: C, 64.92; H, 5.45; N, 3.29; S, 7.54 Found: C, 64.64; H, 5.35; N, 3.27; S, 7.67

EXAMPLE 183

[R-(E)]-3-(6-Methoxy-3-pentylbenzo[b]thien-2-yl)-N-[1-methyl-4-(3-pyridinyl)butyl]-2-propenamide As in Example 114, (E)-3-(6-methoxy-3-pentylbenzo[b]thien-2-yl)-2-propenoic acid 4-nitrophenyl ester (4.25 g) was reacted with (R)-α-methyl-3-pyridinebutanamine (1.64 g) in tetrahydrofuran (40 mL). The product was isolated in the usual manner and the crude amide was then crystallized from ethyl acetate to give 3.7 g [R-(E)]-6-methoxy-3-pentylbenzo[b]thien-2-yl)-N-[1-methyl-4-(3-pyridinyl)butyl]-2-propenamide, mp 132°–133° C. Anal. Calcd for $C_{27}H_{34}N_2O_2S$: C, 71.96; H, 7.61; N, 6.22; S, 7.11 Found: C, 72.18; H, 7.11; N, 6.27; S, 7.16

EXAMPLE 184

6-Methoxy-3-pentyl-2-benzofuranecarboxylic acid ethyl ester

A mixture of 2-chloro-3-oxooctanoic acid (51.5 g) and sodium 3-methoxyphenolate (35 g) was refluxed with stirring in benzene (250 mL) for 7 hours, then stirred at room temperature overnight. The cooled reaction was washed with water (2×250 mL) and the dried (MgSO4) organic layer was evaporated to give 70 g of a brown oil. The crude product was purified by HPLC (diethyl ether-hexane; 1:19) to give 30.45 g of 3-oxo-2-(3-methoxyphenoxy)octanoic acid ethyl ester as a colorless oil. 3-Oxo-2-(3-methoxyphenoxy)octanoic acid ethyl ester (21.5 g) was added over 1 hour with stirring to sulfuric acid (22 mL) at −10° C. After 1 hour at −10° C., the reaction was diluted carefully with ice (400 g) and then extracted with diethyl ether (2×400 mL). The organic extracts were washed in turn with saturated sodium bicarbonate solution and with brine, then were combined, dried (MgSO4) and evaporated. The crude reaction product was crystallized from hexane to give 10.86 g of 6-methoxy-3-pentyl-2-benzofuranecarboxylic acid ethyl ester, mp 38°–41° C.

EXAMPLE 185

6-Methoxy-3-pentyl-2-benzofurancarboxaldehyde

As in Example 152, sodium bis(2-methoxyethoxy)aluminum hydride in toluene (3.4M; 33.6 mL) and toluene (30 mL) pretreated with N-methypiperazine (13.5 mL) in toluene (20 mL) was reacted with 6-methoxy-3-pentyl-2-benzofurancarboxylic acid ethyl ester (6 g) in toluene (90 mL) for 30 minutes at −45° C. The previously described work up yielded 4.82 g of 6-methoxy-3-pentyl-2-benzofurancarboxaldehyde as an oil.

EXAMPLE 186

(E)-3-(6-Methoxy-3-pentylbenzofuran-2-yl)-2-propenoic acid methyl ester

As in Example 111, 6-methoxy-3-pentyl-2-benzofurancarboxaldehyde (4.82 g) and (carbomethoxymethylene)triphenylphosphorane (6.7 g) in dichloromethane (75 mL) was stirred at room temperature for 42 hours. Purification of the crude reaction product by HPLC (diethyl ether-hexane; 1:12) gave 4.55 g of (E)-3-(6-methoxy-3-pentylbenzofuran-2-yl)-2-propenoic acid methyl ester as an oil.

EXAMPLE 187

(E)-3-(6-Methoxy-3-pentylbenzofuran-2-yl)-2-propenoic acid

As in Example 112, (E)-3-(6-methoxy-3-pentylbenzofuran-2-yl)-2-propenoic acid methyl ester (4.25 g) in methanol (25 mL) was treated with 2N sodium hydroxide solution (15 mL) at reflux for 1.25 hours. The crude reaction product was crystallized from ethyl acetate to provide 3.6 g of (E)-3-(6-methoxy-3-pentylbenzofuran-2-yl)-2-propenoic acid, mp 146°–147° C. Anal. Calcd for $C_{17}H_{20}O_4$: C, 70.81; H, 6.99 Found: C, 70.51; H, 6.89

EXAMPLE 188

(E)-3-(6-Methoxy-3-pentylbenzofuran-2-yl)-2-propenoic acid 4-nitrophenyl ester

As in Example 113, (E)-3-(6-methoxy-3-pentylbenzofuran-2-yl)-2-propenoic acid (3.35 g) was reacted with 4-nitrophenol (1.8 g) in dichloromethane (35 mL) in the presence of 1,3-dicyclohexylcarbodiimide (2.42 g). The crude product was crystallized from 2-propanol to afford 4.1 g of (E)-3-(6-methoxy-3-pentylbenzofuran-2-yl)-2-propenoic acid 4-nitrophenyl ester, mp 120°–121.5° C. Anal. Calcd for $C_{23}H_{23}NO_6$: C, 67.47; H, 5.66; N, 3.42 Found: C, 67.29; H, 5.89; N, 3.43

EXAMPLE 189

[R-(E)]-3-(6-Methoxy-3-pentylbenzofuran-2-yl)-N-[1-methyl-4-(3-pyridinyl)butyl]-2-propenamide As in Example 114, (E)-3-(6-methoxy-3-pentylbenzofuran-2-yl)-2-propenoic acid 4-nitrophenyl ester (2.05 g) was reacted with (R)-α-methyl-3-pyridinebutanamine (0.825 g) in tetrahydrofuran (25 mL). The product was isolated in the usual manner and the crude amide was then crystallized from ethyl acetate-hexane to provide [R-(E)]-3-(6-methoxy-3-pentylbenzofuran-2-yl)-N-[1-methyl-4-(3-pyridinyl)butyl]-2-propenamide, mp 122°–124° C. Anal. Calcl for $C_{27}H_{34}N_2O_3$: C, 74.62; H, 7.89; N, 6.45 Found: C, 74.69; H, 7.77; N, 6.37

EXAMPLE 190

6-Methoxy-1-methyl-3-pentyl-2-indolecarbonitrile

A solution of 3-methoxy-N-methylaniline (9.8 g) and 2-chloro-3-oxooctanenitrile (6.2 g) in ethanol (25 mL) was heated at reflux for 17 hours then the solvent was removed under reduced pressure. The residue was dissolved in dichloromethane (100 mL) and washed with 1N hydrochloric acid (3×50 mL). The aqueous layers were backwashed in turn with dichloromethane (50 mL) and the combined organic layers were dried ($K_2CO_3$) and evaporated. The residual oil was purified by HPLC (diethyl ether-hexane; 3:7) to yield 6.42 g of 2-(3-methoxy-N-methylanilino)-3-oxooctanenitrile as an oil. The above material was dissolved in trifluoroacetic acid (15 mL) and the solution was allowed to stand overnight at ambient temperature. The solvent was then evaporated and the residue was partitioned between dichloromethane (100 mL) and 1N sodium hydroxide solution (100 mL). The dried ($K_2CO_3$) organic layer was evaporated and the residue was purified by HPLC (diethyl ether-hexane; 1:1) to give 3.2 g of 6-methoxy-1-methyl-3-pentyl-2-indolecarbonitrile as an oil.

EXAMPLE 191

6-Methoxy-1-methyl-3-pentyl-2-indolecarboxaldehyde

A solution of diisobutylaluminum hydride in toluene (1.5M; 8.5 mL) was added with stirring to a chilled (−40° C.) solution of 6-methoxy-1-methyl-3-pentyl-2-indolecarbonitrile (2.85 g) in dry toluene (25 mL). After 10 minutes, the cooling bath was removed and the reaction was stirred at room temperature for 2 hours followed by the careful addition of 5% sulfuric acid solution (100 mL). The mixture was heated at 40° C. for 45 minutes then was cooled, diluted with toluene (75 mL) and the layers separated. The dried ($Na_2SO_4$) organic layer was evaporated to afford 2.81 g of 6-methoxy-1-methyl-3-pentyl-2-indolecarboxaldehyde as an oil.

EXAMPLE 192

(E)-3-(6-Methoxy-1-methyl-3-pentylindol-2-yl)-2-propenoic acid methyl ester

As in Example 111, 6-methoxy-1-3-pentyl-2-indolecarboxaldehyde (1.5 g) and (carbomethoxymethylene)triphenylphosphorane (2.13 g) in dichloromethane (25 mL) was stirred at room temperature for 17 hours. Work up of the reaction in the usual way afforded 2 g of (E)-3-(6-methoxy-1-methyl-3-pentylindol-2-yl)-2-propenoic acid methyl ester as an oil.

EXAMPLE 193

(E)-3-(6-Methoxy-1-methyl-3-pentylindol-2-yl)-2-propenoic acid

As in Example 112, (E)-3-(6-methoxy-1-methyl-3-pentylindol-2-yl)-2-propenoic acid methyl ester (2 g) in methanol (25 mL) was treated with 4N sodium hydroxide solution (3 mL) at reflux for 2.5 hours. The crude reaction product was isolated in the usual manner giving 0.91 g of (E)-3-(6-methoxy-1-methyl-3-pentylindol-2-yl)-2-propenoic acid. A small sample was crystallized from diethyl ether to give the analytical specimen, mp 157°–158° C. Anal. Calcd for $C_{18}H_{23}NO_3$: C, 71.73; H, 7.69; N, 4.65 Found: C, 72.06; H, 7.65; N, 4.82

EXAMPLE 194

[R-(E)]-3-(6-Methoxy-1-methyl-3-pentylindol-2-yl)-N-[1-ethyl-4-(3-pyridinyl)butyl]-2-propenamide As in Example 177, (E)-3-(6-methoxy-1-methyl-3-pentylindol-2-yl)-2-propenoic acid in toluene (25 mL) was treated with a solution of oxalyl chloride (0.8 mL) in toluene (3 mL) for 1 hour at 0° C. After the reaction mixture was concentrated to ~half volume in vacuo, the resulting solution of crude acid chloride was added dropwise with stirring to a chilled (−75° C.) solution of (R)-α-ethyl-3-pyridinebutanamine (0.535 g) and triethylamine (0.85 mL) in toluene (15 mL). The cooling bath was removed and after 1 hour at room temperature the reaction was worked up in the usual manner. Purification of the crude product by HPLC (triethylamine-ethyl acetate; 1:66) followed by crystallization of the isolated amide from ethyl acetate furnished 0.9 g of [R-(E)]-3-(6-methoxy-1-methyl-3-pentylindol-2-yl)-N-[1-ethyl-4-(3-pyridinyl)-butyl]-2-propenamide, mp 147°–148° C. Anal. Calcd for $C_{29}H_{39}N_3O_2$: C, 75.45; H, 8.52; N, 9.10 Found: C, 75.32; H, 8.75; N, 9.30

EXAMPLE 195

| INHALATION AEROSOL FORMULATION (SOLUTION) | | |
| --- | --- | --- |
| Item | Ingredients | % w/w |
| 1. | [R-(E)]-3-(1-Butyl-6-methoxy-2-naphthalenyl)-N-[1-methyl-4-(3-pyridinyl)butyl]-2-propenamide | 1.0 |
| 2. | Ethyl Alcohol | 30.0 |
| 3. | Ascorbic Acid | 0.5 |
| 4. | Freon 12 | 54.8 |
| 5. | Freon 114 | 13.7 |
| | TOTAL | 100% |

Manufacturing Procedures:
(1) Dissolve Items 1 and 3 in Item 2.
(2) Fill solution from Step 1 into a suitable glass bottle, insert valve and crimp to seal container.
(3) Pressure-fill a 80:20 mixture of Items 4 and 5 into the container.

NOTE: A suitable valve may be used to deliver 25 to 100 microliters in volume.

EXAMPLE 196

| INHALATION AEROSOL FORMULATION (SOLUTION) | | |
| --- | --- | --- |
| Item | Ingredients | % w/w |
| 1. | [R-(E)]-3-(1-Butyl-6-methoxy-2-naphthalenyl)-N-[1-methyl-4-(3-pyridinyl)butyl]-2-propenamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing Procedure:
(1) Mix Items 1 and 2 into 4 and homogenize.
(2) Fill the concentrate suspension from Step 1 into a suitable can and place in valve and crimp to seal container.
(3) Pressure-fill a 80:20 mixture of Items 3 and 5.

NOTE: A suitable valve may be used to deliver 25 to 100 microliters in volume.

EXAMPLE 197

| INHALATION AEROSOL FORMULATION (SOLUTION) | | | |
| --- | --- | --- | --- |
| | | mg/tablet | |
| Item | Ingredients | 100 mg | 500 mg |
| 1. | [r-(E)]-3-(1-Butyl-6-methoxy-2-naphthalenyl)-N-[1-methyl-4-(3-pyridinyl)butyl]-2-propenamide | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | TOTAL | 167 | 836 |

Manufacturing Procedure:
(1) Mix Items 1, 2, 3 and 4 and granulate with water.
(2) Dry the granulation at 50° CC.
(3) Pass the granulation through suitable milling equipment.
(4) Add Item 5 and mix for three minutes; compress on a suitable press.

EXAMPLE 198

| CAPSULE FORMULATION | | | |
| --- | --- | --- | --- |
| | | mg/tablet | |
| Item | Ingredients | 100 mg | 500 mg |
| 1. | [R-(E)]-3-(1-Butyl-6-methoxy-2-naphthalenyl)-N-[1-methyl-4-(3-pyridinyl)butyl]-2-propenamide | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | TOTAL | 117 | 582 |

Manufacturing Procedure:
(1) Mix Items 1, 2, and 3 and wet granulate with water. Dry at 45° C. overnight.
(2) Mill through suitable screen using appropriate milling equipment.
(3) Add Items 4 and 5 and mix for five minutes.

EXAMPLE 199

| CAPSULE FORMULATION | | | | | |
| --- | --- | --- | --- | --- | --- |
| | | mg/capsule | | | |
| Item | Ingredients | | | | |
| 1. | [R-(E)]-3-(1-Butyl-6-methoxy-2-naphthalenyl)-N-[1-methyl-4-(3-pyridinyl)butyl]-2-propenamide | 0.01 | 0.5 | 5.0 | 25.0 |
| 2. | Lactose Hydrous | 168.99 | 168.5 | 159.0 | 123.0 |
| 3. | Corn Starch | 20.0 | 20.0 | 25.0 | 35.0 |
| 4. | Talc | 10.0 | 10.0 | 10.0 | 15.0 |
| 5. | Magnesium Stearate | 1.0 | 1.0 | 1.0 | 2.0 |
| | TOTAL | 200.0 | 200.0 | 200.0 | 200.0 |

Manufacturing Procedure:
(1) Mix Items 1, 2 and 3 in a suitable mixer for 30 minutes.
(2) Add Items 4 and 5 and mix for 3 minutes.
(3) Fill into suitable capsule.

EXAMPLE 200

| WET GRANULATION FORMULATION | | | | | |
| --- | --- | --- | --- | --- | --- |
| | | mg/tablet | | | |
| Item | Ingredients | | | | |
| 1. | [R-(E)]-3-(1-Butyl-6-methoxy-2-naphthalenyl)-N-[1-methyl-4-(3-pyridinyl)butyl]-2-propenamide | 0.1 | 0.5 | 5.0 | 25.0 |
| 2. | Lactose Anhydrous DTG | 106.99 | 106.5 | 102.0 | 118.0 |
| 3. | Avicel PH 102 | 15.0 | 15.0 | 15.0 | 25.0 |
| 4. | Modified Starch | 7.0 | 7.0 | 7.0 | 10.0 |
| 5. | Magnesium Stearate | 1.0 | 1.0 | 1.0 | 2.0 |
| | TOTAL | 130.0 | 130.0 | 130.0 | 180.0 |

Manufacturing Procedure:
(1) Dissolve Item 1 in a suitable solvent such as alcohol.
(2) Spread the solution in Step 1 over Item 2, dry.
(3) Add Items 3 and 4 and mix for 10 minutes.
(4) Add magnesium stearate and mix for 3 minutes and compress.

EXAMPLE 201

| CREAM 0.5% | | |
|---|---|---|
| Ingredients | g/kg | Reasonable Variations |
| [R-(E)]-3-(1-Butyl-6-methoxy-2-naphthalenyl)-N-[1-methyl-4-(3-pyridinyl)butyl]-2-propenamide | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methylparaben | 1.50 | 1.25–1.75 |
| Propylparaben | 0.50 | 0.4–0.6 |
| Propylene Glycol | 200.00 | 150–250 |
| Purified Water | 568.05 | 475–575 |
| TOTAL | 1,015.20 | |

*3% excess
[1] Arlacel 165
[2] Tween 60

We claim:

1. A compound of the formula

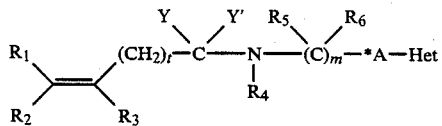

wherein Y and Y' are hydrogen or taken together are O or S, *A is paraphenylene or *—$(CH_2)_n$—$(X)_s$—$(CH_2)_r$—, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, $R_1$ and $R_2$, independently, are lower alkyl, lower alkenyl, naphthalenyl, phenyl or phenyl or naphthalenyl mono-, di-or trisubstituted by halogen, trifluoromethyl, lower alkyl, lower alkoxy, nitro or phenyl unsubstituted or mono-, di-or trisubstituted by lower alkoxy, lower alkyl or halogen, or one of $R_1$ or $R_2$ is hydrogen and the other is

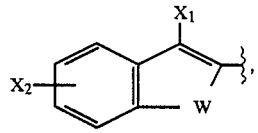

wherein W is

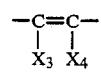

—$CH_2$—$CH_2$—, —$CH_2$—, O, S or

and $X_1$ is lower alkyl, phenyl unsubstituted or mono-, di- or trisubstituted by lower alkoxy, lower alkyl or halogen, and $X_2$, $X_3$ and $X_4$, independently, are hydrogen, lower alkyl, lower alkoxy or halogen, $R_3$ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_4$ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, naphthalenyl-lower alkyl, phenyl-lower alkyl, or phenyl-lower alkyl or naphthalenyl-lower alkyl wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, or alkanoyl of 1 to 7 carbon atoms, naphthalenyl-alkanoyl of 1 to 7 carbon atoms, phenyl-alkanoyl of 1 to 7 carbon atoms or phenylalkanoyl of 1 to 7 carbon atoms or naphthalenyl-alkanoyl of 1 to 7 carbon atoms wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_5$ is hydrogen or lower alkyl, $R_6$ is hydrogen, lower alkyl, cycloalkyl, pyridinyl-lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, Het is pyridinyl unsubstituted or substituted by lower alkyl, halogen or phenyl, which radical may be substituted by lower alkyl, halogen, naphthalenyl, phenyl or phenyl or naphthalenyl mono-, di-or trisubstituted by halogen, trifluoromethyl, lower alkyl, lower alkoxy, nitro or phenyl unsubstituted or mono-, di- or trisubstituted by lower alkoxy, lower alkyl or halogen, and the asterisk denotes the point of attachment, or, when $R_5$ and $R_6$ are different, an enantiomer or racemic mixture thereof, when $R_1$ and $R_2$ are different, a geometric isomer thereof, or a pharmaceutically acceptable acid addition salt thereof.

2. A compound, in accordance with claim 1, wherein $R_1$ and $R_2$ are lower alkyl naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, or, when $R_1$ is hydrogen, $R_2$ is

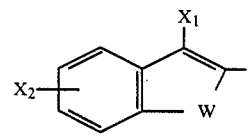

wherein $X_1$, $X_2$ and W are as previously described, $R_3$ is hydrogen or lower alkyl, $R_4$ and $R_6$ are hydrogen, $R_5$ is hydrogen, lower alkyl or cycloalkyl, *A is *—$(CH_2)_n$—$(X)_s$—$(CH_2)_r$— wherein $n+r=2$ to 6, s is 0, Het is pyridinyl unsubstituted or substituted by lower alkyl, halogen or phenyl, Y and Y' are hydrogen or taken together are oxygen or sulfur, m is 1, t is 0 to 4.

3. A compound, in accordance with claim 1, wherein R₁ is hydrogen, R₂ is

[structure: phenyl ring with X₁, X₂, W substituents]

wherein $X_1$, $X_2$ and W are as previously described, $R_3$ is hydrogen or lower alkyl, *A is *—$(CH_2)_n$—$(X)_s$—$(CH_2)_r$— wherein $n+r=3$, s is 0, Het is pyridinyl unsubstituted or substituted by lower alkyl, $R_4$ and $R_6$ are hydrogen, $R_5$ is hydrogen, lower alkyl or cyclopropyl, m is 1, t is 0, and Y and Y' are hydrogen or taken together are oxygen.

4. A compound, in accordance with claim 1, wherein $R_1$ is lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_2$ is naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_3$ is hydrogen or lower alkyl, *A is *—$(CH_2)_n$—$(X)_s$—$(CH_2)_r$— wherein $n+r=3$, s is 0, Het is pyridinyl unsubstituted or substituted with lower alkyl, $R_4$ and $R_6$ are hydrogen, $R_5$ is hydrogen, lower alkyl or cyclopropyl, m is 1, t is 0 to 2, Y and Y' are hydrogen or taken together are oxygen.

5. A compound, in accordance with claim 1, wherein $R_1$ is hydrogen, $R_2$ is

[structure: phenyl ring with X₁, X₂, W substituents]

wherein W is $$-\underset{X_3}{\overset{|}{C}}=\underset{X_4}{\overset{|}{C}}-$$

—CH₂—, O, S or $$-\underset{|}{\overset{alkyl}{N}}-,$$

$X_1$ is butyl, pentyl, hexyl, phenyl or phenyl mono-, di- or trisubstituted by halogen or lower alkoxy, $X_2$, $X_3$ and $X_4$, independently, are hydrogen, lower alkoxy or halogen, $R_3$, $R_4$ and $R_6$ are hydrogen, $R_5$ is hydrogen, lower alkyl or cycloalkyl, m is 1, t is 0, Y and Y' taken together are oxygen, and Het is 3-pyridinyl or 2-methylpyridinyl.

6. A compound, in accordance with claim 1, wherein $R_1$ is butyl, pentyl or hexyl or phenyl with up to 3-substituents selected from halogen, or lower alkoxy, $R_2$ is phenyl with up to 3-substituents selected from halogen or lower alkoxy, $R_3$, $R_4$ and $R_6$ are hydrogen, $R_5$ is hydrogen, lower alkyl or cyclopropyl, t is 2, Y and Y' are hydrogen or taken together is oxygen, Het is 3-pyridinyl or 2-methyl-3-pyridinyl.

7. A compound, in accordance with claim 1, 5,5-bis(4-methoxyphenyl)-N-[4-(3-pyridinyl)butyl]-4-pentenamide.

8. A compound, in accordance with claim 1, 5,5-diphenyl-N-[4-(3-pyridinyl)butyl]-4-pentenamide.

9. A compound, in accordance with claim 1, N-(5,5-diphenyl-4-pentenyl)-3-pyridinebutanamine.

10. A compound, in accordance with claim 1, 5,5-bis(4-fluorophenyl)-N-[4-(3-pyridinyl)butyl]-4-pentenamide.

11. A compound, in accordance with claim 1, [R-(E)]-3-(1-butyl-6-methoxy-2-naphthalenyl)-N-[1-methyl-4-(3-pyridinyl)butyl]-2-propenamide.

12. A compound, in accordance with claim 1, [R-(E)]-3-(1-butyl-4-methoxy-2-naphthalenyl)-N-[1-methyl-4-(3-pyridinyl)butyl]-2-propenamide.

13. A compound, in accordance with claim 1, [R-(E)]-3-(6-methoxy-3-pentylinden-2-yl)-N-[1-methyl-4-(3-pyridinyl)butyl]-2-propenamide.

14. A compound, in accordance with claim 1, [R-(E)]-3-(6-methoxy-3-pentylbenzo[b]thien-2-yl)-N-[1-methyl-4-(3-pyridinyl)butyl]-2-propenamide.

15. A compound, in accordance with claim 1, [R-(E)]-3-(6-methoxy-3-pentylbenzofuran-2-yl)-N-[1-methyl-4-(3-pyridinyl)butyl]-2-propenamide.

16. A compound, in accordance with claim 1, [R-(E)]-3-(6-methoxy-1-methyl-3-pentylindol-2-yl)-N-[1-ethyl-4-(3-pyridinyl)butyl]-2-propenamide.

17. A pharmaceutical composition comprising an effective amount of a compound of the formula

[structure of formula I showing: R₁R₂C=C(CH₂)ₜ—C(Y)(Y')—N(R₄)—(C)ₘ(R₅)(R₆)—*A—Het, labeled I]

wherein Y and Y' are hydrogen or taken together are O or S, *A is paraphenylene or *—$(CH_2)_n$—$(X)_s$—$(CH_2)_r$—, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, $R_1$ and $R_2$, independently, are lower alkyl, lower alkenyl naphthalenyl, phenyl or phenyl or naphthalenyl mono-, di-or trisubstituted by halogen, trifluoromethyl, lower alkyl, lower alkoxy, nitro or phenyl unsubstituted or mono-, di-or trisubstituted by lower alkoxy, lower alkyl or halogen, or one of $R_1$ or $R_2$ is hydrogen and the other is

[structure: phenyl ring with X₁, X₂, W substituents]

wherein W is $$-\underset{X_3}{\overset{|}{C}}=\underset{X_4}{\overset{|}{C}}-$$

—CH₂—CH₂—, —CH₂—, O, S or

and

X₁ is lower alkyl, phenyl unsubstituted or mono-, di- or trisubstituted by lower alkoxy, lower alkyl or halogen, and X₂, X₃ and X₄, independently, are hydrogen, lower alkyl, lower alkoxy or halogen, R₃ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, R₄ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, naphthalenyl-lower alkyl, phenyl-lower alkyl, or phenyl-lower alkyl or naphthalenyl-lower alkyl wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, or alkanoyl of 1 to 7 carbon atoms, naphthalenyl-alkanoyl of 1 to 7 carbon atoms, phenyl-alkanoyl of 1 to 7 carbon atoms or phenylalkanoyl of 1 to 7 carbon atoms or naphthalenyl-alkanoyl of 1 to 7 carbon atoms wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, R₅ is hydrogen or lower alkyl, R₆ is hydrogen, lower alkyl, cycloalkyl, pyridinyl-lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, Het is pyridinyl unsubstituted or substituted by lower alkyl, halogen or phenyl, which radical may be substituted by lower alkyl, halogen, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, and the asterisk denotes the point of attachment, or, when R₅ and R₆ are different, an enantiomer or racemic mixture thereof, when R₁ and R₂ are different, a geometric isomer thereof, or a pharmaceutically acceptable acid addition salt thereof, and an inert carrier material.

18. A pharmaceutical composition, in accordance with claim 17, wherein R₁ and R₂ are lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, R₃ is hydrogen or lower alkyl, R₄ and R₆ are hydrogen, R₅ is hydrogen, lower alkyl or cycloalkyl, *A is *—(CH₂)ₙ—(X)ₛ—(CH₂)ᵣ— wherein n+r=2 to 6, s is 0, Het is pyridinyl unsubstituted or substituted by lower alkyl, halogen or phenyl, Y and Y' are hydrogen or taken together are oxygen or sulfur, m is 1, t is 0 to 4.

19. A pharmaceutical composition, in accordance with claim 7, wherein R₁ is hydrogen, R₂ is

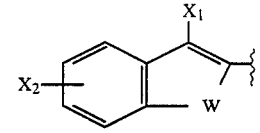

wherein X₁, X₂ and W are as previously described, R₃ is hydrogen or lower alkyl, *A is *—(CH₂)ₙ—(X)ₛ—(CH₂)ᵣ— wherein n+r=3, s is 0, Het is pyridinyl unsubstituted or substituted by lower alkyl, R₄ and R₆ are hydrogen, R₅ is hydrogen, lower alkyl or cyclopropyl, m is 1, t is 0, and Y and Y' are hydrogen or taken together are oxygen.

20. A pharmaceutical composition, in accordance with claim 17, wherein R₁ is lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, R₂ is, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, R₃ is hydrogen or lower alkyl, *A is *—(CH₂)ₙ—(X)ₛ—(CH₂)ᵣ— wherein n+r=3, s is 0, Het is pyridinyl unsubstituted or substituted with lower alkyl, R₄ and R₆ are hydrogen, R₅ is hydrogen, lower alkyl or cyclopropyl, m is 1, t is 0 to 2, Y and Y' are hydrogen or taken together are oxygen.

21. A pharmaceutical composition, in accordance with claim 17, wherein R₁ is hydrogen, R₂ is

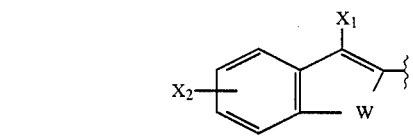

wherein W is

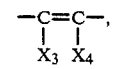

—CH₂—, O, S or alkyl
-N-, X₁ is butyl, pentyl, hexyl, phenyl or phenyl mono-, di- or trisubstituted by halogen or lower alkoxy, X₂, X₃ and X₄, independently, are hydrogen, lower alkoxy or halogen, R₃, R₄ and R₆ are hydrogen, R₅ is hydrogen, lower alkyl or cycloalkyl, m is 1, t is 0, Y and Y' taken together are oxygen, and Het is 3-pyridinyl or 2-methylpyridinyl.

22. A pharmaceutical composition, in accordance with claim 17, wherein R₁ is butyl, pentyl or hexyl or phenyl with up to 3-substituents selected from halogen, or lower alkoxy, R₂ is phenyl with up to 3-substituents selected from halogen or lower alkoxy, R₃, R₄ and R₆ are hydrogen, R₅ is hydrogen, lower alkyl or cyclopropyl, t is 2, Y and Y' are hydrogen or taken together is oxygen, Het is 3-pyridinyl or 2-methyl-3-pyridinyl.

23. A pharmaceutical composition, in accordance with claim 17, 5,5-bis(4-methoxyphenyl)-N-[4-(3-pyridinyl)butyl]-4-pentenamide.

24. A pharmaceutical composition, in accordance with claim 17, 5,5-bis(4-fluorophenyl)-N-[4-(3-pyridinyl)butyl]-4-pentenamide.

25. A pharmaceutical composition, in accordance with claim 17, [R-(E)]-3-(1-butyl-6-methoxy-2-naphthalenyl)-N-[1-methyl-4-(3-pyridinyl)butyl]-2-propenamide.

26. A pharmaceutical composition, in accordance with claim 17, [R-(E)]-3-(1-butyl-4-methoxy-2-naphthalenyl)-N-[1-methyl-4-(3-pyridinyl)butyl]-2-propenamide.

27. A pharmaceutical composition, in accordance with claim 17, [R-(E)]-3-(6-methoxy-3-pentylbenzo[b]thien-2-yl)-N-[1-methyl-4-(3-pyridinyl)butyl]-2-propenamide.

28. A pharmaceutical composition, in accordance with claim 17, [R-(E)]-3-(6-methoxy-3-pentylbenzofuran-2-yl)-N-[1-methyl-4-(3-pyridinyl)butyl]-2-propenamide.

29. A method of treating a disease state characterized by an excess of platelet activating factor which comprises administering a compound of the formula

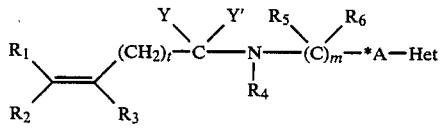

wherein Y and Y' are hydrogen or taken together are O or S, *A is paraphenylene or *—$(CH_2)_n$—$(X)_s$—$(CH_2)_r$—, X is O, S or —CH=CH—, n or r, independently, are integers from 0 to 3, m is an integer from 0 to 1, s is an integer from 0 to 1, provided that when s is 1, n+m must be at least 2, t is an integer from 0 to 10, $R_1$ and $R_2$, independently, are lower alkyl, lower alkenyl, naphthalenyl, phenyl or phenyl or naphthalenyl mono-, di-or trisubstituted by halogen, trifluoromethyl, lower alkyl, lower alkoxy, nitro or phenyl unsubstituted or mono-, di-or trisubstituted by lower alkoxy, lower alkyl or halogen, or one of $R_1$ or $R_2$ is hydrogen and the other is

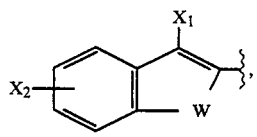

wherein W is

—CH$_2$—CH$_2$—, —CH$_2$—, O, S or

and
$X_1$ is lower alkyl, phenyl unsubstituted or mono-, di- or trisubstituted by lower alkoxy, lower alkyl or halogen, and $X_2$, $X_3$ and $X_4$, independently, are hydrogen, lower alkyl, lower alkoxy or halogen, $R_3$ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_4$ is hydrogen, lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, naphthalenyl-lower alkyl, phenyl-lower alkyl, or phenyl-lower alkyl or naphthalenyl-lower alkyl wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, or alkanoyl of 1 to 7 carbon atoms, naphthalenyl-alkanoyl of 1 to 7 carbon atoms, phenyl-alkanoyl of 1 to 7 carbon atoms or phenylalkanoyl of 1 to 7 carbon atoms or naphthalenyl-alkanoyl of 1 to 7 carbon atoms wherein phenyl or naphthalenyl are mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_5$ is hydrogen or lower alkyl, $R_6$ is hydrogen, lower alkyl, cycloalkyl, pyridinyl-lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, Het is pyridinyl unsubstituted or substituted by lower alkyl, halogen or phenyl, which radical may be substituted by lower alkyl, halogen, naphthalenyl, phenyl or phenyl or naphthalenyl mono-, di-or trisubstituted by halogen, trifluoromethyl, lower alkyl, lower alkoxy, nitro or phenyl unsubstituted or mono-, di-or trisubstituted by lower alkoxy, lower alkyl or halogen, and the asterisk denotes the point of attachment, or, when $R_5$ and $R_6$ are different, an enantiomer or racemic mixture thereof, when $R_1$ and $R_2$ are different, a geometric isomer thereof, or a pharmaceutically acceptable acid addition salt thereof.

30. A method, in accordance with claim 17, wherein $R_1$ and $R_2$ are lower alkyl, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_3$ is hydrogen or lower alkyl, $R_4$ and $R_6$ are hydrogen, $R_5$ is hydrogen, lower alkyl or cycloalkyl, *A is *—$(CH_2)_n$—$(X)_s$—$(CH_2)_r$— wherein $n+r=2$ to 6, s is 0, Het is pyridinyl unsubstituted or substituted by lower alkyl, halogen or phenyl, Y and Y' are hydrogen or taken together are oxygen or sulfur, m is 1, t is 0 to 4.

31. A method, in accordance with claim 29, wherein $R_1$ is hydrogen, $R_2$ is

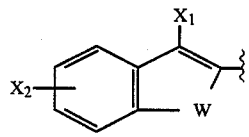

wherein $X_1$, $X_2$ and W are as previously described, $R_3$ is hydrogen or lower alkyl, *A is *—$(CH_2)_n$—$(X-)_s$—$(CH_2)_r$— wherein $n+r=3$, s is 0, Het is pyridinyl unsubstituted or substituted by lower alkyl, $R_4$ and $R_6$ are hydrogen, $R_5$ is hydrogen, lower alkyl or cyclopropyl, m is 1, t is 0, and Y and Y' are hydrogen or taken together are oxygen.

32. A method, in accordance with claim 29, wherein $R_1$ is lower alkyl or, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_2$ is, naphthalenyl, phenyl or phenyl or naphthalenyl mono-, di- or trisubstituted by halogen, trifluoromethyl, lower alkyl, lower alkoxy, nitro or phenyl unsubstituted or mono-, di- or trisubstituted by lower alkoxy, lower alkyl or halogen, $R_3$ is hydrogen or lower alkyl, *A is *—$(CH_2)_n$—$(X)_s$—$(CH_2)_r$— wherein $n+r=3$, s is 0, Het is pyridinyl unsubstituted or substituted by lower alkyl, $R_4$ and $R_6$ are hydrogen, $R_5$ is hydrogen, lower alkyl or cyclopropyl, m is 1, t is 0 to 2, Y and Y' are hydrogen or taken together oxygen.

33. A method, in accordance with claim 29, wherein $R_1$ is hydrogen, $R_2$ is

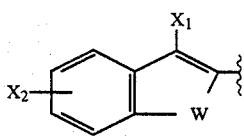

wherein W is

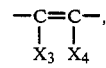

—$CH_2$—, O, S or alkyl -N-, $X_1$ is butyl, pentyl, hexyl, phenyl or phenyl mono-, di- or trisubstituted by halogen or lower alkoxy, $X_2$, $X_3$ and $X_4$, independently, are hydrogen, lower alkoxy or halogen, $R_3$, $R_4$ and $R_6$ are hydrogen, $R_5$ is hydrogen, lower alkyl or cycloalkyl, m is 1, t is 0, Y and Y' taken together are oxygen, and Het is 3-pyridinyl or 2-methylpyridinyl.

34. A method, in accordance with claim 29, wherein $R_1$ is butyl, pentyl or hexyl or phenyl with up to 3-substituents selected from halogen, or lower alkoxy, $R_2$ is phenyl with up to 3-substituents selected from halogen or lower alkoxy, $R_3$, $R_4$ and $R_6$ are hydrogen, $R_5$ is hydrogen, lower alkyl or cyclopropyl, t is 2, Y and Y' are hydrogen or taken together is oxygen, Het is 3-pyridinyl or 2-methyl-3-pyridinyl.

35. A method, in accordance with claim 29, 5,5-bis(4-methoxyphenyl)-N-[4-(3-pyridinyl)butyl]-4-pentenamide.

36. A method, in accordance with claim 29, 5,5-bis(4-fluorophenyl)-N-[4-(3-pyridinyl)butyl]-4-pentenamide.

37. A method, in accordance with claim 29, [R-(E)]-3-(1-butyl-6-methoxy-2-naphthalenyl)-N-[1-methyl-4-(3-pyridinyl)butyl]-2-propenamide.

38. A method, in accordance with claim 29, [R-(E)]-3-(1-butyl-4-methoxy-2-naphthalenyl)-N-[1-methyl-4-(3-pyridinyl)butyl]-2-propenamide.

39. A method, in accordance with claim 29, [R-(E)]-3-(6-methoxy-3-pentylbenzo[b]thien-2-yl)-N-[1-methyl-4-(3-pyridinyl)butyl]-2-propenamide.

40. A method, in accordance with claim 29, [R-(E)]-3-(6-methoxy-3-pentylbenzofuran-2-yl)-N-[1-methyl-4-(3-pyridinyl)butyl]-2-propenamide.

* * * * *

UNITED STATES PATENT AND TRADEMARK OFFICE
CERTIFICATE OF CORRECTION

PATENT NO. : 4,927,838

DATED : May 22, 1990

INVENTOR(S) : Robert William Guthrie, Richard Wightman Kierstead, John Guilfoyle Mullin Jr. Jefferson Wright Tilley It is certified that error appears in the above-identified patent and that said Letters Patent is hereby corrected as shown below:

Claim 2, Column 90, Line 58, (formula)

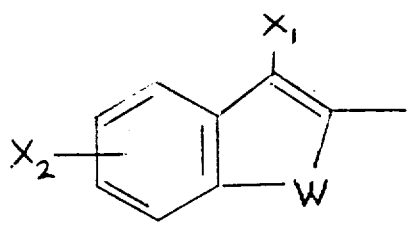 should be 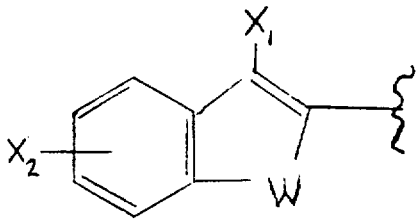

Signed and Sealed this

Eleventh Day of June, 1991

Attest:

HARRY F. MANBECK, JR.

Attesting Officer

Commissioner of Patents and Trademarks